(12) United States Patent
Vakalopoulos et al.

(10) Patent No.: US 9,187,428 B2
(45) Date of Patent: Nov. 17, 2015

(54) SUBSTITUTED DICYANOPYRIDINES AND USE THEREOF

(75) Inventors: Alexandros Vakalopoulos, Hilden (DE); Daniel Meibom, Wuppertal (DE); Peter Nell, Woodside, CA (US); Frank Sussmeier, München (DE); Barbara Albrecht-Kupper, Wülfrath (DE); Katja Zimmermann, Düsseldorf (DE); Joerg Keldenich, Wuppertal (DE); Dirk Schneider, Wuppertal (DE); Ursula Krenz, Leichlingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 9 days.

(21) Appl. No.: 13/805,653

(22) PCT Filed: Jun. 27, 2011

(86) PCT No.: PCT/EP2011/060735
§ 371 (c)(1),
(2), (4) Date: Mar. 7, 2013

(87) PCT Pub. No.: WO2012/000945
PCT Pub. Date: Jan. 5, 2012

(65) Prior Publication Data
US 2013/0210795 A1  Aug. 15, 2013

(30) Foreign Application Priority Data
Jun. 30, 2010 (DE) .................. 10 2010 030 688

(51) Int. Cl.
| | | |
|---|---|---|
| *C07D 213/85* | (2006.01) |
| *A61K 31/444* | (2006.01) |
| *A61K 31/395* | (2006.01) |
| *A61K 31/44* | (2006.01) |
| *A61K 31/4427* | (2006.01) |
| *A61K 45/06* | (2006.01) |
| *C07D 213/62* | (2006.01) |
| *C07D 213/84* | (2006.01) |
| *C07D 401/04* | (2006.01) |
| *C07D 401/10* | (2006.01) |
| *C07D 401/12* | (2006.01) |
| *C07D 401/14* | (2006.01) |
| *C07D 405/04* | (2006.01) |
| *C07D 405/12* | (2006.01) |
| *C07D 405/14* | (2006.01) |
| *A61K 31/4418* | (2006.01) |
| *A61K 31/4545* | (2006.01) |

(52) U.S. Cl.
CPC ............ *C07D 213/85* (2013.01); *A61K 31/395* (2013.01); *A61K 31/44* (2013.01); *A61K 31/444* (2013.01); *A61K 31/4418* (2013.01); *A61K 31/4427* (2013.01); *A61K 31/4545* (2013.01); *A61K 45/06* (2013.01); *C07D 213/62* (2013.01); *C07D 213/84* (2013.01); *C07D 401/04* (2013.01); *C07D 401/10* (2013.01); *C07D 401/12* (2013.01); *C07D 401/14* (2013.01); *C07D 405/04* (2013.01); *C07D 405/12* (2013.01); *C07D 405/14* (2013.01)

(58) Field of Classification Search
CPC ........................... C07D 213/85; A61K 31/444
USPC ................... 546/257, 258; 514/334
See application file for complete search history.

(56) References Cited

U.S. PATENT DOCUMENTS

| | | |
|---|---|---|
| 4,052,510 A | 10/1977 | Simpson et al. |
| 5,670,525 A | 9/1997 | Urbahns et al. |
| 5,889,002 A | 3/1999 | Nielsen et al. |
| 6,191,280 B1 | 2/2001 | Hamprecht et al. |
| 6,586,441 B2 | 7/2003 | Borroni et al. |
| 6,632,823 B1 | 10/2003 | Vernier et al. |
| 6,693,102 B2 | 2/2004 | Stasch et al. |
| 6,706,717 B2 | 3/2004 | Barrish et al. |
| 6,743,798 B1 | 6/2004 | Straub et al. |
| 6,833,364 B1 | 12/2004 | Straub et al. |
| 6,864,287 B1 | 3/2005 | Alonso-Alija et al. |
| 7,045,631 B2 | 5/2006 | Rosentreter et al. |
| 7,078,417 B2 | 7/2006 | Rosentreter et al. |
| 7,109,218 B2 | 9/2006 | Rosentreter et al. |
| 7,129,255 B2 | 10/2006 | Rosentreter et al. |
| 7,135,486 B1 | 11/2006 | Rosentreter et al. |
| 7,173,036 B2 | 2/2007 | Sircar et al. |
| 7,173,037 B2 | 2/2007 | Alonso-Alija et al. |
| 7,186,716 B2 | 3/2007 | Wei et al. |

(Continued)

FOREIGN PATENT DOCUMENTS

| | | |
|---|---|---|
| CA | 2698170 | 2/2009 |
| EP | 0608565 | 12/1993 |

(Continued)

OTHER PUBLICATIONS

Bernstein "Polymorphism in Molecular Crystal . . . " p. 115-118, 272 (2002).*

(Continued)

Primary Examiner — Patricia L Morris
(74) Attorney, Agent, or Firm — Karen B. King

(57) ABSTRACT

The present application relates to novel substituted dicyanopyridines, to processes for their preparation, to their use for the treatment and/or prophylaxis of diseases and to their use for preparing medicaments for the treatment and/or prophylaxis of diseases, preferably for the treatment and/or prophylaxis of cardiovascular disorders.

5 Claims, No Drawings

(56) References Cited

U.S. PATENT DOCUMENTS

| | | | |
|---|---|---|---|
| 7,674,825 B2 | 3/2010 | Alonso-Alija et al. |
| 7,692,017 B2 | 4/2010 | Dinsmore et al. |
| 7,705,043 B2 | 4/2010 | Alonso-Alija et al. |
| 7,709,504 B2 | 5/2010 | Krahn et al. |
| 7,781,470 B2 | 8/2010 | Alonso-Alija et al. |
| 7,825,255 B2 | 11/2010 | Rosentreter et al. |
| 7,855,219 B2 | 12/2010 | Rosentreter et al. |
| 7,932,259 B2 | 4/2011 | Nakazato et al. |
| 7,951,811 B2 | 5/2011 | Nakazato et al. |
| 8,242,281 B2 | 8/2012 | Rosentreter et al. |
| 8,304,412 B2 | 11/2012 | Nell et al. |
| 8,420,825 B2 | 4/2013 | Vakalopoulos et al. |
| 8,426,602 B2 | 4/2013 | Meibom et al. |
| 8,440,700 B2 | 5/2013 | Nell et al. |
| 2003/0232860 A1 | 12/2003 | Harada et al. |
| 2004/0162427 A1 | 8/2004 | Rosentreter et al. |
| 2004/0176446 A1 | 9/2004 | Alonso-Alija et al. |
| 2005/0182105 A1 | 8/2005 | Nirschi et al. |
| 2005/0227972 A1 | 10/2005 | Rosentreter et al. |
| 2005/0250774 A1 | 11/2005 | Ono et al. |
| 2006/0264432 A1 | 11/2006 | Rosentreter et al. |
| 2007/0066630 A1 | 3/2007 | Palani et al. |
| 2007/0293670 A1 | 12/2007 | Nakazato et al. |
| 2008/0167321 A1 | 7/2008 | Kamboj et al. |
| 2008/0269300 A1 | 10/2008 | Erguden et al. |
| 2009/0221649 A1 | 9/2009 | Krahn et al. |
| 2010/0009973 A1 | 1/2010 | Rhodes et al. |
| 2010/0048641 A1 | 2/2010 | Nell et al. |
| 2010/0069363 A1 | 3/2010 | Nell et al. |
| 2010/0093728 A1 | 4/2010 | Nell et al. |
| 2010/0279970 A1 | 11/2010 | Barman et al. |
| 2011/0136871 A1 | 6/2011 | Hübsch et al. |
| 2011/0237629 A1 | 9/2011 | Meibom et al. |
| 2011/0294718 A1 | 12/2011 | Lerchen et al. |

FOREIGN PATENT DOCUMENTS

| | | |
|---|---|---|
| JP | 09132529 | 5/1997 |
| JP | 10324687 | 12/1998 |
| JP | 2003183254 | 7/2003 |
| WO | 9534563 | 12/1995 |
| WO | 9727177 | 7/1997 |
| WO | 9903861 | 1/1999 |
| WO | 02048115 | 6/2002 |
| WO | 02050071 | 6/2002 |
| WO | 03091246 | 11/2003 |
| WO | 2004014372 | 2/2004 |
| WO | 2004054505 | 7/2004 |
| WO | 2005007647 | 1/2005 |
| WO | 2007073855 | 7/2007 |
| WO | 2008008059 | 1/2008 |

OTHER PUBLICATIONS

Braga et al. "Making crystals . . . " Roy. Soc. Chem. Chem. Commun. p. 3635-3645 (2005).*
Davidovich et al. "Detection of poly . . . " Am. Pharm. Rev. 7(1) p. 10, 12, 14,16,100 (2004).*
Dean "Analytical Chem . . . " p. 10.24-10.26 (1993).*
Invanisevic et al. "uses of x-ray powder . . . " Pharm. Sci. Encyclopedia p. 1-42 (2010).*
Kirk-Othmer "Crystallization" Encycl. of Chem. Tech. v.8, p. 95-147 (2002).*
Seddon "pseudopolym . . . " Crystal growth & design v.4(6) 1087 (2004).*
Tung et al, "Polymorphism" Cryst. Org. Compounds, p. 49 (2009).*
Jain et al., "Polymorphism in Pharmacy", Indian Drugs, 1986, 23(6) 315-329.*
Guillory (in Brittain ed.), "Polymorphism in Pharmaceutical Solids.," NY: Marcel Dekker, Inc., 1999, 1-2, 125-181, 183-226.*
Anand et al., "Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

Avila et al., "A1-, A2A- and A3-subtype adenosine receptors modulate intraocular pressure in the mouse," British Journal of Pharmacology, 2001, 134:241-245.
Barnaby et al., "Structure-Activity Relationship Study of Prion Inhibition by 2-Aminopyridine-3,5-dicarbonitrile-Based Compounds: Parallel Synthesis, Bioactivity, and in Vitro Pharmacokinetics," J. Med. Chem., 2007, 50:65-73.
Barton et al., "Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.
Bauman., "Updating the Evidence that Physical Activity is Good for Health: An Epidemiological Review 2000-2003," J. Sci. Med. Sport, Apr. 2004, 7(1): Suppl:6-19.
Beaumont et al., "Design of Ester Prodrugs to Enhance Oral Absorption of Poorly Permeable Compounds: Challenges to the Discovery Scientist," Current Drug Metabolism, 2003, 4(6):461-485.
Beukers et al., "New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.
Bundgaard, "Design of Prodrugs: Bioreversible Derivatives for Various Functional Groups and Chemical Entities," Elsevier Science Publishers B.V., 1985, pp. 1092.
Castedo et al., "Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.
Inotek Pharmaceuticals Press Release, "Inotek Pharmaceuticals Presents Preclinical Data in Support of Novel Glaucoma Candidate, INO-8875 at ARVO," May 6, 2009.
Cesar et al., "Trimethylsilyldiazomethane in the Preparation of Diazoketonesvia Mixed Anhydride and Coupling Reagent Methods: A New Approach to the Arndt—Eistert Synthesis," Tetrahedron Letters, 2001, 42: 7099-7102.
Crosson, "Intraoccular Pressure Responses to the Adenosine Agonist Cyclohexyladenosine: Evidence for a Dual Mechanism of Action," IOVS, Jul. 2001, 42(8): 1837-1840.
Dhalla et al., "Pharmacology and Theraputic Applications of A1 Adenosine Receptor Ligands," Current Topics in Medicinal Chemistry, 2003, 3:369-385.
Dyachenko et al., "Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.
Dyachenko et al., "New Route to 6-Amino-4-aryl-3,5-dicyano-pyridine-2(1H)-thiones," Russian Journal of Organic Chemistry,1997, 33(7):1014-1017.
Dyachenko et al., "Michael Reaction in SyntheSis of 6-Amino-4-(4-Butoxyphenyl)-3,5- Dicyanopyridine-2(1H)-thionene," Chemistry of Heterocyclic Compounds, 1998, 34(2):188-194.
Dyachenko, "Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.
Dyachenko et al., "Synthesis and Recyclization of 4-Aryl-2,6-diamino-3,5-dicyano-4H-thiopyrans," Russian Journal of Organic Chemistry, 1998, 34(4): 557-563.
Eissa et al., "Synthesis and Biological Evaluation of Pyrido[2,3-d]pyrimidine as Antitumor Effect," Egypt. J. Chem., 2006, 49(6):761-774.
Elnagdi et al., "Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch, 1992, 47b:572-578.
El-Torgoman et al., "Nitriles in Heterocyclic Synthesis: The reaction of 2-Thiocarbamoyl Cinnamonitriles with Active Methylene Reagents," Z. Naturforsch., 1987, 42b:107-111.
Ellenbogen et al., "Trial to evaluate the management of paroxysmal superventricular tachycardia during an electrophysiology study with tecadenoson," Circulation, 2005, 111:3202-3208.

(56) References Cited

OTHER PUBLICATIONS

Elzein et al., "A1 Adenosine Receptor Agonists and their Potential Theraputic Applications," Expert Opin. Investig. Drugs, 2008, 17(12):1901-1910.

Ettmayer et al., "Lessons Learned from Marketed and Investigational Prodrugs," J. Med. Chem., May 6, 2004, 47(10) 2393-2404.

Fuentes et al., "Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto et al., "Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim et al., "Synthesis and Biological Activity of Some New Heterocyclic Quinoline Derivatives," Phosphorus, Sulfer, and Silicon, 1991, 57: 293-301.

Jacobson et al., "Adenosine Receptors as Theraputic Targets," Nat. Rev. Drug Discover.,2005, 5:247-264.

Jacobson et al., "Adenosine Receptor Ligands: Differences with Acute Versus Chronic Treatment," Trends in Pharmacological Sciences, Mar. 1996, 17(3):108-113.

Kambe et al., "Synthetic Studies Using α,β-Unsaturated Nitriles: Facile Synthesis of Pyridine Derivatives," Synthesis Communications, Jul. 1981, pp: 531-533.

Klotz et al., "Comparative Pharmacology of Human Adenosine Receptor Subtypescharacterization of Stably Transfected Receptors in CHO Cells," Naunyn-Schmiedeberg's Arch Pharmacol, 1998, 357:1-9.

Klotz, "Adenosine Receptors and their Ligands," Naunyn-Schmiedeberg's Arch. Pharmacol., 2000, 362: 382-391.

Martyn et al., "Obesity-induced Insulin Resistance and Hypoglycemia: Etiologic Factors and Molecular Mechanisms," Anesthesiology, 2008, 109:137-148.

Müller et al., "Adenosine Receptor Antagonists: Structures and Potential Therapeutic Applications," Current Pharmaceutical Design, 1996, 2:501-530.

Müller, "Adenosine Receptor Ligands-Recent Developments Part I. Agonists," Current Medicinal Chemistry, 2000, 7:1269-1288.

Müller, "Review. Cardiovascular & Renal. A1-Adenosine Receptor Antagonists," Exp. Opin. Ther. Patents, 1997, 7 (5):419-440.

Inotek Pharmaceuticals Press Release, "Inotek Pharmaceuticals Initiates Multiple-Dose Phase 2 Clinical Trial of INO-8875 in Patients with Glaucoma," Jun. 17, 2010.

Olah et al., "Cloning, Expression, and Characterization of the Unique Bovine A1 Adenosine Receptor," Journal of Biological Chemistry, May 25, 1992, 267(15):10764-10770.

Patani et al., "Bioisosterism: A Rational Approach in Drug Design," Chem. Rev., 1996, 96:3147-3176.

Pflueger et al., "Role of Adenosine in Contrast Media-Induced Acute Renal Failure in Diabetes Mellitus," Mayo Clin Proc., Dec. 2000, 75(12):1275-1283.

Poulsen et al., "Adenosine Receptors: New Opportunities for Future Drugs," Bioorganic & Medicinal Chemistry, Jan. 8, 1998, 6(6): 619-641.

Quintela et al., "Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.

Quintela et al., "Synthesis, Antihistaminic and Cytotoxic Activity of Pyridothieno- and Pyridodithienotriazines", Eur. J. Med. Chem, 1998, 33:887-897.

Rodinovskaya et al., "Substituted 4-(3-Cyanopyridin-2-ylthio)acetoacetates: New Convenient Reagents for the Synthesis of Heterocycles," Synthesis, 2006, (14): 2357-2370.

Rosenman, "Do Environmental Effects on Human Emotions Cause Cardiovascular Disorders?," Acta Physiologica Scandinavica, Supplement,1997, 161/640 (133-136), abstract retrieved from EMBASE Accession No. 97358868.

Vasudevan et al., "Aminopiperidine indazoles as orally efficacious melanin concentrating hormone receptoer-1 antagonists," Bioorg. Med. Chem. Lett. 2005, 15 (23), 5293-5297.

Vippagunta et al., "Crystalline Solids," Advanced Drug Delivery Reviews, May 16, 2001, 48(1):3-26.

West, "Solid State Chemistry and its Applications," Wiley, New York, 1988, pp:358-365.

Ye et al., "Organic Synthesis with α-Diazocarbonyl Compounds," Chem. Rev. 1994, 94:1091-1160.

Yu et al., "Physical Characterization of Polymorphic Drugs: An Integrated Characterization Strategy," Pharmaceutical Science & Technology Today, Jun. 1998, 1(3):118-127.

Zhu et al., "Design and synthesis of pyridine-pyrazolopyridine-based inhibitors of protein kinase B/Akt," Bioorg. Med. Chem. 2007, 15 (6), 2441-2452.

Ruhe et al., "Use of Antioxidant Nutrients in the Prevention and Treatment of Type 2 Diabetes," Journal of the American College of Nutrition, 2001, 20(5): 363S-369S.

Shams et al., "Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.

Sheridan, "The Most Common Chemical Replacements in Drug-Like Compounds," J Chem. Inf. Comput. Sci., 2002, 42:103-108.

Suttner et al., "The Heart in the Elderly Critically Ill Patient," Curr. Opin. Crit. Care, Oct. 2002, 8(5):389-94, abstract retrieved from MEDLINE Accession No. 2002495386, PubMed ID: 12357105.

Szydlowski et al., "Biological Role of Chromium," Diabetologia Polska, 2003, 10(3):365-370, English language abstract retrieved from EMBASE Accession No. 2004016455.

\* cited by examiner

SUBSTITUTED DICYANOPYRIDINES AND USE THEREOF

The present application relates to novel substituted dicyanopyridines, to processes for their preparation, to their use for the treatment and/or prophylaxis of diseases and to their use for preparing medicaments for the treatment and/or prophylaxis of diseases, preferably for the treatment and/or prophylaxis of cardiovascular disorders.

Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via $G_i$ proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

In humans, activation of A1 receptors by specific A1 agonists leads to a frequency-dependent lowering of the heart rate, without any effect on blood pressure. Selective A1 agonists may thus be suitable inter alia for treating angina pectoris and atrial fibrillation.

The cardioprotective action of the A1 receptors in the heart may be utilized inter alia by activating these A1 receptors with specific A1 agonists for treatment and organ protection in cases of acute myocardial infarction, acute coronary syndrome, heart failure, bypass operations, heart catheter examinations and organ transplantations.

The activation of A2b receptors by adenosine or specific A2b agonists leads, via dilation of blood vessels, to lowering of the blood pressure. The lowering of the blood pressure is accompanied by a reflectory increase in heart rate. The increased heart rate can be reduced by activation of A1 receptors using specific A1 agonists.

Thus, the combined action of selective A1/A2b agonists on the vascular system and heart rate results in a systemic lowering of the blood pressure without any relevant heart rate increase. With such a pharmacological profile, dual A1/A2b agonists can be used for treating, for example, hypertension in humans.

In adipocytes, the activation of A1 and A2b receptors leads to an inhibition of lipolysis. Thus, the selective or combined action of A1 and A1/A2b agonists on lipid metabolism results in a lowering of free fatty acids and triglycerides. In turn, in patients suffering from metabolic syndrome and in diabetics, reducing lipids leads to lower insulin resistance and improved symptoms.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", *J. Biol. Chem.* 267 (1992), pages 10764-10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference).

The "adenosine-receptor-specific" ligands known from the prior art are mainly derivatives based on natural adenosine [S.-A. Poulsen and R. J. Quinn, "Adenosine receptors: New opportunities for future drugs", *Bioorganic and Medicinal Chemistry* 6 (1998), pages 619-641]. However, most of these adenosine ligands known from the prior art have the disadvantage that their action is not really receptor-specific, that their activity is less than that of natural adenosine, that they have only very weak activity after oral administration or unwanted side-effects on the central nervous system (CNS) (A. K. Dhalla et al., Curr. Topics in Med. Chem. 2003, 3, 369-385; [E. Elzein, J. Zablocki, *Exp. Opin. Invest. Drugs* 2008, 17(12), 1901-1910]. Thus, they are mainly used only for experimental purposes. Compounds of this type which are still in clinical development are hitherto only suitable for intravenous administration.

WO 01/25210, WO 02/070484, WO 02/070485, WO 03/053441, WO 2008/028590, WO 2009/100827, WO 2009/015776 and WO 2009/112155 disclose variously substituted 3,5-dicyano-6-aminopyridines as adenosine receptor ligands for the treatment of cardiovascular disorders.

It is an object of the present invention to provide novel compounds which act as potent and selective ligands of the adenosine A1 receptor or selective dual agonists of the A1 and A2b receptors, have identical or improved physicochemical and/or pharmacokinetic properties and an advantageous therapeutic and/or pharmacological activity profile and as such are suitable for the treatment and/or prophylaxis of diseases, in particular for the treatment and/or prophylaxis of cardiovascular disorders.

The present invention provides compounds of the formula (I)

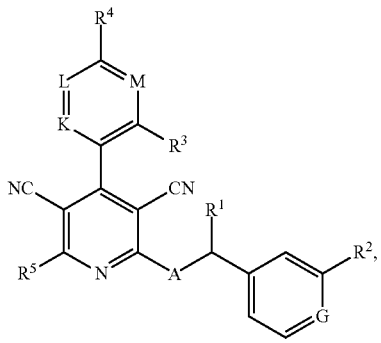

(I)

in which
A represents oxygen or sulfur,
G represents CH or N,
K represents CH, CF or N,
L represents $CR^6$ or N,
  where
  $R^6$ represents hydrogen, fluorine, chlorine, difluoromethyl, trifluoromethyl or $(C_1-C_4)$-alkoxy,
    where $(C_1-C_4)$-alkoxy may be substituted by 1 or 2 hydroxyl substituents,
M represents $CR^7$ or N,
  where
  $R^7$ represents hydrogen, fluorine, chlorine, difluoromethyl, trifluoromethyl or $(C_1-C_4)$-alkoxy,
    where $(C_1-C_4)$-alkoxy may be substituted by 1 or 2 hydroxyl substituents,
with the proviso that at most two of the groups K, L or M represent N,
$R^1$ represents hydrogen or $(C_1-C_4)$-alkyl,
$R^2$ represents hydroxycarbonyl, aminocarbonyl, mono-$(C_1-C_4)$-alkylaminocarbonyl, di-$(C_1-C_4)$-alkylaminocarbonyl, $(C_3-C_7)$-cycloalkylaminocarbonyl, aminosulfonyl, $(C_1-C_4)$-alkylsulfonylamino or phenylsulfonylamino,
  where mono-$(C_1-C_4)$-alkylaminocarbonyl, di-$(C_1-C_4)$-alkylaminocarbonyl and $(C_3-C_7)$-cycloalkylaminocarbonyl may be substituted by 1 to 3 substituents independently of one another selected from the group consisting of fluorine, hydroxy and amino,
$R^3$ represents hydrogen, fluorine or methoxy,
$R^4$ represents hydrogen, fluorine, $(C_1-C_6)$-alkoxy, mono-$(C_1-C_4)$-alkylamino, di-$(C_1-C_4)$-alkylamino, $(C_1-C_4)$-alkylcarbonylamino, mono-$(C_1-C_4)$-alkylaminosulfonyloxy, di-$(C_1-C_4)$-alkylaminosulfonyloxy or 2-oxopyrrolidin-1-yl,
  where $(C_1-C_6)$-alkoxy may be substituted by 1 to 3 substituents independently of one another selected from the group consisting of trifluoromethyl, hydroxy, $(C_1-C_4)$-alkoxy, amino, mono-$(C_1-C_4)$-alkylamino, di-$(C_1-C_4)$-alkylamino, aminocarbonyl, mono-$(C_1-C_4)$-alkylaminocarbonyl, di-$(C_1-C_4)$-alkylaminocarbonyl and a group of the formula

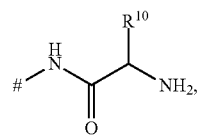

in which
  # represents the point of attachment to the alkoxy group,
  $R^{10}$ represents hydrogen or the side group of a natural α-amino acid or its homologs or isomers,
or
$R^4$ and $R^6$ together with the carbon atoms to which they are attached form a group of the formula —O—$CH_2$—O—, —O—CHF—O—, —O—$CF_2$—O—, —O—$CH_2$—$CH_2$—O— or —O—$CF_2$—$CF_2$—O—,
or
$R^4$ and $R^7$ together with the carbon atoms to which they are attached form a group of the formula —O—$CH_2$—O—, —O—CHF—O—, —O—$CF_2$—O—, —O—$CH_2$—$CH_2$—O— or —O—$CF_2$—$CF_2$—O—,
$R^5$ represents hydrogen or —$NR^8R^9$,
  where
  $R^8$ represents hydrogen or $(C_1-C_4)$-alkyl,
  $R^9$ represents hydrogen, $(C_1-C_6)$-alkyl or $(C_3-C_7)$-cycloalkyl,
    where $(C_1-C_6)$-alkoxy may be substituted by 1 or 2 substituents independently of one another selected from the group consisting of fluorine, difluoromethyl, trifluoromethyl, hydroxy and $(C_1-C_4)$-alkoxy,
  or
  $R^8$ and $R^9$ together with the nitrogen atom to which they are attached form a 4- to 7-membered heterocycle,
    where the 4- to 7-membered heterocycle may be substituted by 1 or 2 substituents independently of one another selected from the group consisting of fluorine, hydroxy and 4- to 7-membered heterocycle,
and the N-oxides, salts, solvates, salts of the N-oxides and solvates of the N-oxides and salts thereof,
except for the compounds
4-{[(6-amino-3,5-dicyano-4-phenylpyridin-2-yl)sulfanyl]methyl}-N-methylpyridine-2-carboxamide
3-[({6-amino-3,5-dicyano-4-[4-(2-hydroxyethoxy)phenyl]pyridin-2-yl}sulfanyl)methyl]benzoic acid
3-{[(6-amino-3,5-dicyano-4-phenylpyridin-2-yl)sulfanyl]methyl}benzoic acid.

Compounds according to the invention are the compounds of the formula (I) and the N-oxides, salts, solvates and solvates of the N-oxides and solvates of the salts thereof, the compounds which are encompassed by the formula (I) of the formulae mentioned below, and the N-oxides, salts, solvates and solvates of the N-oxides and solvates of the salts thereof, and the compounds which are encompassed by formula (I) and are mentioned below as exemplary embodiments, and the N-oxides, salts, solvates and solvates of the N-oxides and solvates of the salts thereof, where the compounds which are encompassed by the formula (I) and are mentioned below are not already N-oxides, salts, solvates and solvates of the N-oxides and solvates of the salts thereof.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

Depending on their structure, the compounds according to the invention may exist in different stereoisomeric forms, i.e. in the form of configurational isomers or if appropriate also as conformational isomers (enantiomers and/or diastereomers, including those in the case of atropisomers). The present invention therefore encompasses the enantiomers and diastereomers and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of an inventive compound, especially those in which one or more radioactive isotopes have been incorporated, may be beneficial, for example, for the examination of the mechanism of action or of the active ingredient distribution in the body; due to comparatively easy preparability and detectability, especially compounds labeled with $^{3}H$ or $^{14}C$ isotopes are suitable for this purpose. In addition, the incorporation of isotopes, for example of deuterium, can lead to particular therapeutic benefits as a consequence of greater metabolic stability of the compound, for example to an extension of the half-life in the body or to a reduction in the active dose required; such modifications of the inventive compounds may therefore in some cases also constitute a preferred embodiment of the present invention. Isotopic variants of the inventive compounds can be prepared by generally customary processes known to those skilled in the art, for example by the methods described below and the procedures reported in the working examples, by using corresponding isotopic modifications of the particular reagents and/or starting compounds therein.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

Alkyl is in the context of the invention a straight-chain or branched alkyl radical having 1 to 6 or 1 to 4 carbon atoms. The following radicals may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Cycloalkyl is in the context of the invention a monocyclic saturated carbocycle having 3 to 7 ring carbon atoms. The following radicals may be mentioned by way of example and by way of preference: cyclopropyl, cyclobutyl, cyclopentyl, cyclohexyl and cycloheptyl.

Alkoxy is in the context of the invention a straight-chain or branched alkoxy radical having 1 to 6 or 1 to 4 carbon atoms. A straight-chain or branched alkoxy radical having 1 to 4 carbon atoms is preferred. The following radicals may be mentioned by way of example and by way of preference: methoxy, ethoxy, n-propoxy, isopropoxy, n-butoxy, tert-butoxy, n-pentoxy and n-hexoxy.

Monoalkylamino is in the context of the invention an amino group having a straight-chain or branched alkyl substituent which has 1 to 4 carbon atoms. The following radicals may be mentioned by way of example and by way of preference: methylamino, ethylamino, n-propylamino, isopropylamino, n-butylamino and tert-butylamino.

Dialkylamino is in the context of the invention an amino group having two identical or different straight-chain or branched alkyl substituents, each of which has 1 to 4 carbon atoms. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino and N-tert-butyl-N-methylamino.

Monoalkylaminocarbonyl is in the context of the invention an amino group which is attached via a carbonyl group and has a straight-chain or branched alkyl substituent having 1 to 4 carbon atoms. The following radicals may be mentioned by way of example and by way of preference: methylaminocarbonyl, ethylaminocarbonyl, n-propylaminocarbonyl, isopropylaminocarbonyl, n-butylaminocarbonyl and tert-butylaminocarbonyl.

Dialkylaminocarbonyl is in the context of the invention an amino group which is attached via a carbonyl group and has two identical or different straight-chain or branched alkyl substituents each having 1 to 4 carbon atoms. The following radicals may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

Cycloalkylaminocarbonyl is in the context of the invention an amino group which is attached via a carbonyl group and has a monocyclic saturated carbocycle having 3 to 7 carbon atoms. The following radicals may be mentioned by way of example and by way of preference: cyclopropylaminocarbonyl, cyclobutylaminocarbonyl, cyclopentylaminocarbonyl, cyclohexyl-aminocarbonyl and cycloheptylaminocarbonyl.

Alkylcarbonylamino is in the context of the invention an amino group having a straight-chain or branched alkylcarbonyl substituent which has 1 to 4 carbon atoms in the alkyl chain and is attached via the carbonyl group to the nitrogen atom. The following radicals may be mentioned by way of example and by way of preference: methylcarbonylamino, ethylcarbonylamino, propylcarbonyl-amino, n-butylcarbonylamino, isobutylcarbonylamino and tert-butylcarbonylamino.

Alkylsulfonylamino is in the context of the invention an amino group having a straight-chain or branched alkylsulfonyl substituent which has 1 to 4 carbon atoms in the alkyl chain and is attached via the sulfonyl group to the nitrogen atom. The following radicals may be mentioned by way of example and by way of preference: methylsulfonylamino, ethylsulfonylamino, n-propyl-sulfonylamino, isopropylsulfonylamino, n-butylsulfonylamino and tert-butylsulfonylamino.

Monoalkylaminosulfonyloxy is in the context of the invention an aminosulfonyl group which is attached via an oxygen atom and has a straight-chain or branched alkyl substituent having 1 to 4 carbon atoms. The following radicals may be mentioned by way of example and by way of preference: methylaminosulfonyloxy, ethylaminosulfonyloxy, n-propylaminosulfonyloxy, iso-propylaminosulfonyloxy, n-butylaminosulfonyloxy and tert-butylaminosulfonyloxy.

Dialkylaminosulfonyl is in the context of the invention an aminosulfonyl group which is attached via an oxygen atom and has two identical or different straight-chain or branched alkyl substituents each having 1 to 4 carbon atoms. The following radicals may be mentioned by way of example and by way of preference: N,N-dimethylaminosulfonyloxy, N,N-diethylaminosulfonyloxy, N-ethyl-N-methylaminosulfonyloxy, N-methyl-N-n-propylaminosulfonyloxy, N-n-butyl-N-methylaminosulfonyloxy and N-tert-butyl-N-methylaminosulfonyloxy.

Heterocycle is in the context of the invention a saturated heterocycle having a total of 4 to 7 ring atoms which contains one or two ring heteroatoms from the group consisting of N, O and S and is attached via a ring carbon atom or, if appropriate, a ring nitrogen atom. The following radicals may be mentioned by way of example: azetidinyl, pyrrolidinyl, pyrazolidinyl, tetrahydrofuranyl, piperidinyl, piperazinyl, tetrahydropyranyl, morpholinyl, thiomorpholinyl and azepanyl. Azetidinyl, pyrrolidinyl, tetrahydrofuranyl, piperidinyl, piperazinyl, tetrahydropyranyl and morpholinyl are preferred. Azetidinyl, pyrrolidinyl, piperidinyl and morpholinyl are particular.

The side group of an α-amino acid in the meaning of $R^{10}$ encompasses both the side groups of naturally occurring α-amino acids and the side groups of homologs and isomers of these α-amino acids. The α-amino acid may in this connection have both the L and the D configuration or else be a mixture of the L form and D form. Examples of side groups which may be mentioned are: methyl (alanine), propan-2-yl (valine), propan-1-yl (norvaline), 2-methylpropan-1-yl (leucine), 1-methylpropan-1-yl (isoleucine), butan-1-yl (norleucine), tert-butyl (2-tert-butylglycine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 2-aminoethyl (2,4-diaminobutyric acid), aminomethyl (2,3-diaminopropionic acid), 3-guanidinopropan-1-yl (arginine), 3-ureidopropan-1-yl (citrulline). Preferred α-amino acid side groups in the meaning of $R^3$ are methyl (alanine), propan-2-yl (valine), 2-methylpropan-1-yl (leucine), benzyl (phenylalanine), imidazol-4-ylmethyl (histidine), hydroxymethyl (serine), 1-hydroxyethyl (threonine), 4-aminobutan-1-yl (lysine), 3-aminopropan-1-yl (ornithine), 2-aminoethyl (2,4-diaminobutyric acid), aminomethyl (2,3-diaminopropionic acid), 3-guanidinopropan-1-yl (arginine). The L configuration is preferred in each case.

Halogen includes in the context of the invention fluorine, chlorine, bromine and iodine. Preference is given to chlorine or fluorine.

In the formula of the group with which $R^4$ may be substituted, the end point of the line marked by a # does not represent a carbon atom or a $CH_2$ group but is part of the bond to the alkoxy group.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

The present invention furthermore provides the use of the following compounds for the treatment and/or prophylaxis of diseases in humans and animals:

4-{[(6-amino-3,5-dicyano-4-phenylpyridin-2-yl)sulfanyl] methyl}-N-methylpyridine-2-carboxamide 3-[({6-amino-3,5-dicyano-4-[4-(2-hydroxyethoxy)phenyl] pyridin-2-yl}sulfanyl)methyl]benzoic acid 3-{[(6-amino-3,5-dicyano-4-phenylpyridin-2-yl)sulfanyl] methyl}benzoic acid, and the salts, solvates and solvates of the salts thereof.

In the context of the present invention, preference is given to compounds of the formula (I) in which A represents oxygen or sulfur,
G represents CH or N,
K represents CH, CF or N,
L represents $CR^6$ or N,
  where
  $R^6$ represents hydrogen or fluorine,
M represents $CR^7$ or N,
  where
  $R^7$ represents hydrogen, fluorine, chlorine, difluoromethyl, trifluoromethyl, methoxy or ethoxy,
    where ethoxy may be substituted by 1 or 2 hydroxy substituents,
with the proviso, that only one of the groups K, L or M represents N,
$R^1$ represents hydrogen or methyl,
$R^2$ represents hydroxycarbonyl, aminocarbonyl, methylaminocarbonyl, ethylaminocarbonyl, cyclopropylaminocarbonyl, cyclobutylaminocarbonyl, amino sulfonyl, methylsulfonylamino, ethylsulfonylamino or phenylsulfonylamino,
where ethylaminocarbonyl, cyclopropylaminocarbonyl and cyclobutylaminocarbonyl may be substituted by 1 or 2 substituents independently of one another selected from the group consisting of fluorine, hydroxy and amino, $R^3$ represents hydrogen or fluorine, $R^4$ represents hydrogen, fluorine, $(C_1-C_4)$-alkoxy, methylamino, ethylamino, dimethylamino, diethylamino, methylcarbonylamino, ethylcarbonylamino, dimethylaminosulfonyloxy, diethylaminosulfonyloxy or 2-oxopyrrolidin-1-yl,
where $(C_1-C_4)$-alkoxy may be substituted by 1 to 3 substituents independently of one another selected from the group consisting of trifluoromethyl, hydroxy, methoxy, ethoxy, amino, methylamino, ethylamino, dimethylamino, diethylamino, aminocarbonyl, methylcarbonylamino, ethylcarbonylamino and a group of the formula

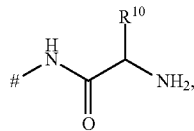

where
$R^{10}$ represents hydrogen, methyl, 2-methylpropan-1-yl, hydroxymethyl, 1-hydroxyethyl, 4-aminobutan-1-yl or 3-aminopropan-1-yl, or $R^4$ and $R^6$ together with the carbon atoms to which they are attached form a group of the formula —O—$CH_2$—O—, —O—$CF_2$—O— or —O—$CH_2$—$CH_2$—O—, or $R^4$ and $R^7$ together with the carbon atoms to which they are attached form a group of the formula —O—$CH_2$—O—, —O—$CF_2$—O— or —O—$CH_2$—$CH_2$—O—, $R^5$ represents hydrogen or —$NR^8R^9$,
where
$R^8$ represents hydrogen, methyl or ethyl,
$R^9$ represents hydrogen, $(C_1-C_6)$-alkyl or $(C_3-C_6)$-cycloalkyl,
where $(C_1-C_6)$-alkyl may be substituted by 1 or 2 substituents independently of one another selected from the group consisting of fluorine, difluoromethyl, trifluoromethyl and hydroxy,
or
$R^8$ and $R^9$ together with the nitrogen atom to which they are attached form a 4- to 7-membered heterocycle,
where the 4- to 7-membered heterocycle may be substituted by 1 or 2 substituents independently of one another selected from the group consisting of fluorine and hydroxy, and to the salts, solvates and solvates of the salts thereof,
except for the compounds
4-{[(6-amino-3,5-dicyano-4-phenylpyridin-2-yl)sulfanyl]methyl}-N-methylpyridine-2-carboxamide
3-[({6-amino-3,5-dicyano-4-[4-(2-hydroxyethoxy)phenyl]pyridin-2-yl}sulfanyl)methyl]benzoic acid
3-{[(6-amino-3,5-dicyano-4-phenylpyridin-2-yl)sulfanyl]methyl}benzoic acid.

In the context of the present invention, particular preference is given to compounds of the formula (I) in which A represents sulfur,
G represents N,
K represents CH, CF or N,
L represents $CR^6$ or N,
where
$R^6$ represents hydrogen or fluorine,
M represents $CR^7$ or N,
where
$R^7$ represents hydrogen, fluorine, trifluoromethyl, methoxy or 2-hydroxyethoxy, with the proviso, that only one of the groups K, L or M represents N,
$R^1$ represents hydrogen,
$R^2$ represents hydroxycarbonyl, aminocarbonyl, methylaminocarbonyl, ethylaminocarbonyl or cyclopropylaminocarbonyl,
$R^3$ represents hydrogen,
$R^4$ represents hydrogen, fluorine or $(C_1-C_4)$-alkoxy,
where $(C_1-C_4)$-alkoxy may be substituted by 1 or 2 substituents independently of one another selected from the group consisting of trifluoromethyl, hydroxy, amino and a group of the formula

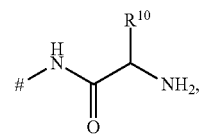

where
$R^{10}$ represents hydrogen or methyl,
$R^5$ represents hydrogen or —$NR^8R^9$,
where
$R^8$ represents hydrogen,
$R^9$ represents hydrogen, $(C_1-C_6)$-alkyl or cyclopropyl,
or
$R^8$ and $R^9$ together with the nitrogen atom to which they are attached form an azetidinyl, a pyrrolidonyl or a piperidinyl ring,
and to the salts, solvates and solvates of the salts thereof,
except for the compound
4-{[(6-amino-3,5-dicyano-4-phenylpyridin-2-yl)sulfanyl]methyl}-N-methylpyridine-2-carboxamide.

In the context of the present invention, particular preference is also given to compounds of the formula (I) in which
A represents sulfur,
G represents CH,
K represents CH, CF or N,
L represents $CR^6$ or N,
where
$R^6$ represents hydrogen or fluorine,
M represents $CR^7$ or N,
where
$R^7$ represents hydrogen, fluorine, trifluoromethyl, methoxy or 2-hydroxyethoxy, with the proviso, that only one of the groups K, L or M represents N,
$R^1$ represents hydrogen,
$R^2$ represents hydroxycarbonyl, aminocarbonyl, methylaminocarbonyl, ethylaminocarbonyl or cyclopropylaminocarbonyl,
$R^3$ represents hydrogen,
$R^4$ represents hydrogen, fluorine or $(C_1-C_4)$-alkoxy,
where $(C_1-C_4)$-alkoxy may be substituted by 1 or 2 substituents independently of one another selected from the group consisting of trifluoromethyl, hydroxy, amino and a group of the formula

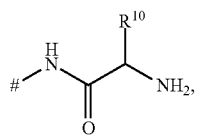

where
R¹⁰ represents hydrogen or methyl,
R⁵ represents —NR⁸R⁹,
where
R⁸ represents hydrogen,
R⁹ represents hydrogen,
and to the salts, solvates and solvates of the salts thereof.

In the context of the present invention, particular preference is also given to compounds of the formula (I) in which A represents sulfur, and to the salts, solvates and solvates of the salts thereof.

In the context of the present invention, particular preference is also given to compounds of the formula (I) in which A represents oxygen, and to the salts, solvates and solvates of the salts thereof.

In the context of the present invention, particular preference is also given to compounds of the formula (I) in which G represents N, and to the salts, solvates and solvates of the salts thereof.

In the context of the present invention, particular preference is also given to compounds of the formula (I) in which G represents CH, and to the salts, solvates and solvates of the salts thereof.

In the context of the present invention, particular preference is also given to compounds of the formula (I) in which G represents CH,
and
R² represents hydroxycarbonyl, aminocarbonyl, methylaminocarbonyl, ethylaminocarbonyl or cyclopropylaminocarbonyl,
and to the salts, solvates and solvates of the salts thereof.

In the context of the present invention, particular preference is also given to compounds of the formula (I) in which G represents CH,
and
R² represents aminocarbonyl,
and to the salts, solvates and solvates of the salts thereof.

In the context of the present invention, particular preference is also given to compounds of the formula (I) in which G represents N
and
R² represents hydroxycarbonyl, aminocarbonyl, methylaminocarbonyl, ethylaminocarbonyl, cyclopropylaminocarbonyl, cyclobutylaminocarbonyl, amino sulfonyl, methylsulfonylamino, ethylsulfonylamino or phenylsulfonylamino,
where ethylaminocarbonyl, cyclopropylaminocarbonyl and cyclobutylaminocarbonyl may be substituted by 1 or 2 substituents independently of one another selected from the group consisting of fluorine, hydroxy and amino,
and to the salts, solvates and solvates of the salts thereof.

In the context of the present invention, particular preference is also given to compounds of the formula (I) in which G represents CH
and
R² represents hydroxycarbonyl, aminocarbonyl, methylaminocarbonyl, ethylaminocarbonyl, cyclopropylaminocarbonyl, cyclobutylaminocarbonyl, amino sulfonyl, methylsulfonylamino, ethylsulfonylamino or phenylsulfonylamino,
where ethylaminocarbonyl, cyclopropylaminocarbonyl and cyclobutylaminocarbonyl may be substituted by 1 or 2 substituents independently of one another selected from the group consisting of fluorine, hydroxy and amino,
and to the salts, solvates and solvates of the salts thereof.

In the context of the present invention, particular preference is also given to compounds of the formula (I) in which
K represents CH,
L represents CR⁶,
where
R⁶ represents hydrogen,
M represents CR⁷,
where
R⁷ represents hydrogen,
R³ represents hydrogen,
and
R⁴ represents hydrogen or ethoxy,
where ethoxy is substituted by 1 or 2 substituents independently of one another selected from the group consisting of hydroxy or methoxy,
and to the salts, solvates and solvates of the salts thereof.

In the context of the present invention, particular preference is also given to compounds of the formula (I) in which
R⁵ represents —NR⁸R⁹,
where
R⁸ represents hydrogen,
R⁹ represents (C₁-C₆)-alkyl or cyclopropyl,
or
R⁸ and R⁹ together with the nitrogen atom to which they are attached form an azetidinyl, a pyrrolidonyl or a piperidinyl ring,
and to the salts, solvates and solvates of the salts thereof.

In the context of the present invention, particular preference is also given to compounds of the formula (I) in which R⁵ represents hydrogen, and to the salts, solvates and solvates of the salts thereof.

In the context of the present invention, particular preference is also given to compounds of the formula (I) in which R⁵ represents amino, and to the salts, solvates and solvates of the salts thereof.

In the context of the present invention, particular preference is also given to compounds of the formula (I) in which
R⁵ represents —NR⁸R⁹,
where
R⁸ and R⁹ together with the nitrogen atom to which they are attached form an azetidinyl, a pyrrolidonyl or a piperidinyl ring,
and to the salts, solvates and solvates of the salts thereof.

In the context of the present invention, particular preference is also given to compounds of the formula (I) in which
K represents CH,
L represents CR⁶,
where
R⁶ represents hydrogen,
M represents CR⁷,
where
R⁷ represents hydrogen,
R³ represents hydrogen,
and
R⁴ represents hydrogen or ethoxy,
where ethoxy is substituted by 1 or 2 substituents independently of one another selected from the group consisting of hydroxy or methoxy, G represents CH or N, and $R^2$ represents hydroxycarbonyl, aminocarbonyl, methylaminocarbonyl, ethylaminocarbonyl or cyclopropylaminocarbonyl, A represents S, $R^5$ represents —$NR^8R^9$, where $R^8$ represents hydrogen, $R^9$ represents hydrogen, $(C_1-C_6)$-alkyl or cyclopropyl, or $R^8$ and $R^9$ together with the nitrogen atom to which they are attached form an azetidinyl, a pyrrolidonyl or a piperidinyl ring, and to the salts, solvates and solvates of the salts thereof.

The particular radical definitions given in the respective combinations or preferred combinations of radical are independently of the respective combinations of radicals given also replaced or supplemented by any radical definitions of other combinations.

Very particular preference is given to combinations of two or more of the preferred ranges mentioned above.

The present invention furthermore provides a process for preparing the compounds of the formula (I) according to the invention, characterized in that

[A] a compound of the formula (II)

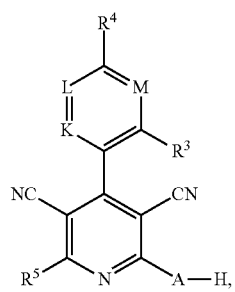

(II)

in which A, K, L, M, $R^3$, $R^4$ and $R^5$ each have the meanings given above, is reacted in an inert solvent in the presence of a base with a compound of the formula (III)

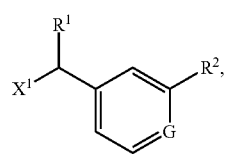

(III)

in which G, $R^1$ and $R^2$ each have the meanings given above and $X^1$ represents a suitable leaving group, preferably represents halogen, in particular chlorine, bromine or iodine, or represents mesylate, tosylate or triflate, or

[B] in the case that A represents O, a compound of the formula (IV)

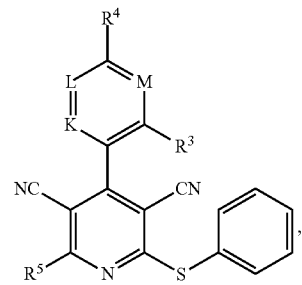

(IV)

in which K, L, M, $R^3$, $R^4$ and $R^5$ each have the meanings given above, is reacted in an inert solvent in the presence of a base with a compound of the formula (V)

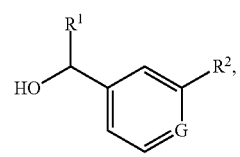

(V)

in which G, $R^1$ and $R^2$ each have the meanings given above, or

[C] a compound of the formula (I-A)

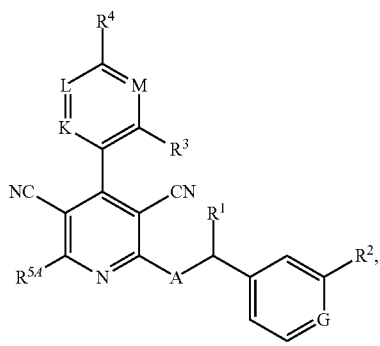

(I-A)

in which A, G, K, L, M, $R^1$, $R^2$, $R^3$ and $R^4$ each have the meanings given above and $R^{5A}$ represents amino, is initially converted in a suitable solvent with copper(II) chloride and isopentyl nitrite into a compound of the formula (VI)

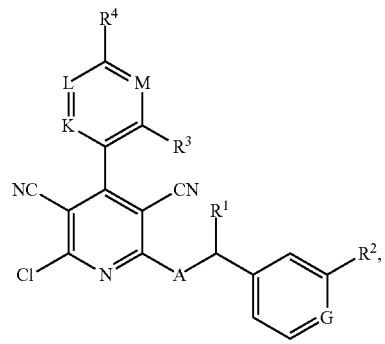

(VI)

in which A, G, K, L, M, R$^1$, R$^2$, R$^3$ and R$^4$ each have the meanings given above, and this is then reacted in an inert solvent, if appropriate in the presence of a base, with a compound of the formula (VII)

(VII)

in which R$^8$ and R$^9$ each have the meanings given above
and
where at least one of the two radicals R$^8$ and R$^9$ is different from hydrogen,
to give a compound of the formula (I-B)

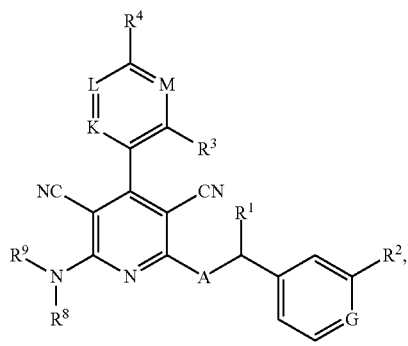
(I-B)

in which A, G, K, L, M, R$^1$, R$^2$, R$^3$, R$^4$, R$^8$ and R$^9$ each have the meanings given above,
and
where at least one of the two radicals R$^8$ and R$^9$ is different from hydrogen, any protective groups present are then removed and the resulting compounds of the formulae (I), (I-A) and (I-B) are, if appropriate, converted with the appropriate (i) solvents and/or (ii) bases or acids into their solvates, salts and/or solvates of the salts.

The process described above is illustrated in an exemplary manner by Reaction Schemes 1 to 3 below:

Scheme 1:

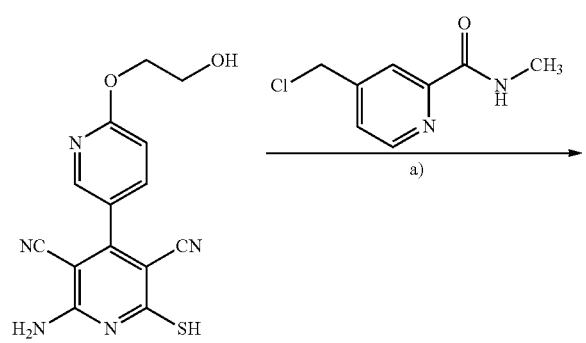

-continued

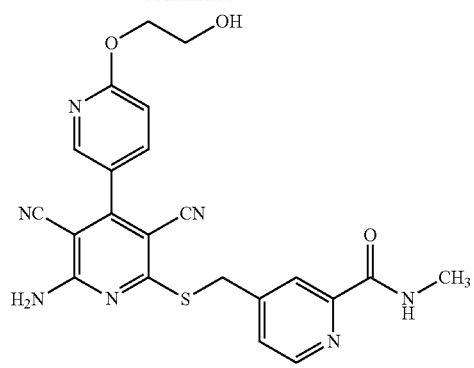

[a]: NaHCO$_3$, DMF.

Scheme 2:

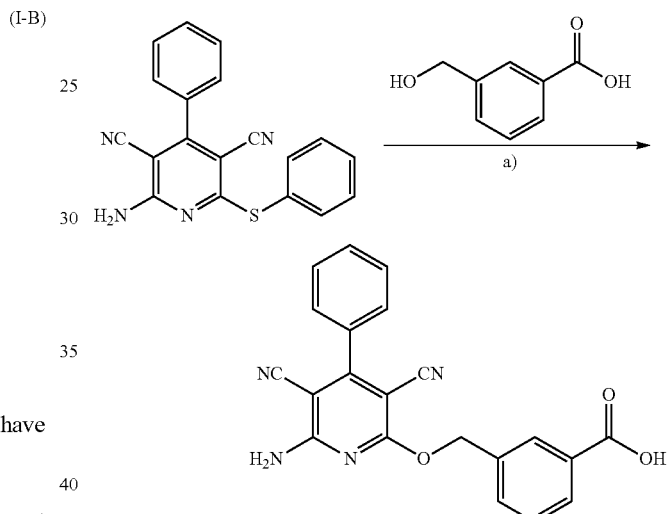

[a]: potassium tert-butoxide, DMF.

Scheme 3:

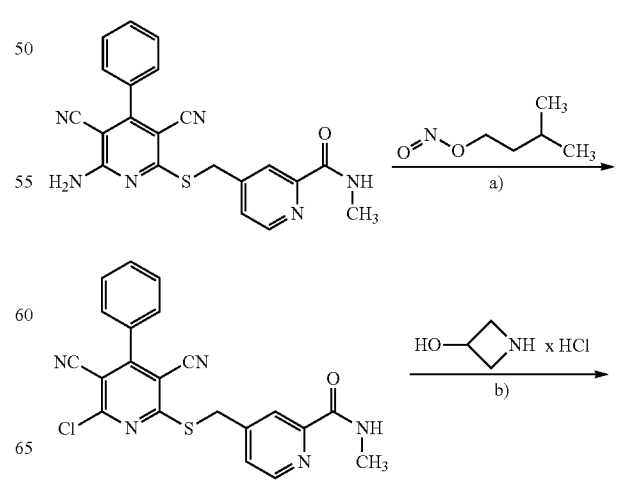

-continued

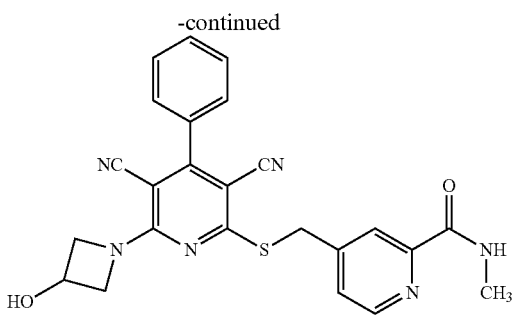

[a]: CuCl$_2$, acetonitrile, HCl; b) NEt$_3$, THF].

Suitable solvents for the reaction (II)+(III)→(I) are all organic solvents which are inert under the reaction conditions. These include ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulfoxide (DMSO), N-methylpyrrolidinone (NMP), acetonitrile or pyridine. It is also possible to use mixtures of the solvents mentioned above. Preference is given to using dimethylformamide.

Suitable bases for this reaction are the customary inorganic or organic bases. These preferably include alkali metal hydroxides, such as, for example, lithium hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethylsilyl)amide or potassium bis(trimethylsilyl)-amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and bicarbonates, such as potassium carbonate and sodium bicarbonate.

Here, the base can be employed in an amount of from 1 to 10 mol, preferably from 1 to 5 mol, in particular from 1 to 3 mol, based on 1 mol of the compound of the formula (II).

The reaction (II)+(III)→(I) is generally carried out in a temperature range of from −78° C. to +140° C., preferably in the range from −20° C. to +100° C., in particular at from 0° C. to +60° C. (for A=S) or +20° C. to +100° C. (for A=O), if appropriate in a microwave. The reaction can be carried out at atmospheric, elevated or reduced pressure (for example in the range from 0.5 to 5 bar). The reaction is generally carried out at atmospheric pressure.

Suitable inert solvents for the reaction (IV)+(V)→(I) are in particular acyclic and cyclic ethers, such as diethyl ether, methyl tert-butyl ether, 1,2-dimethoxyethane, tetrahydrofuran and dioxane, hydrocarbons, such as benzene, toluene, xylene, hexane and cyclohexane, or dipolar solvents, such as dimethylformamide (DMF), dimethyl sulfoxide (DMSO), N-methylpyrrolidinone (NMP) and pyridine. It is also possible to use mixtures of the solvents mentioned above. Preference is given to using 1,2-dimethoxyethane.

Suitable bases for this reaction are in particular alkali metal alkoxides, such as sodium methoxide or potassium methoxide, sodium ethoxide or potassium ethoxide or sodium tert-butoxide or potassium tert-butoxide, amides, such as sodium amide, lithium bis(trimethylsilyl)amide, sodium bis(trimethylsilyl)amide or potassium bis(trimethylsilyl)amide or lithium diisopropylamide, or organometallic compounds, such as butyllithium or phenyllithium. Preference is given to using potassium tert-butoxide.

Here, the base is generally employed in an amount of from 1 to 1.25 mol, preferably in an equimolar amount, based on 1 mol of the compound of the formula (V).

The reaction (IV)+(V)→(I) is generally carried out in a temperature range of from −20° C. to +120° C., preferably at from +20° C. to +100° C., if appropriate in a microwave. The reaction can be carried out at atmospheric, elevated or reduced pressure (for example in the range from 0.5 to 5 bar). The reaction is generally carried out at atmospheric pressure.

The process step (I-A)→(VI) is generally carried out using a molar ratio of from 2 to 12 mol of copper(II) chloride and from 2 to 12 mol of isopentyl nitrite, based on 1 mol of the compound of the formula (I-A).

Suitable solvents for this process step are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of these solvents. Preferred solvents are acetonitrile and dimethylformamide.

The reaction is generally carried out in a temperature range of from −78° C. to +180° C., preferably in the range from +20° C. to +100° C., in particular at from +20° C. to +60° C., if appropriate in a microwave. The reaction can be carried out at atmospheric, elevated or reduced pressure (for example in the range from 0.5 to 5 bar). The reaction is generally carried out at atmospheric pressure.

The process step (VI)+(VII)→(I-B) is generally carried out using a molar ratio of from 1 to 8 mol of the compound of the formula (VII), based on 1 mol of the compound of the formula (XV).

Suitable solvents for this process step are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile, pyridine or dimethyl sulfoxide. Another suitable solvent is water. It is also possible to use mixtures of these solvents. The preferred solvent is dimethylformamide.

The reaction is generally carried out in a temperature range of from 0° C. to +180° C., preferably in the range from +20° C. to +120° C., in particular at from +20° C. to +100° C., if appropriate in a microwave. The reaction can be carried out at atmospheric, elevated or reduced pressure (for example in the range from 0.5 to 5 bar). The reaction is generally carried out at atmospheric pressure.

The compounds of the formula (II), (III) and (VII) are either commercially available or known to the person skilled in the art, or they can be prepared by customary methods.

Compounds of the formula (II) in which A represents S and R[5] represents amino can be prepared analogously to methods known from the literature for example by reacting aldehydes of the formula (VII)

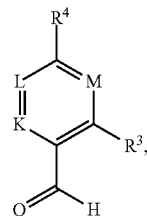

(VII)

in which K, L, M, R[3] and R[4] each have the meanings given above, in the presence of a base with two equivalents of cyanothioacetamide [see Scheme 4; cf., for example, Dyachenko et al., Russ. J. Chem. 33 (7), 1014-1017 (1997), 34 (4), 557-563 (1998); Dyachenko et al., Chemistry of Heterocyclic Compounds 34 (2), 188-194 (1998); Qintela et al., Eur. J. Med. Chem. 33, 887-897 (1998); Kandeel et al., Z. Naturforsch. 42b, 107-111 (1987); Reddy et al., J. Med. Chem. 49, 607-615 (2006); Evdokimov et al., Org. Lett. 8, 899-902 (2006)].

Scheme 4:

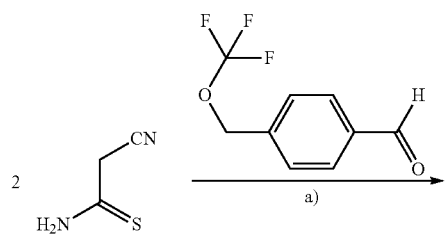

[a]: N-methylmorpholine, ethanol].

The compounds of the formula (IV) can be prepared analogously to processes described in the literature [cf., for example, Kambe et al., Synthesis, 531-533 (1981); Elnagdi et al., Z. Naturforsch. 47b, 572-578 (1991); Reddy et al., J. Med. Chem. 49, 607-615 (2006); Evdokimov et al., Org. Lett. 8, 899-902 (2006)] or by reacting compounds of the formula (II) in which X represents S analogously to processes described in the literature [cf., for example, Fujiwara, H. et al., Heterocycles 1993, 36 (5), 1105-1113, Su et al., J. Med Chem. 1988, 31, 1209-1215].

Compounds of the formula (II) in which A represents S can also be obtained starting with compounds of the formula (IV) by reaction with an alkali metal sulfide. This preparation method is illustrated by Scheme 5 below:

Scheme 5

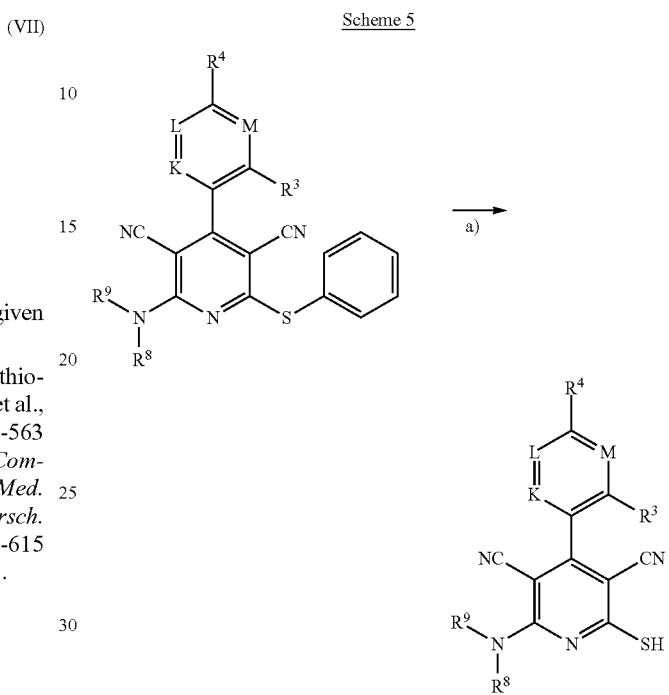

[a]: Na$_2$S, DMF].

The alkali metal sulfide employed is preferably sodium sulfide in an amount of from 1 to 10 mol, preferably from 1 to 8 mol, in particular from 1 to 5 mol, based on 1 mol of the compound of the formula (IV).

Suitable solvents for this process step are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or dipolar solvents, such as acetonitrile, pyridine, dimethylformamide, dimethyl sulfoxide or N-methylpyrrolidinone. Another suitable solvent is water. It is also possible to use mixtures of these solvents. The preferred solvent is dimethylformamide.

The reaction is generally carried out in a temperature range of from 0° C. to +180° C., preferably in the range from +20° C. to +120° C., in particular at from +40° C. to +100° C., if appropriate in a microwave. The reaction can be carried out at atmospheric, elevated or reduced pressure (for example in the range from 0.5 to 5 bar). The reaction is generally carried out at atmospheric pressure.

Compounds of the formula (IV) in which R[5] represents —NR[8]R[9] and at least one of the two radicals R[8] and R[9] does not represent hydrogen can be prepared by initially converting compounds of the formula (IVa)

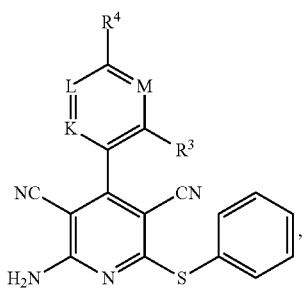

(IVa)

in which K, L, M, R³ and R⁴ each have the meanings given above, in a suitable solvent with copper(II) chloride and isopentyl nitrite into compounds of the formula (VIII)

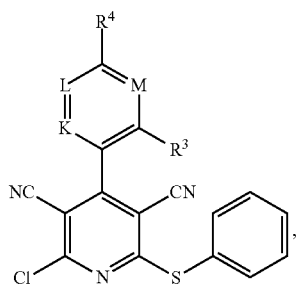

(VIII)

in which K, L, M, R³ and R⁴ each have the meanings given above, and then reacting in an inert solvent, if appropriate in the presence of a base, with compounds of the formula (VII) to give compounds of the formula (IVb)

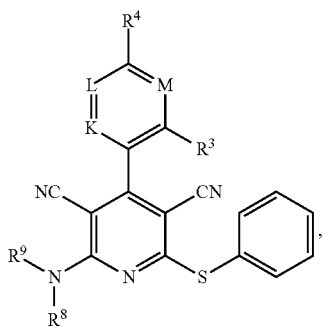

(IVb)

in which K, L, M, R³, R⁴, R⁸ and R⁹ each have the meanings given above;

if appropriate, these can then be converted with the aid of an alkali metal sulfide as described above into corresponding compounds of the formula (II) in which A represents S and at least one of the two radicals R⁸ and R⁹ does not represent hydrogen. This process can be illustrated by the reaction scheme below:

Scheme 6:

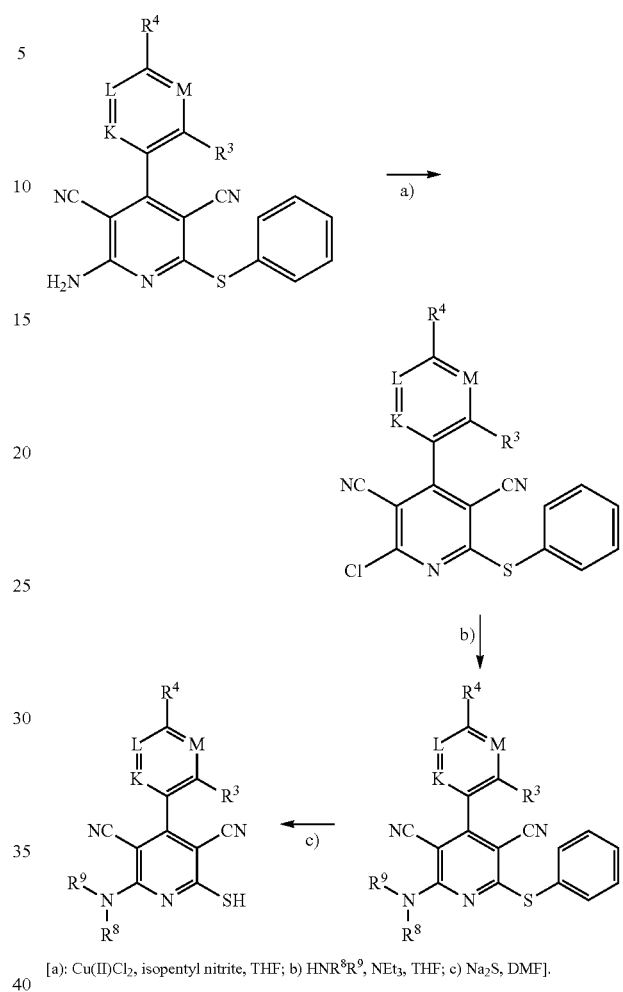

[a]: Cu(II)Cl₂, isopentyl nitrite, THF; b) HNR⁸R⁹, NEt₃, THF; c) Na₂S, DMF].

For this process path, the reaction parameters described above for the sequence (I-A)→(VI)→(I-B), such as solvents, reaction temperatures and molar ratios, are applied in an analogous manner.

Compounds of the formula (II) in which A represents O can be obtained from compounds of the formula (IV) by heating with an alkali metal hydroxide. This preparation method is illustrated by the reaction scheme below:

Scheme 7

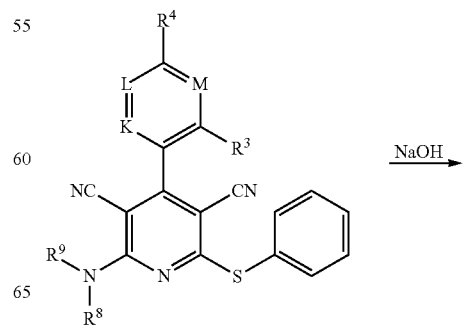

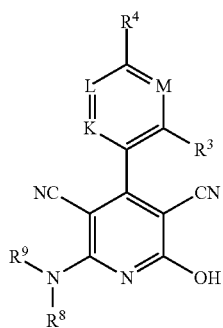

The alkali metal hydroxide used is preferably excess sodium hydroxide or potassium hydroxide. Suitable solvents are in particular alcohols, such as methanol, ethanol, n-propanol, isopropanol, n-butanol and tert-butanol, and also their mixtures with water. The reaction is generally carried out in a temperature range of from +20° C. to +120° C., preferably at from +50° C. to +100° C.

Compounds of the formula (II) or (IV) in which $R^5$ represents hydrogen can be obtained starting with compounds of the formula (II) or (IV) in which $R^5$ represents amino by reaction with copper(II) chloride and isopentyl nitrite. This method is illustrated in an exemplary manner by the scheme below (Scheme 8):

Scheme 8:

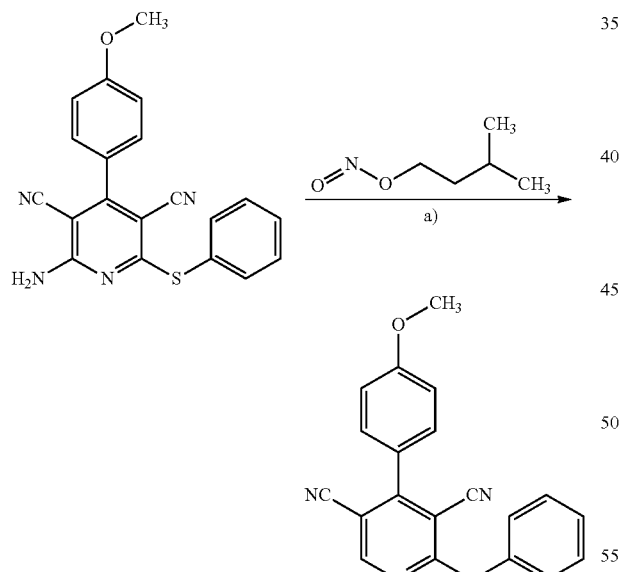

[a]: CuCl$_2$, THF, RT].

This process step is generally carried out using a molar ratio of from 2 to 5 mol of copper(II) chloride and from 0.1 to 0.9 mol of isopentyl nitrite per mole of the compound of the formula (II) or (IV).

Suitable solvents for this process step are all organic solvents which are inert under the reaction conditions. These include acyclic and cyclic ethers such as diethyl ether and tetrahydrofuran, esters such as ethyl acetate or butyl acetate, hydrocarbons such as benzene, toluene, xylene, hexane and cyclohexane, chlorinated hydrocarbons such as dichloromethane, 1,2-dichloroethane and chlorobenzene, or other solvents such as dimethylformamide, acetonitrile or pyridine. It is likewise possible to use mixtures of the solvents mentioned. THF is preferred.

The reaction is generally carried out in a temperature range of from −30° C. to +40° C., preferably in the range from 0° C. to +20° C. The reaction can take place under atmospheric, under elevated or under reduced pressure (for example from 0.5 to 5 bar). It is generally carried out under atmospheric pressure.

Other compounds according to the invention can, if appropriate, also be prepared by converting functional groups of individual substituents, in particular those listed under $R^2$, $R^4$, $R^8$ and $R^9$, starting with the compounds of the formula (I) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups. These processes are illustrated in an exemplary manner by the reaction schemes below (Schemes 9 and 10):

Scheme 9:

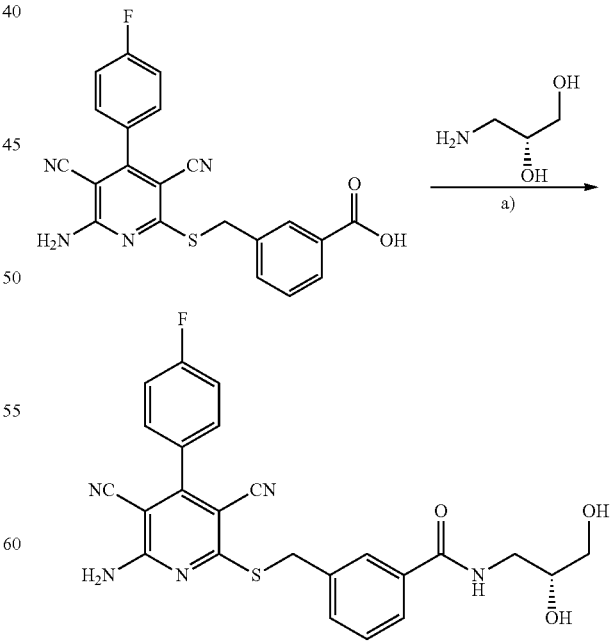

[a]: HATU, NEt(i-Pr)$_2$, DMF, RT].

Scheme 10:

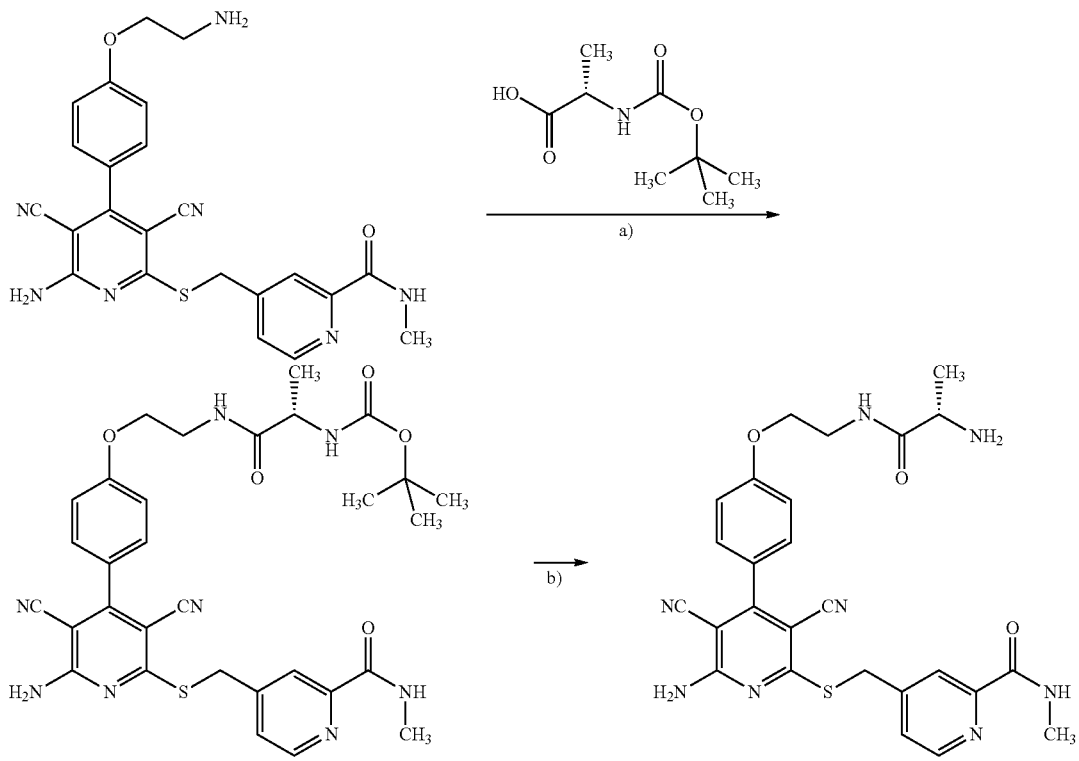

[a]: HATU, NEt(i-Pr)₂, DMF, RT; b) TFA, CH₂Cl₂, RT].

Surprisingly, the compounds according to the invention have an unforeseeable useful pharmacological activity spectrum and are therefore particularly suitable for the prophylaxis and/or treatment of disorders.

The pharmaceutical activity of the compounds according to the invention can be explained by their action as potent, selective ligands at adenosine A1 receptor and/or A2b receptor. Here, they act as selective A1 agonists or selective dual A1/A2b agonists. The compounds according to the invention have an advantageous therapeutic, pharmacological and/or physicochemical activity profile such as, for example, improved solubility in aqueous media.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in section B-1.

Depending on their particular structure, the compounds according to the invention can act as full or as partial adenosine receptor agonists. Partial adenosine receptor agonists are defined here as receptor ligands which trigger a functional response at adenosine receptors which is less than that of full agonists (such as, for example, adenosine itself). Accordingly, partial agonists have lower activity with respect to receptor activation than full agonists. With respect to the test methods for receptor activation, reference is made to the tests described in sections B-6. and B-7.

The compounds of the formula (I) are suitable alone or in combination with one or more other active ingredients for the prophylaxis and/or treatment of various disorders, for example disorders of the cardiovascular system (cardiovascular disorders), for cardio protection following lesions of the heart, and of metabolic disorders and kidney disorders.

Disorders of the cardiovascular system, or cardiovascular disorders, mean in the context of the present invention for example the following disorders: peripheral and cardiac vascular disorders, coronary heart disease, coronary restenosis such as, for example, restenosis following balloon dilatation of peripheral blood vessels, myocardial infarction, acute coronary syndrome, acute coronary syndrome with ST elevation, acute coronary syndrome without ST elevation, stable and unstable angina pectoris, myocardial insufficiency, prinzmetal angina, persistent ischemic dysfunction ("hibernating myocardium"), temporary postischemic dysfunction ("stunned myocardium"), heart failure, tachycardia, atrial tachycardia, arrhythmias, atrial and ventricular fibrillation, persistent atrial fibrillation, permanent atrial fibrillation, atrial fibrillation with normal left ventricular function, atrial fibrillation with impaired left ventricular function, Wolff-Parkinson-White syndrome, disturbances of peripheral blood flow, elevated levels of fibrinogen and of low density LDL, and elevated concentrations of plasminogen activator inhibitor 1 (PAI-1), especially coronary heart disease, acute coronary syndrome, angina pectoris, heart failure, myocardial infarction and atrial fibrillation.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are further also suitable for reducing the area of myocardium affected by an infarction, and for the prophylaxis of secondary infarctions.

The compounds according to the invention are furthermore suitable for the prophylaxis and/or treatment of thromboembolic disorders, reperfusion damage following ischemia, micro- and macrovascular lesions (vasculitis), arterial and venous thromboses, edemas, ischemias such as myocardial infarction, stroke and transient ischemic attacks, for cardio protection in connection with coronary artery bypass operations (CABG), primary PTCAs, PTCAs after thrombolysis, rescue PTCA, heart transplants and open-heart operations, and for organ protection in connection with transplants, bypass operations, catheter examinations and other surgical procedures.

Other areas of indication for which the compounds according to the invention can be employed are, for example, the prophylaxis and/or treatment of disorders of the urogenital tract, such as, for example, irritable bladder, erectile dysfunction and female sexual dysfunction, but in addition also the prophylaxis and/or treatment of inflammatory disorders, such as, for example, inflammatory dermatoses (psoriasis, acne, eczema, neurodermitis, dermatitis, keratitis, formation of scars, formation of warts, frostbites), of disorders of the central nervous system and neurodegenerative disorders (strokes, Alzheimer's disease, Parkinson's disease, dementia, epilepsy, depression, multiple sclerosis), of states of pain, cancerous diseases (skin cancer, liposarcomas, carcinomas of the gastrointestinal tract, the liver, pancreas, lung, kidney, ureter, prostate and the genital tract), and also of nausea and emesis associated with cancer therapies.

Other areas of indication are, for example, the prophylaxis and/or treatment of inflammatory and immune disorders (Crohn's disease, ulcerative colitis, lupus erythematodes, rheumatoid arthritis) and respiratory disorders, such as, for example, chronic obstructive pulmonary disease (chronic bronchitis, COPD), asthma, pulmonary emphysema, bronchiectases, cystic fibrosis (mucoviscidosis) and pulmonary hypertension, in particular pulmonary arterial hypertension.

Finally, the compounds according to the invention are also suitable for the prophylaxis and/or treatment of diabetes, in particular diabetes mellitus, gestation diabetes, insulin-dependent diabetes and non-insulin-dependent diabetes, of diabetic sequelae such as, for example, retinopathy, nephropathy and neuropathy, of metabolic disorders (metabolic syndrome, hyperglycemia, gestational diabetes, hyperinsulinemia, insulin resistance, glucose intolerance, obesity (adipositas)) and also of arteriosclerosis and dyslipidemias (hypercholesterolemia, hypertriglyceridemia, elevated concentrations of postprandial plasma triglycerides, hypoalphalipoproteinemia, combined hyperlipidemias), in particular of diabetes, metabolic syndrome and dyslipidemias.

In addition, the compounds according to the invention can also be used for the treatment and/or prophylaxis of disorders of the thyroid gland (hyperthyreosis), disorders of the pancreas (pancreatitis), fibrosis of the liver, viral diseases (HPV, HCMV, HIV), cachexia, osteoporosis, gout, incontinence, and also for wound healing and angiogenesis.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The present invention furthermore provides a method for the treatment and/or prophylaxis of disorders, in particular the disorders mentioned above, using an effective amount of at least one of the compounds according to the invention.

The present invention furthermore provides the compounds according to the invention for use in a method for the treatment and/or prophylaxis of coronary heart disease, acute coronary syndrome, angina pectoris, heart failure, myocardial infarction and atrial fibrillation.

The present invention furthermore provides the compounds according to the invention for methods for the treatment and/or prophylaxis of diabetes, metabolic syndrome and dyslipidemias.

The compounds according to the invention can be used alone or, if required, in combination with other active ingredients. The present invention furthermore provides medicaments comprising at least one of the compounds according to the invention and one or more further active ingredients, in particular for the treatment and/or prophylaxis of the disorders mentioned above.

Suitable active ingredients for combination are, by way of example and by way of preference: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists), analgesics for example aspirin, antidepressants and other psychopharmaceuticals.

The present invention relates in particular to combinations of at least one of the compounds according to the invention with at least one lipid metabolism-altering active ingredient, antidiabetic, blood pressure-reducing active ingredient and/or agent having antithrombotic effects.

The compounds according to the invention can preferably be combined with one or more lipid metabolism-modulating active ingredients, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulfonylureas, biguanides, meglitinide derivatives, glucosidase inhibitors, inhibitors of dipeptidyl-peptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists,

- inhibitors of liver enzymes involved in the stimulation of gluconeogenesis and/or glycogenolysis, modulators of glucose uptake and also potassium channel openers, such as, for example, those disclosed in WO 97/26265 and WO 99/03861;
- hypotensive active ingredients, by way of example and by way of preference from the group of the calcium antagonists, angiotensin AII antagonists, ACE inhibitors, renin inhibitors, beta-receptor blockers, alpha-receptor blockers, aldosterone antagonists, mineralocorticoid receptor antagonists, ECE inhibitors, ACE/NEP inhibitors and the vasopeptidase inhibitors; and/or
- antithrombotic agents, by way of example and by way of preference from the group of the platelet aggregation inhibitors or the anticoagulants;
- diuretics;
- vasopressin receptor antagonists;
- organic nitrates and NO donors;
- compounds with positive inotropic activity;
- compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil, and also PDE 3 inhibitors, such as milrinone;
- natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;
- agonists of the prostacyclin receptor (IP receptor), such as, by way of example, iloprost, beraprost, cicaprost;
- inhibitors of the $I_f$ (funny channel) channel, such as, by way of example, ivabradine;
- calcium sensitizers, such as, by way of example and by way of preference, levosimendan;
- potassium supplements;
- NO-independent, but heme-dependent stimulators of guanylate cyclase, such as, in particular, the compounds described in WO 00/06568, WO 00/06569, WO 02/42301 and WO 03/095451;
- NO- and heme-independent activators of guanylate cyclase, such as, in particular, the compounds described in WO 01/19355, WO 01/19776, WO 01/19778, WO 01/19780, WO 02/070462 and WO 02/070510;
- inhibitors of human neutrophil elastase (HNE), such as, for example, sivelestat and DX-890 (Reltran);
- compounds which inhibit the signal transduction cascade, such as, for example, tyrosine-kinase inhibitors, in particular sorafenib, imatinib, gefitinib and erlotinib; and/or
- compounds which modulate the energy metabolism of the heart, such as, for example, etomoxir, dichloroacetate, ranolazine and trimetazidine.

Lipid metabolism-modifying active ingredients are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists, PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, dalcetrapib, BAY 60-5521, anacetrapib or CETP vaccine (CETi-1).

In a preferred embodiment of the invention, the compounds according to the invention are administered in combination with a PPAR-γ agonist for example from the class of the thiazolidinediones, such as, by way of example and by way of preference, pioglitazone or rosiglitazone.

In a preferred embodiment of the invention, the compounds according to the invention are administered in combination with a PPAR-δ agonist such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients preferably include sulfonylureas, biguanides, meglitinide derivatives, glucosidase inhibitors and PPAR-gamma agonists.

In a preferred embodiment of the invention, the compounds according to the invention are administered in combination with insulin.

In a preferred embodiment of the invention, the compounds according to the invention are administered in combination with a sulfonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a DPP-IV inhibitor, such as, by way of example and by way of preference, sitagliptin and vildagliptin.

In a preferred embodiment of the invention, the compounds according to the invention are administered in combination with a PPAR-gamma agonist, for example from the class of the thiazolindiones, such as, by way of example and by way of preference, pioglitazone and rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, olmesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the compounds according to the invention are administered in combination with an aldosterone or mineralocorticoid receptor antagonist, such as, by way of example and by way of preference, spironolactone or eplerenone.

In a preferred embodiment of the invention, the compounds according to the invention are administered in combination with a vasopressin receptor antagonist, such as, by way of example and by way of preference, conivaptan, tolvaptan, lixivaptan or SR-121463.

In a preferred embodiment of the invention, the compounds according to the invention are administered in combination with an organic nitrate or NO donor, such as, by way of example and by way of preference, sodium nitroprusside, nitroglycerol, isosorbide mononitrate, isosorbide dinitrate, molsidomin or SIN-1, or in combination with inhalative NO.

In a preferred embodiment of the invention, the compounds according to the invention are administered in combination with a positive-inotropic compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the compounds according to the invention are administered in combination with antisympathotonics, such as reserpine, clonidine or alphamethyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, dabigatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

In the context of the present invention, particular preference is given to combinations comprising at least one of the compounds according to the invention and also one or more further active ingredients selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prophylaxis of the disorders mentioned above.

The present invention furthermore provides medicaments comprising at least one compound according to the invention, usually together with one or more inert, nontoxic, pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert, non-toxic, pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active ingredient, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

Abbreviations Used aq. aqueous
Ex. Example
c concentration
d doublet (in NMR)
dd doublet of doublets (in NMR)
DBU 1,8-diazabicyclo[5.4.0]undec-7-ene
TLC thin-layer chromatography
DCI direct chemical ionization (in MS)
DMF N,N-dimethylformamide
DMSO dimethyl sulfoxide
EDC N'-(3-dimethylaminopropyl)-N-ethylcarbodiimide hydrochloride
ee enantiomeric excess
EI electron impact ionization (in MS)
ESI electrospray ionization (in MS)
Et ethyl
h hour(s)
HATU O-(7-azabenzotriazol-1-yl)-N,N,N',N'-tetramethyluronium hexafluorophosphate
HOBT 1-hydroxy-1H-benzotriazole hydrate HPLC high-pressure, high-performance liquid chromatography
conc. concentrated
LC-MS liquid chromatography-coupled mass spectrometry
lit. literature (reference)
Me methyl
MeCN acetonitrile
min minute(s)
MS mass spectrometry
NMM N-methylmorpholine
NMR nuclear magnetic resonance spectrometry
q quartet (in NMR)
rac. racemic
RP-HPLC reversed-phase HPLC
RT room temperature
$R_t$ retention time (in HPLC)
s singlet (in NMR)
s br broad singlet (in NMR)
t triplet (in NMR)
t-Bu tert-butyl
TFA trifluoroacetic acid
THF tetrahydrofuran
dil. dilute
HPLC, LC-MS and GC-MS Methods:
Method 1 (LC-MS):
 MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.
Method 2 (LC-MS):
 MS instrument type: Micromass ZQ; HPLC instrument type: HP 1100 Series; UV DAD; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.
Method 3 (LC-MS):
 MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.
Method 4 (LC-MS):
 MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.
Method 5 (LC-MS):
 Instrument: Micromass Quattro LCZ with HPLC Agilent Series 1100; column: Phenomenex Onyx Monolithic C18, 100 mm×3 mm. mobile phase A: 1 l of water+0.5 ml 50% strength formic acid, mobile phase B: 1 l of acetonitrile+0.5 ml 50% strength formic acid; gradient: 0.0 min 90% A→2 min 65% A→4.5 min 5% A→6 min 5% A; flow rate: 2 ml/min; oven: 40° C.; UV detection: 208-400 nm.
Method 6 (LC-MS):
 Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A oven: 50° C.; flow rate: 0.33 ml/min; UV detection: 210 nm.
Method 7 (LC-MS):
 Instrument: Micromass Quattro LCZ with HPLC Agilent Series 1100; column: Phenomenex Synergi 2μ Hydro-RP Mercury 20 mm×4 mm; mobile phase A: 1 l of water+0.5 ml 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.
Method 8 (LC-MS):
 MS instrument type: Waters (Micromass) Quattro Micro; HPLC instrument type: Agilent 1100 Series; column: Thermo Hypersil GOLD 3μ 20×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A; oven: 50° C.; flow rate: 2 ml/min; UV detection: 210 nm
Method 9 (LC-MS):
 MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.
Method 10 (LC-MS):
 Instrument: Micromass Quattro LCZ with HPLC Agilent Series 1100; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.
Method 11 (LC-MS):
 MS instrument: Waters ZQ 2000; HPLC instrument: Agilent 1100, 2-column arrangement, autosampler: HTC PAL; column: YMC-ODS-AQ, 50 mm×4.6 mm, 3.0 μm; mobile phase A: water+0.1% formic acid, mobile phase B: acetonitrile+0.1% formic acid; gradient: 0.0 min 100% A-0.2 min 95% A-1.8 min 25% A-1.9 min 10% A-2.0 min 5% A-3.2 min 5% A-3.21 min 100% A-3.35 min 100% A; oven: 40° C.; flow rate: 3.0 ml/min; UV detection: 210 nm.
Method 12 (DCI-MS):
 Instrument: DSQ II; Thermo Fisher-Scientific; DCI with $NH_3$, flow rate: 1.1 ml/min; source temperature: 200° C.; ionizing energy 70 eV; DCI heating filament heated to 800° C.; mass range 80-900.

Starting Materials and Intermediates

Example 1A 1-(4-{[(2S)-2-{[tert-Butyl(dimethyl)silyl]oxy}propyl]oxy}phenyl)ethanone

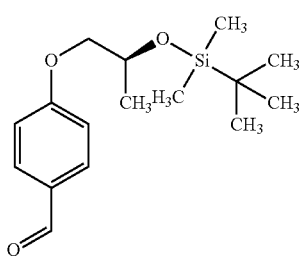 [SMILES: C[C@@H](COc1ccc(C=O)cc1)O[Si](C)(C)C(C)(C)C]

The preparation was carried out as described in WO 2009/015776 for Example 6A.

Yield: (50% of theory)

LC-MS (Method 7): $R_t$=3.30 min; MS (ESIpos): m/z=295 [M+H]$^+$.

$^1$H NMR (400 MHz, DMSO-d$_6$): δ=7.82 (d, 2H), 7.07 (d, 2H), 4.18-4.11 (m, 1H), 3.98 (dd, 1H), 3.87 (dd, 1H), 1.13 (d, 3H), 0.81 (s, 9H), 0.3 (s, 3H), 0.1 (s, 3H).

The product contains about 10% of the regioisomer 4-[(1S)-2-{[tert-butyl(dimethyl)silyl]oxy}-1-methylethoxy]benzaldehyde.

Example 2A

4-{[(4S)-2,2-Dimethyl-1,3-dioxolan-4-yl]methoxy}benzaldehyde

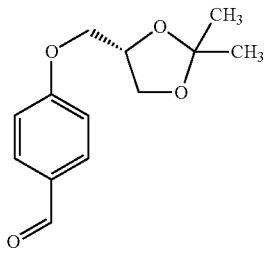 [SMILES: CC1(C)OC[C@H](COc2ccc(C=O)cc2)O1]

The preparation was carried out as described in WO 2009/015776 for Example 9A.

Yield: (79% of theory)

LC-MS (Method 1): $R_t$=1.77 min; MS (ESIpos): m/z=237 [M+H]$^+$.

$^1$H NMR (400 MHz, DMSO-d$_6$): δ=9.89 (s, 1H), 7.85 (d, 2H), 7.03 (d, 2H), 4.50 (q, 1H), 4.22-4.09 (m, 2H), 4.04 (dd, 1H), 3.92 (dd, 1H), 1.48 (s, 3H), 1.41 (s, 3H).

Example 3A

4-Formylphenyl dimethylsulfamate

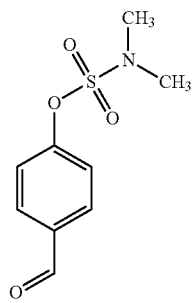

The preparation was carried out as described in the patent DE 1016256 (Farbenfabrik Bayer).

Example 4A

4-[(1R)-2-Hydroxy-1-methylethoxy]benzaldehyde

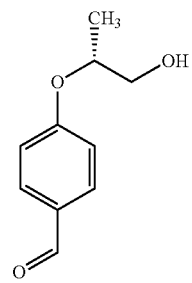

Under argon, 785 mg (6.43 mmol) of 4-hydroxybenzaldehyde and 759 mg (8.04 mmol) of (S)-(+)-2-chloro-1-propanol were initially charged in 15.7 ml of DMF. 2.04 g (19.3 mmol) of sodium carbonate were added, and the mixture was then stirred at 130° C. for 20 h. The reaction mixture was purified by preparative HPLC (Chromasil, water/acetonitrile).

Yield: 755 mg (65% of theory)

LC-MS (Method 2): $R_t$=1.58 min; MS (ESIpos): m/z=181 [M+H]$^+$.

Example 5A tert-Butyl [2-(4-formylphenoxy)ethyl]carbamate

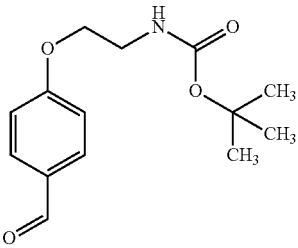 [SMILES: CC(C)(C)OC(=O)NCCOc1ccc(C=O)cc1]

2.54 g (20.81 mmol) of 4-hydroxybenzaldehyde were initially charged in 50 ml of DMF. 5.13 g (22.89 mmol) of tert-butyl (2-bromoethyl)carbamate, 10.17 g (31.25 mmol) of cesium carbonate and 0.78 g (5.20 mmol) of sodium iodide were added, and the mixture was then stirred at 65° C. overnight. Water was added, and the reaction mixture was extracted three times with ethyl acetate. The combined organic phases were washed in each case twice with 1N aqueous sodium hydroxide solution, saturated aqueous ammonium chloride solution and water, dried over sodium sulfate, filtered and concentrated.

Yield: 5 g (90% of theory)

LC-MS (Method 3): $R_t$=2.10 min; MS (ESIpos): m/z=210 [M+H—$C_4H_8$]$^+$.

$^1$H NMR (400 MHz, DMSO-$d_6$): δ=9.87 (s, 1H), 7.86 (d, 2H), 7.12 (d, 2H), 7.07-7.02 (m, 1H), 4.08 (t, 2H), 3.35-3.31 (m, 2H), 1.38 (s, 9H).

Example 6A 4-(Methylamino)benzenecarbaldehyde

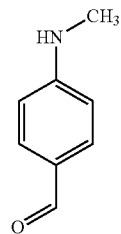

The preparation was carried out as described in U.S. Pat. No. 4,317,914 A1 (page Example).

Example 7A 6-(2-Hydroxyethoxy)pyridine-3-carbaldehyde

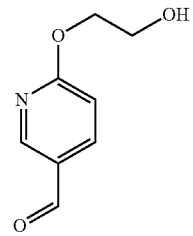 [SMILES: O=Cc1ccc(OCCO)nc1]

The preparation was carried out as described in WO 2008/028590 for Example 1A.

Yield: (46% of theory, 77% pure)

LC-MS (Method 2): $R_t$=1.09 min; MS (ESIpos): m/z=168 [M+H]$^+$.

$^1$H NMR (300 MHz, DMSO-$d_6$): δ=9.97 (s, 1H), 8.76 (d, 1H), 8.11 (d, 1H), 6.99 (d, 1H), 4.90 (t, 1H), 4.40 (t, 2H), 3.73 (dt, 2H).

Example 8A 4-(2-Hydroxy-2-methylpropoxy)benzenecarbaldehyde

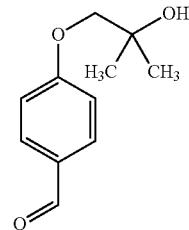

5 g (40.94 mmol) of 4-hydroxybenzaldehyde were initially charged in 50 ml of DMF. 4.45 g (40.94 mmol) of 1-chloro-2-methylpropan-2-ol and 6.08 g (57.32 mmol) of sodium carbonate were added, and the mixture was then stirred at 130° C. overnight. Saturated aqueous sodium bicarbonate solution/ethyl acetate were added to the reaction mixture. The precipitate was filtered off and discarded. The two phases were separated from one another, and the aqueous phase was extracted three times with ethyl acetate. The combined organic phases were dried over magnesium sulfate, filtered and concentrated using a rotary evaporator. The residue was purified by column chromatography on silica gel 60 (mobile phase: cyclohexane/ethyl acetate 5/1→1/2).

Yield: 8.6 g (82% of theory, 76% pure)

LC-MS (Method 4): $R_t$=1.17 min; MS (ESIpos): m/z=195 [M+H]$^+$.

$^1$H NMR (400 MHz, DMSO-$d_6$): δ=9.87 (s, 1H), 7.86 (d, 2H), 7.12 (d, 2H), 4.70 (s, 1H), 3.84 (s, 2H), 1.21 (s, 6H).

Example 9A 4-(2-Methoxyethoxy)benzenecarbaldehyde

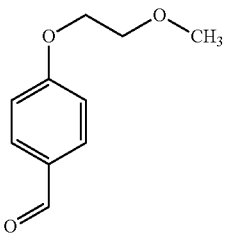

The preparation was carried out as described in WO 03/053441 for Example 1 (step 1).

Example 10A

2-Amino-4-[4-(2-hydroxyethoxy)phenyl]-6-sulfanylpyridine-3,5-dicarbonitrile

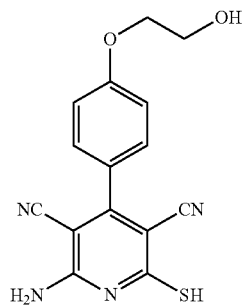

The preparation was carried out as described in WO 03/053441 for Example 6 (step 1).

LC-MS (Method 5): $R_t$=1.73 min; MS (ESIpos): m/z=313 [M+H]$^+$.

Example 11A

2-Amino-4-(3-fluorophenyl)-6-sulfanylpyridine-3,5-dicarbonitrile

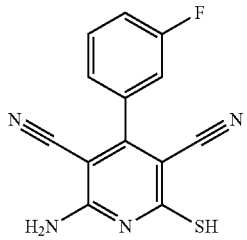 [SMILES: N#Cc1c(N)nc(S)c(C#N)c1-c1cccc(F)c1]

2 g (5.77 mmol) of 2-amino-4-(3-fluorophenyl)-6-(phenylsulfanyl)pyridine-3,5-dicarbonitrile (Example 37A) were initially charged in 20 ml of DMF. 1.58 g (20.21 mmol) of sodium sulfide were added, and the mixture was stirred at 80° C. for 2 h and stirred further at RT overnight. 10 ml of 1N hydrochloric acid were added to the reaction mixture, and the precipitate was filtered off, washed with water and dried under high vacuum. In addition, more solid precipitated from the filtrate overnight, and this solid was filtered off and washed with water. Once more, this gave the desired solid.

Yield: 2.08 g (84% of theory, 63% pure)

LC-MS (Method 5): $R_t$=2.54 min; MS (ESIpos): m/z=271 [M+H]$^+$.

Example 12A

4-Phenyl-2-sulfanylpyridine-3,5-dicarbonitrile

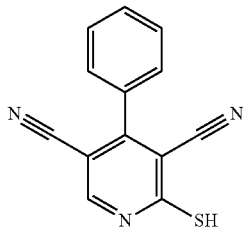 [SMILES: N#Cc1cnc(S)c(C#N)c1-c1ccccc1]

918 mg (2.928 mmol) of 4-phenyl-2-(phenylsulfanyl)pyridine-3,5-dicarbonitrile (Example 36A) were initially charged in 10.7 ml of DMF. 274 mg (3.514 mmol) of sodium sulfide were added, and the reaction solution was then stirred at 80° C. for 3 h, and after 1.5 h another 274 mg (3.514 mmol) of sodium sulfide were added. The mixture was stirred at RT overnight. 5.85 ml of 1N hydrochloric acid were added to the reaction mixture, and the reaction solution was evaporated. 5 ml of tetrahydrofuran were added to the residue, and the precipitate formed was filtered off and discarded. The filtrate was purified by preparative HPLC (Chromasil, water/acetonitrile).

Yield: 511 mg (73% of theory)

LC-MS (Method 4): $R_t$=1.45 min; MS (ESIpos): m/z=238 [M+H]$^+$.

Example 13A

4-[4-(2-Hydroxyethoxy)phenyl]-2-sulfanylpyridine-3,5-dicarbonitrile

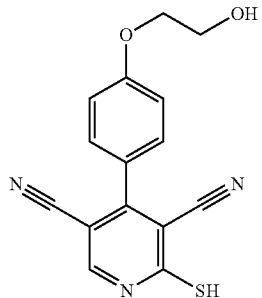 [SMILES: N#Cc1cnc(S)c(C#N)c1-c1ccc(OCCO)cc1]

0.1 g (0.268 mmol) of 4-[4-(2-hydroxyethoxy)phenyl]-2-(phenylthio)pyridine-3,5-dicarbonitrile (Example 47A) was initially charged in 1 ml of DMF. 73 mg (0.937 mmol) of sodium sulfide were added, and the mixture was then stirred at 80° C. for 2 h and stirred further at RT overnight. 20 ml of 1N hydrochloric acid were added, and the residue was filtered off and washed thoroughly with water.

Yield: 75 mg (95% of theory)

LC-MS (Method 5): $R_t$=1.93 min; MS (ESIpos): m/z=298 [M+H]$^+$.

Example 14A 4-(4-Methoxyphenyl)-2-sulfanylpyridine-3,5-dicarbonitrile

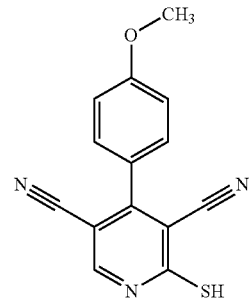 [SMILES: COc1ccc(-c2c(C#N)cnc(S)c2C#N)cc1]

1.3 g (3.028 mmol) of 4-(4-methoxyphenyl)-2-(phenylsulfanyl)pyridine-3,5-dicarbonitrile (Example 48A) were initially charged in 11 ml of DMF. 284 mg (3.634 mmol) of sodium sulfide were added, and the mixture was then stirred at 80° C. for 2 h and stirred further at RT overnight. 6 ml of 1N hydrochloric acid were added to the reaction mixture, and the reaction solution was evaporated. The residue was purified by preparative HPLC (Chromasil, water/acetonitrile).

Yield: 385 mg (48% of theory)

LC-MS (Method 6): $R_t$=0.94 min; MS (ESIpos): m/z=268 [M+H]$^+$.

Example 15A

2-Amino-4-[4-(2-methoxyethoxy)phenyl]-6-sulfanylpyridine-3,5-dicarbonitrile

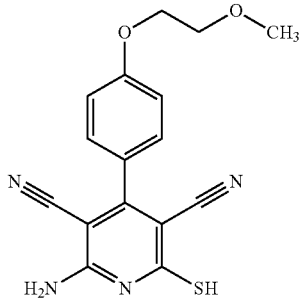 [SMILES: COCCOc1ccc(-c2c(C#N)c(N)nc(S)c2C#N)cc1]

The preparation was carried out as described in WO 03/053441 for Example 1/2nd step.

Example 16A

2-Amino-6-sulfanyl-4-[4-(2,2,2-trifluoroethoxy)phenyl]pyridine-3,5-dicarbonitrile

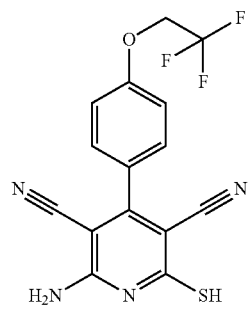 [SMILES: N#Cc1c(N)nc(S)c(C#N)c1-c1ccc(OCC(F)(F)F)cc1]

5 g (24.492 mmol) of 4-(2,2,2-trifluoroethoxy)benzaldehyde and 5.15 g (51.434 mmol) of cyanothioacetamide were initially charged in 100 ml of ethanol. 5.2 g (51.434 mmol) of 4-methylmorpholine were added, and the reaction solution was then stirred under RF for 4 h. A dark-red solution was formed, which was stirred ar RT for 20 h. A precipitate was formed, which was filtered off and washed with ethanol.

Yield: 2.9 g (33% of theory, 97% pure)

LC-MS (Method 1): $R_t$=1.90 min; MS (ESIpos): m/z=351 [M+H]$^+$.

The examples listed in Table 1 were prepared analogously to Example 16A from the appropriate starting materials.

TABLE 1

| Example No. | Structure | LC-MS: $R_t$ [min] (Method); MS (ESI): m/z [M + H]$^+$ |
|---|---|---|
| 17A | | 1.50 min (Method 6); m/z = 441 |
| 18A | | 1.75 min (Method 1); m/z = 383 |
| 19A | 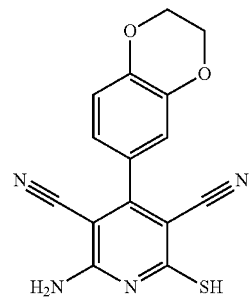 | 1.29 min (Method 4); m/z = 311 |
| 20A | 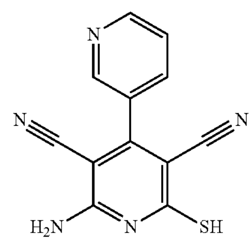 [SMILES: N#Cc1c(N)nc(S)c(C#N)c1-c1cccnc1] | 0.75 min (Method 4); m/z = 254 |
| 21A | 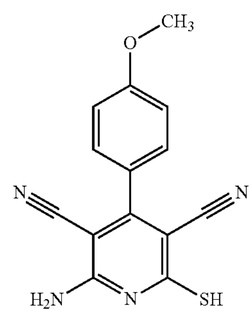 [SMILES: COc1ccc(-c2c(C#N)c(N)nc(S)c2C#N)cc1] | 1.82 min (Method 3); m/z = 283 |
| 22A | 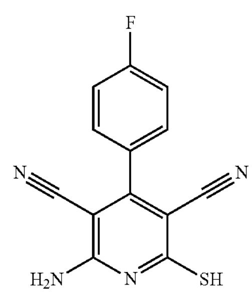 [SMILES: N#Cc1c(N)nc(S)c(C#N)c1-c1ccc(F)cc1] | 2.56 min (Method 5); m/z = 271 |
| 23A | 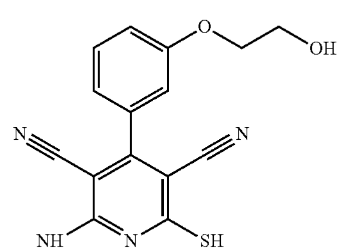 [SMILES: N#Cc1c(N)nc(S)c(C#N)c1-c1cccc(OCCO)c1] | 1.50 min (Method 3); m/z = 313 |

TABLE 1-continued

| Example No. | Structure | LC-MS: R$_t$ [min] (Method); MS (ESI): m/z [M + H]$^+$ |
|---|---|---|
| 24A | 2-amino-4-(pyridin-2-yl)-6-mercaptopyridine-3,5-dicarbonitrile *1 | 1.30 min (Method 3); m/z = 254 |
| 25A | 2-amino-4-[4-((S)-1-hydroxypropan-2-yloxy)phenyl]-6-mercaptopyridine-3,5-dicarbonitrile *2 | 1.54 min (Method 7); m/z = 327 |
| 26A | 2-amino-4-[4-(2-(tert-butoxycarbonylamino)ethoxy)phenyl]-6-mercaptopyridine-3,5-dicarbonitrile | 1.64 min (Method 4); m/z = 412 |
| 27A | 2-amino-4-(4-ethoxyphenyl)-6-mercaptopyridine-3,5-dicarbonitrile | 1.49 min (Method 4); m/z = 297 |
| 28A | 2-amino-4-(4-fluoro-3-methoxyphenyl)-6-mercaptopyridine-3,5-dicarbonitrile | 1.40 min (Method 4); m/z = 301 |
| 29A | 2-amino-4-(4-(methylamino)phenyl)-6-mercaptopyridine-3,5-dicarbonitrile | 1.19 min (Method 4); m/z = 282 |
| 30A | 2-amino-4-phenyl-6-mercaptopyridine-3,5-dicarbonitrile | 1.73 min (Method 3); m/z = 253 |
| 31A | 2-amino-4-(6-(2-hydroxyethoxy)pyridin-3-yl)-6-mercaptopyridine-3,5-dicarbonitrile | 1.39 min (Method 3); m/z = 314 |
| 32A | 2-amino-4-(4-(2-hydroxy-2-methylpropoxy)phenyl)-6-mercaptopyridine-3,5-dicarbonitrile *3 | 0.84 min (Method 6); m/z = 341 |

TABLE 1-continued

| Example No. | Structure | LC-MS: $R_t$ [min] (Method); MS (ESI): m/z [M + H]+ |
|---|---|---|
| 33A | 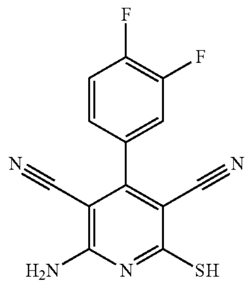 [SMILES: N#Cc1c(N)nc(S)c(C#N)c1-c1ccc(F)c(F)c1] | 2.00 min (Method 3); m/z = 289 |

*1 Different work-up; the reaction mixture was evaporated.
*2 Different work-up; the reaction mixture was evaporated. The residue was purified by preparative HPLC (Chromasil, water/acetonitrile + 0.3% conc. hydrochloric acid).
*3 Different work-up, the reaction mixture was evaporated. The residue was purified by column chromatography on silica gel 60 (mobile phase: dichloromethane/methanol 40/1 → 4/1).

Example 34A

2-Amino-4-(4-fluoro-3-methoxyphenyl)-6-(phenyl-sulfanyl)pyridine-3,5-dicarbonitrile

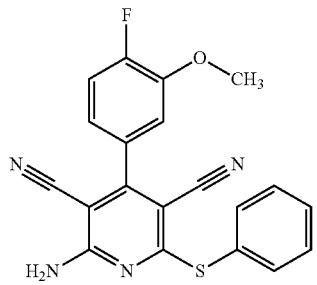 [SMILES: COc1cc(-c2c(C#N)c(N)nc(Sc3ccccc3)c2C#N)ccc1F]

25 g (162.19 mmol) of 4-fluoro-3-methoxybenzenecarbaldehyde, 21.43 g (324.38 mmol) of malononitrile and 17.87 g (162.19 mmol) of thiophenol were dissolved in 300 ml of ethanol. 0.076 g (0.72 mmol) of triethylamine was added, and the mixture was then heated at reflux overnight. After cooling to RT, the precipitate formed was filtered off and washed with cold ethanol.

Yield: 15.84 g (25% of theory, 95% pure)

LC-MS (Method 6): $R_t$=1.29 min; MS (ESIpos): m/z=377 [M+H]+.

The examples listed in Table 2 were prepared analogously to Example 34A from the appropriate starting materials.

TABLE 2

| Example No. | Structure | LC-MS: $R_t$ [min] (Method); MS (ESI): m/z [M + H]+ |
|---|---|---|
| 35A | 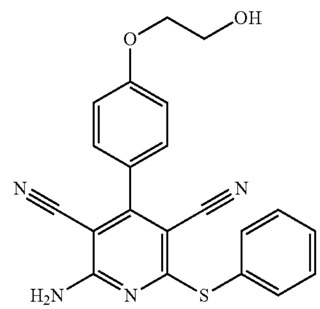 [SMILES: N#Cc1c(N)nc(Sc2ccccc2)c(C#N)c1-c1ccc(OCCO)cc1] | 2.22 min (Method 3); m/z = 389 |
| 36A | 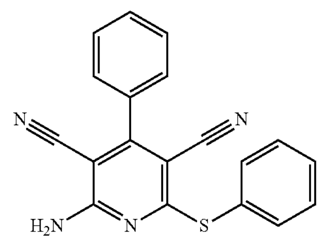 [SMILES: N#Cc1c(N)nc(Sc2ccccc2)c(C#N)c1-c1ccccc1] | 2.06 min (Method 4); m/z = 329 |
| 37A | 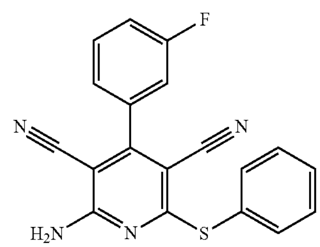 [SMILES: N#Cc1c(N)nc(Sc2ccccc2)c(C#N)c1-c1cccc(F)c1] | 2.11 min (Method 4); m/z = 347 |
| 38A | 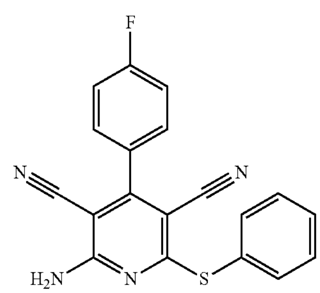 [SMILES: N#Cc1c(N)nc(Sc2ccccc2)c(C#N)c1-c1ccc(F)cc1] | 1.29 min (Method 6); m/z = 347 |
| 39A | 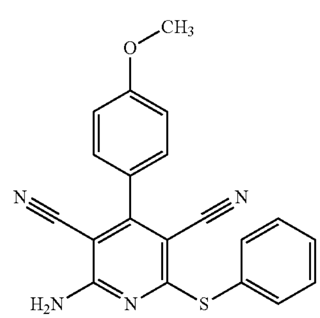 [SMILES: COc1ccc(-c2c(C#N)c(N)nc(Sc3ccccc3)c2C#N)cc1] | 1.27 min (Method 6); m/z = 359 |

Example 40A

4-(Hydroxymethyl)-N-methylpyridine-2-carboxamide hydrochloride hydrate

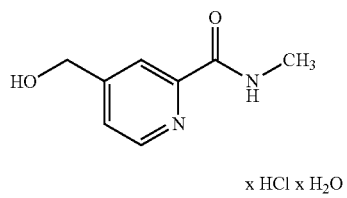

x HCl x H$_2$O

The preparation was carried out as described in U.S. Pat. No. 6,689,883 for Example XX.

Example 41A

4-(Chloromethyl)-N-methylpyridine-2-carboxamide hydrochloride

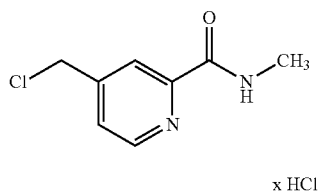

x HCl 10 g (45.32 mmol) of 4-(hydroxymethyl)-N-methylpyridine-2-carboxamide (Example 40A) were suspended in 160 ml of dichloromethane and cooled to 0° C. 16.18 g (135.96 mmol) of thionyl chloride were added, and the reaction mixture was then warmed to RT and stirred at RT overnight. The reaction mixture was evaporated and dried under high vacuum.

Yield: 10 g (100% of theory)

LC-MS (Method 6): $R_t$=0.71 min; MS (ESIpos): m/z=185 [M+H]$^+$.

$^1$H NMR (400 MHz, DMSO-d$_6$): δ=8.85-8.78 (m, 1H), 8.65 (d, 1H), 8.10 (s, 1H), 7.64 (d, 1H), 4.90 (s, 2H), 2.83 (d, 3H).

Example 42A

4-Formyl-N-methylpyridine-2-carboxamide

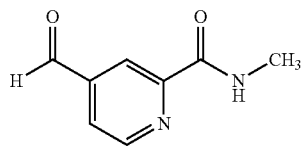

7.50 g (33.989 mmol) of 4-(hydroxymethyl)-N-methylpyridine-2-carboxamide hydrochloride hydrate (Example 40A) were initially charged in 90 ml of methanol, 23.64 g (271.915 mmol) of manganese dioxide were added and the mixture was stirred at RT overnight. The reaction mixture was filtered off with suction through silica gel, the silica gel/manganese dioxide mixture was stirred with tetrahydrofuran/methanol 1:1 overnight, the silica gel/manganese dioxide mixture was then filtered off and the filtrate was evaporated.

Yield: 4.08 g (73% of theory)

LC-MS (Method 8): $R_t$=0.99 min; MS (ESIpos): m/z=165 [M+H]$^+$.

Example 43A rac-4-(1-Hydroxyethyl)-N-methylpyridine-2-carboxamide

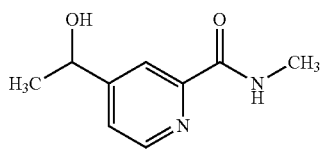

At 0° C. and under argon, 393 mg (2.394 mmol) of 4-formyl-N-methylpyridine-2-carboxamide Example 42A were initially charged in 66 ml abs. tetrahydrofuran. At 0° C., 343 mg (2.873 mmol) of methylmagnesium bromide [1.4 mol in toluene/tetrahydrofuran 3/1] were added dropwise, and the reaction solution was stirred at this temperature for 1 h. 200 μl of semisaturated aqueous sodium bicarbonate solution and 200 ml of ethyl acetate were added to the reaction solution. The precipitate was filtered off and washed with ethyl acetate. The filtrate was evaporated.

Yield: 107 mg (72% of theory)

LC-MS (Method 6): $R_t$=0.37 min; MS (ESIpos): m/z=181 [M+H]$^+$.

Example 44A rac-4-(1-Chloroethyl)-N-methylpyridine-2-carboxamide trifluoroacetate

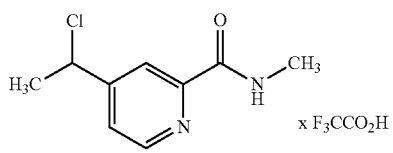

x F$_3$CCO$_2$H 85 mg (0.472 mmol) of rac-4-(1-hydroxyethyl)-N-methylpyridine-2-carboxamide (Example 43A) were initially charged in 2 ml of dichloromethane. At 0° C., 168 mg (1.417 mmol) of thionyl chloride were added dropwise to the reaction solution, and the mixture was stirred at RT for 2.5 h.

The reaction solution was evaporated. The residue was purified by preparative HPLC (Chromasil, water/acetonitrile+0.15% trifluoroacetic acid).

Yield: 27 mg (18% of theory)

LC-MS (Method 4): $R_t$=1.24 min; MS (ESIpos): m/z=199 [M+H-trifluoroacetic acid]$^+$.

Example 45A tert-Butyl (2-{4-[2-amino-3,5-dicyano-6-({[2-(methylcarbamoyl)pyridin-4-yl]methyl}sulfanyl)-pyridin-4-yl]phenoxy}ethyl)carbamate

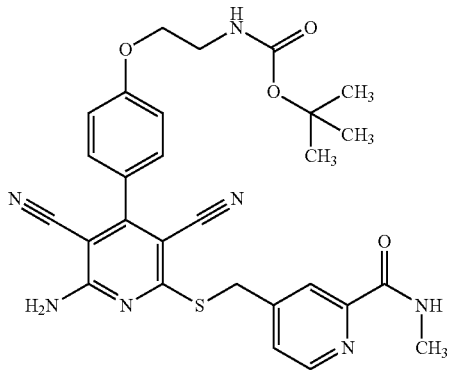 [SMILES: CNC(=O)c1cc(CSc2nc(N)c(C#N)c(-c3ccc(OCCNC(=O)OC(C)(C)C)cc3)c2C#N)ccn1]

765 mg (1.86 mmol) of tert-butyl {2-[4-(2-amino-3,5-dicyano-6-sulfanylpyridine-4-yl)phenoxy]ethyl}carbamate (Example 26A), 452 mg (2.05 mmol) of 4-(chloromethyl)-N-methylpyridine-2-carboxamide hydrochloride (Example 41A) and 469 mg (5.58 mmol) of sodium bicarbonate were dissolved in 12 ml of DMF, and the mixture was stirred at RT for 2 h. The reaction mixture was evaporated. The residue was purified by preparative HPLC (Chromasil, water/acetonitrile+0.1% trifluoroacetic acid).

Yield: 480 mg (40% of theory)

LC-MS (Method 6): $R_t$=1.21 min; MS (ESIpos): m/z=460 [M+H-BOC]$^+$.

Example 46A

4-Phenyl-2-(phenylsulfanyl)pyridine-3,5-dicarbonitrile

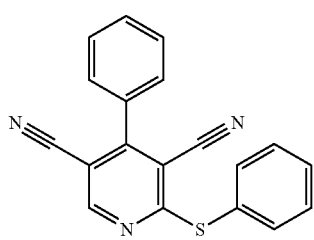 [SMILES: N#Cc1cnc(Sc2ccccc2)c(C#N)c1-c1ccccc1]

1.5 g (4.568 mmol) of Example 36A were initially charged in 20 ml of tetrahydrofuran. 61 mg (0.457 mmol) of copper (II) chloride and 1.6 g (13.703 mmol) of isopentyl nitrite were added, and the reaction solution was stirred at RT overnight. During the first 8 hours, six times in each case 61 mg (0.457 mmol) of copper(II) chloride were added to the reaction solution. 9.1 ml of 1N hydrochloric acid were added, and the reaction solution mixture was extracted three times with ethyl acetate. The combined organic phases were washed once with saturated aqueous sodium chloride solution and then dried over sodium sulfate, filtered and evaporated. The residue was purified by column chromatography on silica gel 60 (mobile phase: toluene/ethyl acetate 50/1→20/1).

Yield: 0.4 g (27% of theory)

LC-MS (Method 4): $R_t$=2.25 min; MS (ESIpos): m/z=314 [M+H]$^+$.

Example 47A

4-[4-(2-Hydroxyethoxy)phenyl]-2-(phenylsulfanyl)pyridine-3,5-dicarbonitrile

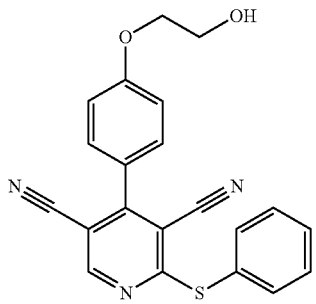 [SMILES: N#Cc1cnc(Sc2ccccc2)c(C#N)c1-c1ccc(OCCO)cc1]

5 g (12.872 mmol) of Example 35A were initially charged in 60 ml of tetrahydrofuran. 173 mg (1.287 mmol) of copper (II) chloride and 4.5 g (38.615 mmol) of isopentyl nitrite were added, and the reaction solution was then stirred at RT overnight. During the first 8 hours, four times in each case 173 mg (1.287 mmol) of copper(II) chloride were added to the reaction solution. 25.7 ml of 1N hydrochloric acid were added, and the reaction solution mixture was extracted twice with ethyl acetate. The combined organic phases were washed in each case once with saturated aqueous sodium chloride solution and saturated aqueous sodium chloride solution and then dried over sodium sulfate, filtered and evaporated. The residue was purified by column chromatography on silica gel 60 (mobile phase: toluene/ethyl acetate 50/1→1/1).

Yield: 1.43 g (27% of theory)

LC-MS (Method 4): $R_t$=1.95 min; MS (ESIpos): m/z=374 [M+H]$^+$.

Example 48A 4-(4-Methoxyphenyl)-2-(phenylsulfanyl)pyridine-3,5-dicarbonitrile

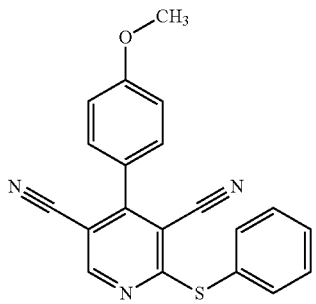 [SMILES: COc1ccc(-c2c(C#N)cnc(Sc3ccccc3)c2C#N)cc1]

3 g (8.368 mmol) of Example 39A were initially charged in 39 ml of tetrahydrofuran. 113 mg (0.837 mmol) of copper(II) chloride and 2.94 g (25.104 mmol) of isopentyl nitrite were added, and the reaction solution was then stirred at RT for 2 days. During the first day, four times in each case 113 mg (0.837 mmol) of copper(II) chloride and during the second day two times in each case 226 mg (1.674 mmol) of copper(II) chloride were added to the reaction solution. 16.7 ml of 1N hydrochloric acid were added, and the reaction solution mixture was extracted twice with ethyl acetate. The combined organic phases were washed in each case once with saturated aqueous sodium chloride solution and saturated aqueous sodium chloride solution and then dried over sodium sulfate, filtered and evaporated. The residue was purified by column chromatography on silica gel 60 (mobile phase: toluene/ethyl acetate 10/1).

Yield: 1.04 g (36% of theory)

LC-MS (Method 3): $R_t$=2.77 min; MS (ESIpos): m/z=344 [M+H]$^+$.

Example 49A 3-(Chloromethyl)-N-methylbenzenecarboxamide

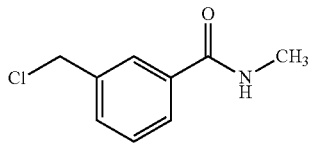

5 g (29.31 mmol) of 3-chloromethylbenzoic acid were suspended in 20 ml of abs. toluene, 5.23 g (43.96 mmol) of thionyl chloride were added dropwise and the mixture was stirred at 90° C. overnight. After cooling to RT, excess thionyl chloride and toluene were evaporated and the residue was dried under high vacuum for 1 h. Under argon, the residue was dissolved in 40 ml of abs. dichloromethane and cooled to 0° C., and 2.18 g (32.24 mmol) of methylamine hydrochloride were added. At 0° C., 7.58 g (58.62 mmol) of N,N-diisopropylethylamine were slowly added dropwise, and the reaction mixture was stirred at 0° C. for 15 min. 100 ml of dichloromethane were added, and the reaction mixture was washed three times with water and once with saturated aqueous sodium chloride solution. The organic phase was dried over sodium sulfate, filtered and concentrated using a rotary evaporator.

Yield: 5.28 (98% of theory)

LC-MS (Method 6): $R_t$=0.75 min; MS (ESIpos): m/z=184 [M+H]$^+$.

$^1$H NMR (400 MHz, DMSO-d$_6$): δ=8.53-8.45 (m, 1H), 7.91 (s, 1H), 7.79 (d, 1H), 7.58 (d, 1H), 7.47 (t, 1H), 4.81 (s, 2H), 2.78 (d, 3H).

Example 50A

Diethylpyridine 2,4-dicarboxylate

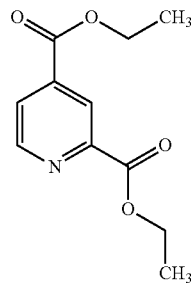 [SMILES: CCOC(=O)c1ccnc(C(=O)OCC)c1]

4.7 g (28.12 mmol) of 2,4-pyridinedicarboxylic acid and 8.02 g (42.19 mmol) of 4-toluenesulfonic acid monohydrate were suspended in 47 ml of toluene, the mixture was heated to 110° C. and 170 ml (2.87 mol) of ethanol were slowly added dropwise. The reaction mixture was stirred under reflux overnight. The reaction mixture was evaporated and the residue was purified by column chromatography on silica gel 60 (mobile phase: dichloromethane/ethanol 40/1→10/1).

Yield: 5.52 g (88% of theory)

LC-MS (Method 4): $R_t$=1.44 min; MS (ESIpos): m/z=224 [M+H]$^+$.

Example 51A

Ethyl 2-(cyclopropylcarbamoyl)pyridine-4-carboxylate

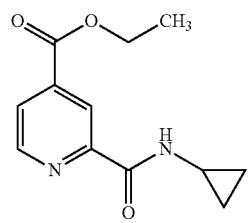 [SMILES: CCOC(=O)c1ccnc(C(=O)NC2CC2)c1]

5.5 g (24.64 mmol) of diethylpyridine 2,4-dicarboxylate (Example 50A) were dissolved in 55 ml of ethanol. 0.47 g (4.93 mmol) of magnesium chloride was added, and the mixture was then cooled to 0° C., 8.44 g (147.83 mmol) of cyclopropylamine were slowly added dropwise and the reaction mixture was stirred at 0° C. for 15 min and stirred further at RT for 2 days. The reaction mixture was evaporated. The residue was dissolved in water and extracted three times with ethyl acetate. The combined organic phases were dried over magnesium sulfate, filtered and concentrated using a rotary evaporator.

Yield: 5.45 g (91% of theory)

LC-MS (Method 8): $R_t$=1.65 min; MS (ESIpos): m/z=235 [M+H]$^+$.

Example 52A

N-Cyclopropyl-4-(hydroxymethyl)pyridine-2-carboxamide

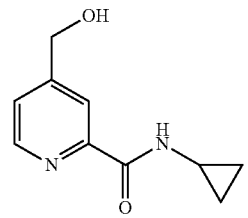 [SMILES: O=C(NC1CC1)c1cc(CO)ccn1]

5.45 g (23.27 mmol) of ethyl 2-(cyclopropylcarbamoyl)pyridine-4-carboxylate (Example 51A) and 1.55 g (13.96 mmol) of calcium chloride were dissolved in 56.6 ml of isopropanol and 5.7 ml of methanol. At RT, a solution of 4.6 ml of water, 0.1 g (1.16 mmol) of 45% strength sodium hydroxide solution and 1.06 g (27.92 mmol) of sodium borohydride were slowly added dropwise, and the reaction mixture was stirred at RT overnight. 10 ml of acetone were added, and the reaction mixture was stirred at RT for 2 h. The precipitate was filtered off and washed with isopropanol, and the filtrate was evaporated.

Yield: 5.1 g (90% of theory, 79% pure)

LC-MS (Method 3): $R_t$=0.93 min; MS (ESIpos): m/z=193 [M+H]$^+$.

Example 53A 4-(Chloromethyl)-N-cyclopropylpyridine-2-carboxamide

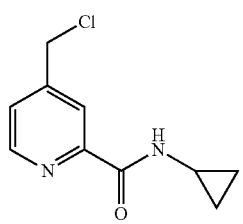 [SMILES: O=C(NC1CC1)c1cc(CCl)ccn1]

2.5 g (13.01 mmol) of N-cyclopropyl-4-(hydroxymethyl)pyridine-2-carboxamide (Example 52A) and 11.76 g (98.84 mmol) of thionyl chloride were combined and stirred at RT overnight. The reaction mixture was concentrated using a rotary evaporator. The residue was dissolved in ethyl acetate and washed once with saturated aqueous sodium bicarbonate solution. The organic phase was dried over magnesium sulfate, filtered and concentrated using a rotary evaporator. The residue was purified by column chromatography on silica gel 60 (mobile phase: cyclohexane/ethyl acetate 2/1).

Yield: 1.82 g (56% of theory, 84% pure)

LC-MS (Method 4): $R_t$=1.26 min; MS (ESIpos): m/z=211 [M+H]$^+$.

Example 54A 4-({[6-Amino-3,5-dicyano-4-(4-{[(4S)-2,2-dimethyl-1,3-dioxolan-4-yl]methoxy}phenyl)pyridin-2-yl]thio}methyl)-N-methylpyridine-2-carboxamide

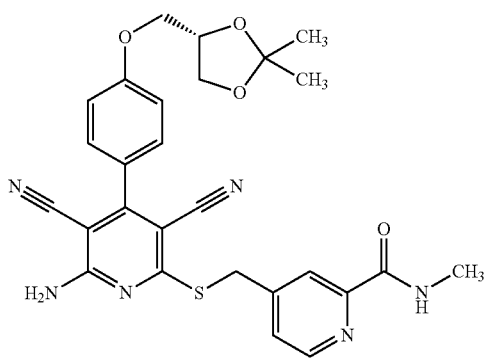 [SMILES: CNC(=O)c1cc(CSc2nc(N)c(C#N)c(-c3ccc(OC[C@H]4COC(C)(C)O4)cc3)c2C#N)ccn1]

450 mg (1.178 mmol) of 2-amino-4-(4-{[(4S)-2,2-dimethyl-1,3-dioxolan-4-yl]methoxy}phenyl)-6-mercaptopyridine-3,5-dicarbonitrile (Example 18A), 286 mg (1.29 mmol) of 4-(chloromethyl)-N-methylpyridine-2-carboxamide hydrochloride (Example 41A) and 395 mg (4.71 mmol) of sodium bicarbonate were dissolved in 7.1 ml of DMF and the mixture was stirred at RT for 1.5 h. Water was added to the reaction mixture. The precipitate was filtered off and washed with water.

Yield: 526 mg (83% of theory)

LC-MS (Method 4): $R_t$=1.89 min; MS (ESIpos): m/z=531 [M+H]$^+$.

The examples listed in Table 3 were prepared analogously to Example 54A from the appropriate starting materials.

TABLE 3

| Example No. | Structure (yield) | LC-MS: $R_t$ [min] (Method); MS (ESI): m/z [M + H]$^+$ |
|---|---|---|
| 55A | (58% of theory) *5 | 3.21 min (Method 3); m/z = 589 |
| 56A | *7 | 2.54 min (Method 3); m/z = 517 |

*5 Different procedure; reaction time overnight. After a reaction time of 18 h, another 0.3 eq of 4-(chloromethyl)-N-methylpyridine-2-carboxamide hydrochloride (Example 41A) was added, and the reaction mixture was stirred at room temperature for a further 2 h. Different work-up; the precipitate was filtered off. The residue was purified by preparative HPLC (Chromasil, water/acetonitrile).

*7 Different work-up; water was added to the reaction mixture until a clear solution had formed. The solution was purified by preparative HPLC (Chromasil, water/acetonitrile + 0.1% trifluoroacetic acid).

Example 57A tert-Butyl (2-{[(3-{[(6-amino-3,5-dicyano-4-phenylpyridin-2-yl)sulfanyl]methyl}phenyl)-carbonyl]amino}ethyl)carbamate

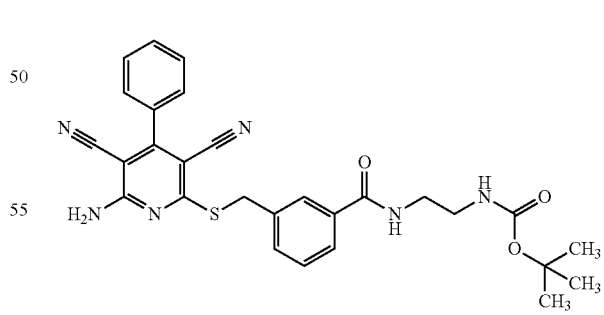

200 mg (0.52 mmol) of 3-{[(6-amino-3,5-dicyano-4-phenylpyridin-2-yl)sulfanyl]methyl}-benzenecarboxylic acid (Example 11) were charged in 5 ml of DMF. The reaction solution was cooled to 0° C. 393.58 mg (1.04 mmol) of HATU were added, and the mixture was then stirred at 0° C. for 20 min. 165.84 mg (1.04 mmol) of tert-butyl (2-aminoethyl)carbamate and 133.78 mg (1.04 mmol) of N,N-diisopropylethylamine were added, and the reaction solution was stirred at RT overnight. Water and tetrahydrofuran were added to the reaction mixture until a clear solution had formed. The solution was purified by preparative HPLC (Chromasil, water/acetonitrile+0.1% trifluoroacetic acid).

Yield: 260 mg (95% of theory)

LC-MS (Method 3): $R_t$=2.65 min; MS (ESIpos): m/z=529 [M+H]$^+$.

$^1$H NMR (400 MHz, DMSO-d$_6$): δ=8.45 (t, 1H), 8.35-8.00 (br s, 2H), 7.96 (s, 1H), 7.72 (t, 2H), 7.58-7.49 (m, 5H), 7.41 (t, 1H), 6.92 (t, 1H), 4.55 (s, 2H), 3.29 (q, 2H), 3.10 (q, 2H), 1.36 (s, 9H).

Example 58A tert-Butyl {(1S)-2-[(2-{4-[2-amino-3,5-dicyano-6-({[2-(methylcarbamoyl)pyridin-4-yl]-methyl}sulfanyl)pyridin-4-yl]phenoxy}ethyl)amino]-1-methyl-2-oxoethyl}carbamate

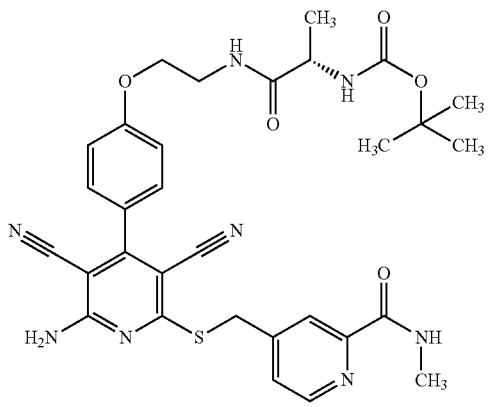 [SMILES: CNC(=O)c1cc(CSc2nc(N)c(C#N)c(-c3ccc(OCCNC(=O)[C@H](C)NC(=O)OC(C)(C)C)cc3)c2C#N)ccn1]

The preparation was carried out as described in Example 57A using the appropriate starting materials.

LC-MS (Method 4): $R_t$=1.74 min; MS (ESIpos): m/z=631 [M+H]$^+$.

Example 59A

Methyl 3-acetylbenzenecarboxylate

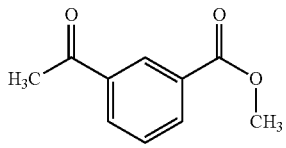

3.95 g (24.06 mmol) of 3-acetylbenzoic acid were initially charged in 100 ml of toluene and 75 ml of methanol. After dropwise addition of 4.12 g (36.09 mmol) of trimethylsilyldiazomethane 2M in diethyl ether at RT, an instant evolution of gas in the reaction solution was observed. Another 0.27 g (2.4 mmol) of trimethylsilyldiazomethane 2M in diethyl ether was added until the reaction solution remained yellow, and the mixture was stirred at RT for 10 min. The reaction solution was evaporated.

Yield: 4.28 g (100% of theory)

LC-MS (Method 4): $R_t$=1.38 min; MS (ESIpos): m/z=179 [M+H]$^+$.

Example 60A

Methyl 3-(1-hydroxyethyl)benzenecarboxylate

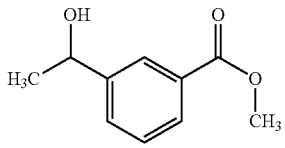

1.09 g (6.15 mmol) of methyl 3-acetylbenzenecarboxylate (Example 59A) were initially charged in 28 ml methanol. 0.77 g (12.29 mmol) of sodium cyanoborohydride was added, and the reaction solution was then adjusted to pH 3 using a few drops of 1N hydrochloric acid and stirred at RT overnight. The reaction solution was evaporated, water was then added and the mixture was extracted three times with ethyl acetate. The combined organic phases were dried over magnesium sulfate, filtered and evaporated.

Yield: 1.05 g (92% of theory)

LC-MS (Method 6): $R_t$=1.38 min; MS (ESIpos): m/z=181 [M+H]$^+$.

Example 61A rac-Methyl 3-(1-bromoethyl)benzenecarboxylate 5 g (27.75 mmol) of methyl 3-(1-hydroxyethyl)benzenecarboxylate (Example 60A) were initially charged in 100 ml of toluene. At 0° C., 0.98 g (36.07 mmol) of phosphorus tribromide were added dropwise, and the mixture was stirred at RT for 45 min. The reaction solution was poured onto ice-water and extracted three times with ethyl acetate. The combined organic phases were dried over sodium sulfate, filtered and evaporated. The residue was purified by column chromatography on silica gel 60 (mobile phase:cyclohexane:ethyl acetate 50:1→40:1).

Yield: 3.66 g (54% of theory)

LC-MS (Method 3): $R_t$=2.38 min; MS (ESIpos): m/z=243 [M]$^+$.

$^1$H NMR (400 MHz, DMSO-d$_6$): δ=8.07 (s, 1H) 7.90 (d, 1H) 7.81 (d, 1H) 7.54 (t, 1H) 5.61 (q, 1H), 3.88 (s, 3H), 2.00 (d, 3H).

Example 62A rac-Methyl 3-[(1-({6-amino-3,5-dicyano-4-[4-(2-hydroxyethoxy)phenyl]pyridin-2-yl}sulfanyl)-ethyl]benzenecarboxylate 300 mg (0.96 mmol) of 2-amino-4-[4-(2-hydroxyethoxy)phenyl]-6-sulfanylpyridine-3,5-dicarbonitrile (Example 10A), 257 mg (1.06 mmol) of rac-methyl 3-(1-bromoethyl)benzenecarboxylate (Example 61A) and 242 mg (2.88 mmol) of sodium bicarbonate were dissolved in 5.2 ml of DMF and the mixture was stirred at RT overnight. Water was added, and the reaction mixture was extracted three times with ethyl acetate. The combined organic phases were dried over magnesium sulfate, filtered and concentrated using a rotary evaporator. The residue was purified by preparative HPLC (Chromasil, water/acetonitrile).

Yield: 387 mg (85% of theory)

LC-MS (Method 3): $R_t$=2.39 min; MS (ESIpos): m/z=475 [M+H]$^+$.

$^1$H NMR (400 MHz, DMSO-d$_6$): δ=8.20-7.95 (br s, 2H), 8.10 (s, 1H), 7.88 (dd, 2H), 7.54-7.36 (d, 3H), 7.14-6.96 (m, 2H), 5.28 (d, 1H), 4.07 (t, 2H) 3.74 (t, 2H), 1.75 (d, 3H).

Example 63A

Methyl 3-[(1-({6-amino-3,5-dicyano-4-[4-(2-hydroxyethoxy)phenyl]pyridin-2-yl}sulfanyl)ethyl]-benzenecarboxylate (Enantiomer A)

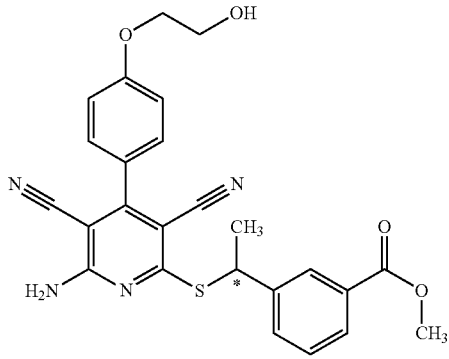

Chromatographic separation of rac-methyl 3-[(1-({6-amino-3,5-dicyano-4-[4-(2-hydroxyethoxy)-phenyl]pyridin-2-yl}sulfanyl)ethyl]benzenecarboxylate (Example 62A) on a chiral phase [Daicel Chiralpak AD-H, 5 µm 250*20 mm; mobile phase: 50% ethanol, 50% isohexane; flow rate 15 ml/min; 40° C.; detection: 220 nm] gave 143 mg (31% of theory) of Enantiomer A.

$^1$H NMR (400 MHz, DMSO-d$_6$): δ=8.07 (s, 1H) 7.90 (d, 1H) 7.81 (d, 1H) 7.54 (t, 1H) 5.61 (q, 1H), 3.88 (s, 3H), 2.00 (d, 3H).

Example 62A rac-Methyl 3-[(1-({6-amino-3,5-dicyano-4-[4-(2-hydroxyethoxy)phenyl]pyridin-2-yl}sulfanyl)-ethyl]benzenecarboxylate

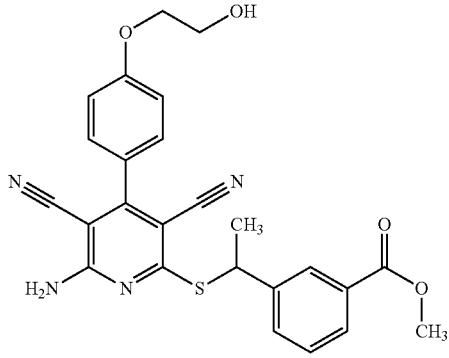

Enantiomer A: $R_t$=5.892 min [Chiralcel AD-H, 5 µm, 250×4.6 nm; mobile phase: 50% ethanol, 50% isohexane; flow rate 1.0 ml/min; detection: 220 nm].

Example 64A rac-Methyl 3-[1-({6-amino-3,5-dicyano-4-[4-(2-methoxyethoxy)phenyl]pyridin-2-yl}sulfanyl)-ethyl]benzenecarboxylate

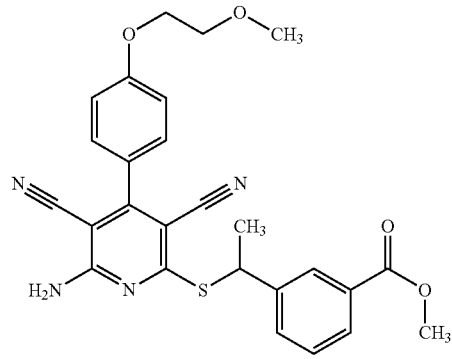 [SMILES: COCCOc1ccc(-c2c(C#N)c(N)nc(SC(C)c3cccc(C(=O)OC)c3)c2C#N)cc1]

300 mg (0.919 mmol) of 2-amino-4-[4-(2-methoxyethoxy)phenyl]-6-sulfanylpyridine-3,5-dicarbonitrile (Example 15A), 245 mg (1.01 mmol) of methyl 3-(1-bromoethyl)benzenecarboxylate (Example 61A) and 231 mg (2.76 mmol) of sodium bicarbonate were dissolved in 3 ml of DMF and the mixture was stirred at RT overnight. Water was added to the reaction mixture until a clear solution had formed. The solution was purified by preparative HPLC (Chromasil, water/acetonitrile+0.1% trifluoroacetic acid).

Yield: 335 mg (75% of theory)

LC-MS (Method 3): $R_t$=2.59 min; MS (ESIpos): m/z=489 [M+H]$^+$.

$^1$H NMR (400 MHz, DMSO-d$_6$): δ=8.20-7.95 (br s, 2H), 8.10 (s, 1H), 7.93-7.82 (m, 2H), 7.54-7.40 (m, 3H), 7.09 (d, 2H), 5.28 (q, 1H), 4.21-4.13 (m, 2H), 3.86 (s, 3H), 3.72-3.64 (m, 2H), 3.32 (s, 3H), 1.75 (d, 3H).

Example 65A

Methyl 3-[1-({6-amino-3,5-dicyano-4-[4-(2-methoxyethoxy)phenyl]pyridin-2-yl}sulfanyl)ethyl]-benzenecarboxylate (Enantiomer A)

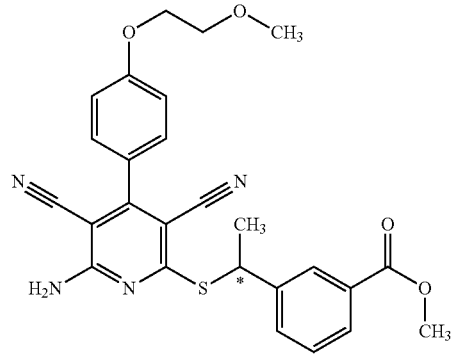 [SMILES: COCCOc1ccc(-c2c(C#N)c(N)nc(SC(C)c3cccc(C(=O)OC)c3)c2C#N)cc1]

Chromatographic separation of rac-methyl 3-[1-({6-amino-3,5-dicyano-4-[4-(2-methoxyethoxy)-phenyl]pyridin-2-yl}sulfanyl)ethyl]benzenecarboxylate (Example 64A) on a chiral phase [Daicel Chiralpak OD-H, 5 μm 250*20 mm; mobile phase: 50% 2-propanol, 50% isohexane; flow rate 15 ml/min; 35° C.; detection: 220 nm] gave 152 mg (34% of theory) of Enantiomer A.

Enantiomer A: $R_t$=8.162 min [Chiralcel OD-H, 5 μm, 250×4.6 nm; mobile phase: 50% 2-propanol, 50% isohexane; flow rate 1.0 ml/min; 40° C.; detection: 220 nm].

Example 66A 3-(Hydroxymethyl)benzenecarboxylic acid

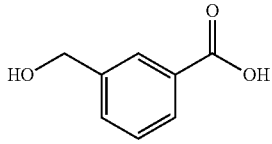 [SMILES: O=C(O)c1cccc(CO)c1]

The preparation was carried out as described in the Bayer Patent DE 113512 of 1900.

Yield: (33% of theory, 86% pure)

LC-MS (Method 6): $R_t$=0.38 min; MS (ESIpos): m/z=153 [M+H]$^+$.

$^1$H NMR (400 MHz, DMSO-d$_6$): δ=13.10-12.60 (br s, 1H), 7.92 (s, 1H), 7.81 (d, 1H), 7.55 (d, 1H), 7.45 (t, 1H), 5.50-5.15 (br s, 1H), 4.55 (s, 2H).

Example 67A 4-({[6-Chloro-3,5-dicyano-4-(3,4-difluorophenyl)pyridin-2-yl]sulfanyl}methyl)-N-methylpyridine-2-carboxamide

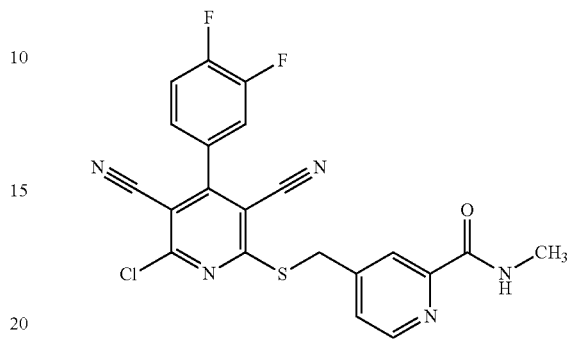

Under argon, 0.86 g (1.97 mmol) of 4-({[6-amino-3,5-dicyano-4-(3,4-difluorophenyl)pyridin-2-yl]sulfanyl}methyl)-N-methylpyridine-2-carboxamide (Example 4), 0.46 g (3.93 mmol) of isopentyl nitrite and 0.53 g (3.93 mmol) of copper(II) chloride were initially charged in 20 ml of acetonitrile and the mixture was stirred at 65° C. overnight. After a reaction time of 3 h, another 0.23 g (1.97 mmol) of isopentyl nitrite and 0.26 g (1.97 mmol) of copper (II) chloride were added to the reaction mixture. After cooling to RT, 3.93 ml of 1N hydrochloric acid were added. The aqueous phase was extracted three times with ethyl acetate. The combined organic phases were dried over sodium sulfate, filtered and evaporated. The residue was purified by preparative HPLC (Chromasil, water/acetonitrile+0.1% trifluoroacetic acid).

Yield: 0.56 g (62% of theory)

LC-MS (MHZ-Z2-GEM): $R_t$=2.47 min; MS (ESIpos): m/z=456 [M+H]$^+$.

The examples listed in Table 4 were prepared analogously to Example 67A from the appropriate starting materials.

TABLE 4

| Example No. | Structure (yield) | LC-MS: $R_t$ [min] (Method); MS (ESI): m/z [M + H]$^+$ |
| --- | --- | --- |
| 68A | (57% of theory) | 1.21 min (Method 6); m/z = 478 |

TABLE 4-continued

| Example No. | Structure (yield) | LC-MS: $R_t$ [min] (Method); MS (ESI): m/z [M + H]$^+$ |
|---|---|---|
| 69A | (structure) (66% of theory) *10 | 1.13 min (Method 6); m/z = 494 |
| 70A | (structure) (20% of theory) *10 | 2.43 min (Method 3); m/z = 450 |
| 71A | (structure) (48% of theory) *11 | 2.03 min (Method 3); m/z = 481 |

TABLE 4-continued
| Example No. | Structure (yield) | LC-MS: R$_t$ [min] (Method); MS (ESI): m/z [M + H]$^+$ |
|---|---|---|
| 72A | 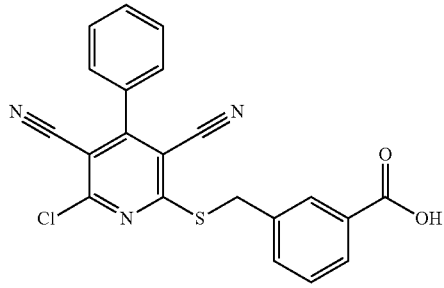 [SMILES: N#Cc1c(Cl)nc(SCc2cccc(C(=O)O)c2)c(C#N)c1-c1ccccc1]<br>(77% of theory)<br>*12 | 3.60 min (Method 9); m/z = 406 |
| 73A | 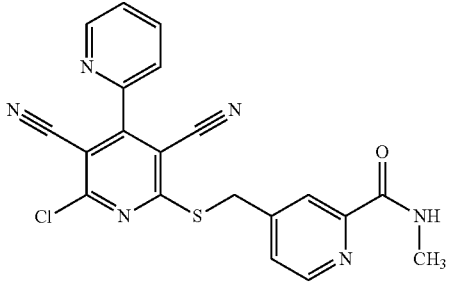 [SMILES: CNC(=O)c1cc(CSc2nc(Cl)c(C#N)c(-c3ccccn3)c2C#N)ccn1]<br>(58% of theory)<br>*12 | 1.08 min (Method 6); m/z = 421 |
| 74A | 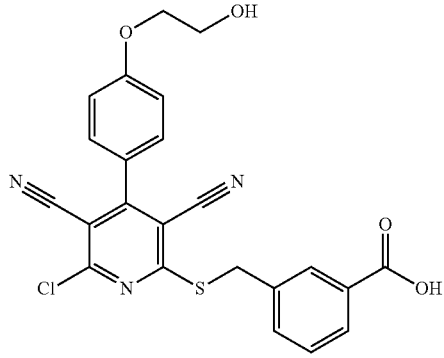 [SMILES: N#Cc1c(Cl)nc(SCc2cccc(C(=O)O)c2)c(C#N)c1-c1ccc(OCCO)cc1]<br>*13 | 2.28 min (Method 3); m/z = 466 |
| 75A | 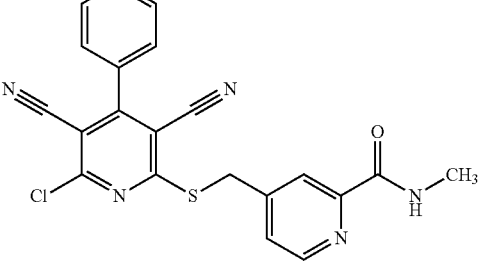<br>(87% of theory)<br>*14 | 2.46 min (Method 3); m/z = 420 |

TABLE 4-continued
| Example No. | Structure (yield) | LC-MS: R_t [min] (Method); MS (ESI): m/z [M + H]+ |
|---|---|---|
| 76A | 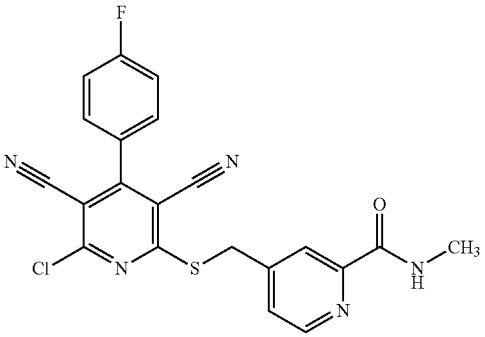<br>(32% of theory)<br>*15 | 2.42 min (Method 3); m/z = 438 |
| 77A | 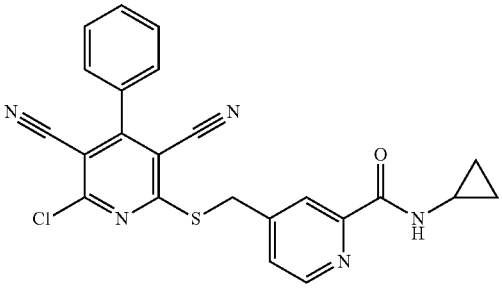 [SMILES: N#Cc1c(Cl)nc(SCc2ccnc(C(=O)NC3CC3)c2)c(C#N)c1-c1ccccc1]<br>(19% of theory)<br>*16 | 1.28 min (Method 6); m/z = 446 |
| 78A | 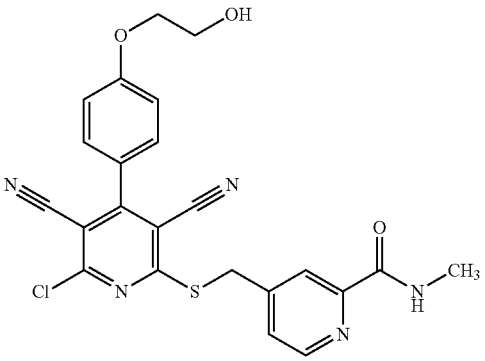<br>(41% of theory) | 1.07 min (Method 6); m/z = 480 |

TABLE 4-continued

| Example No. | Structure (yield) | LC-MS: $R_t$ [min] (Method); MS (ESI): m/z [M + H]$^+$ |
|---|---|---|
| 79A | 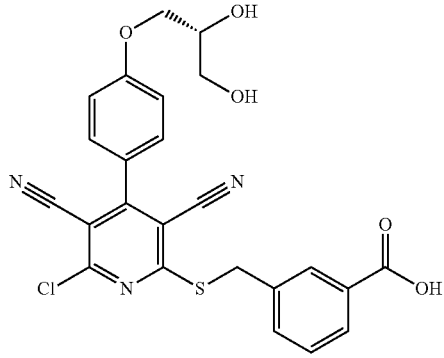 [SMILES: N#Cc1c(Cl)nc(SCc2cccc(C(=O)O)c2)c(C#N)c1-c1ccc(OC[C@H](O)CO)cc1] (53% of theory) *17 | 1.70 min (Method 4); m/z = 496 |
| 80A | 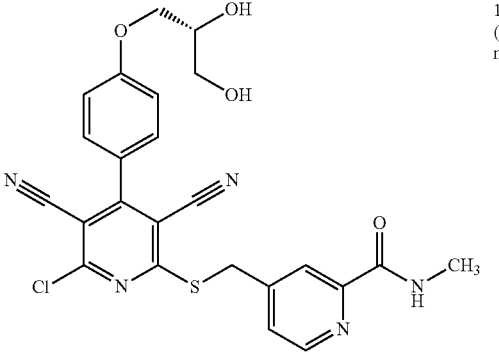 (37% of theory) *18 | 1.55 min (Method 4); m/z = 10 |

*10 Different procedure; during the reaction, no further isopentyl nitrite and copper(II) chloride were added to the reaction mixture.

*11 Different procedure; during the reaction, no further isopentyl nitrite and copper(II) chloride were added to the reaction mixture. Different work-up; the extracted organic phase was concentrated using a rotary evaporator.

*12 Different procedure; during the reaction, no further isopentyl nitrite and copper(II) chloride were added to the reaction mixture. The reaction time was 4 h. Different work-up; the extracted organic phase was concentrated using a rotary evaporator.

*13 Different procedure; during the reaction, no further isopentyl nitrite and copper(II) chloride were added to the reaction mixture. The reaction time was 4 h. Different work-up; the combined organic phases were washed once with saturated aqueous sodium bicarbonate solution, twice with water and once with saturated aqueous sodium chloride solution. The organic phase was dried over sodium sulfate, filtered and evaporated.

*14 Different procedure; during the reaction, a further 1 eq of copper(II) chloride was added to the reaction mixture.

*15 Different work-up; after the addition of 1N hydrochloric acid, a precipitate was formed. The precipitate was filtered off and the filtrate was evaporated. The precipitate contained the desired product. The filtrate also contained product. The filtrate was concentrated using a rotary evaporator and purified by preparative HPLC (Chromasil, water/acetonitrile + 0.1% trifluoroacetic acid).

*16 Different procedure; during the reaction, no further isopentyl nitrite and copper(II) chloride were added to the reaction mixture. The reaction time was 3 h.

*17 Different procedure; during the reaction, no further isopentyl nitrite and copper(II) chloride were added to the reaction mixture. The reaction time was 1 h. During work-up, the acetonide was deprotected. After the addition of 1N hydrochloric acid, the mixture was stirred at RT for 30 min.

*18 Different procedure; during the reaction, no further isopentyl nitrite and copper(II) chloride were added to the reaction mixture. Different work-up; after the addition of 1N hydrochloric acid, a precipitate was formed. The precipitate was filtered off and the filtrate was evaporated. The precipitate and the filtrate, which was concentrated using a rotary evaporator, were purified by preparative HPLC (Chromasil, water/acetonitrile + 0.1% trifluoroacetic acid).

Example 81A 4-({[6-Chloro-3,5-dicyano-4-(4-fluorophenyl)pyridin-2-yl]oxy}methyl)-N-methylpyridine-2-carboxamide

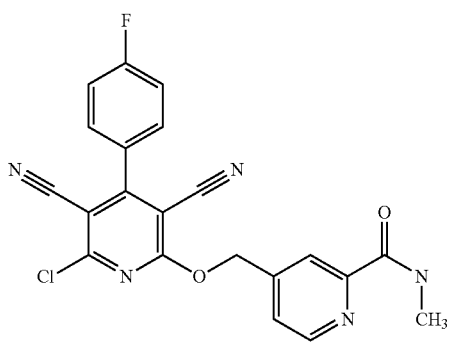 [SMILES: CNC(=O)c1cc(COc2nc(Cl)c(C#N)c(-c3ccc(F)cc3)c2C#N)ccn1]

500 mg (1.24 mmol) of 4-({[6-amino-3,5-dicyano-4-(4-fluorophenyl)pyridin-2-yl]oxy}methyl)-N-methylpyridine-2-carboxamide (Example 21) were suspended in ice-cooled conc. hydrochloric acid. 257 mg (3.73 mmol) of sodium nitrite were added in portions, and the reaction mixture was then warmed to RT and stirred at RT for 1 h. 25 ml of water were added, and the reaction mixture was extracted three times with dichloromethane. The combined organic phases were washed three times with saturated aqueous sodium chloride solution, dried over magnesium sulfate, filtered and evaporated. The residue was purified by preparative HPLC (Chromasil, water/acetonitrile).

Yield: 154 mg (30% of theory)

LC-MS (Method 3): $R_t$=2.37 min; MS (ESIpos): m/z=422 [M+H]$^+$.

The examples listed in Table 5 were prepared analogously to Example 81A from the appropriate starting materials.

TABLE 5

| Example No. | Structure (yield) | LC-MS: $R_t$ [min] (Method); MS (ESI): m/z [M + H]$^+$ |
|---|---|---|
| 82A | (74% of theory) *19 | 2.32 min (Method 3); m/z = 508 |
| 83A | (58% of theory) *20 | 1.18 min (MHZ-QP.GO-1); m/z = 404 |

*19 Different work-up; the organic phase was concentrated using a rotary evaporator and not purified any further.

*20 Different work-up; the residue was purified by column chromatography on silica gel 60 (mobile phase: dichloromethane/ethyl acetate 1/0 → 20/1).

Example 84A

3-[({6-Chloro-3,5-dicyano-4-[4-(2-hydroxyethoxy)phenyl]pyridin-2-yl}sulfanyl)methyl]-N-methylbenzenecarboxamide

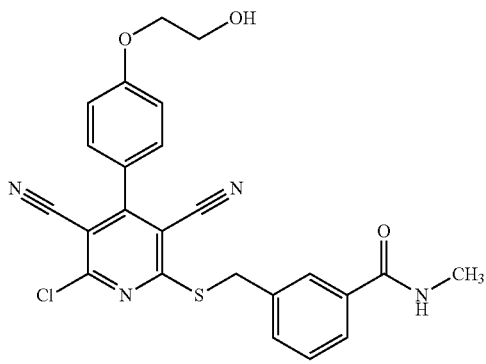 [SMILES: CNC(=O)c1cccc(CSc2nc(Cl)c(C#N)c(-c3ccc(OCCO)cc3)c2C#N)c1]

2 g (4.35 mmol) of 3-[({6-amino-3,5-dicyano-4-[4-(2-hydroxyethoxy)phenyl]pyridin-2-yl}-sulfanyl)methyl]-N-methylbenzenecarboxamide Example 8 were dissolved in ice-cooled conc. hydrochloric acid. 0.9 g (13.06 mmol) of sodium nitrite was added, and the mixture was then stirred at 0° C. for 1 h. After 30 min, a barely stirrable solution had formed. 200 ml of water were added to the reaction mixture. The precipitate was filtered off and purified by column chromatography on silica gel 60 (mobile phase: dichloromethane/methanol 50/1→20/1).

Yield: 1.24 g (58% of theory)

LC-MS (Method 6): $R_t$=1.09 min; MS (ESIpos): m/z=479 [M+H]$^+$.

Example 85A

3-{[(6-Chloro-3,5-dicyano-4-phenylpyridin-2-yl)sulfanyl]methyl}-N-methylbenzenecarboxamide

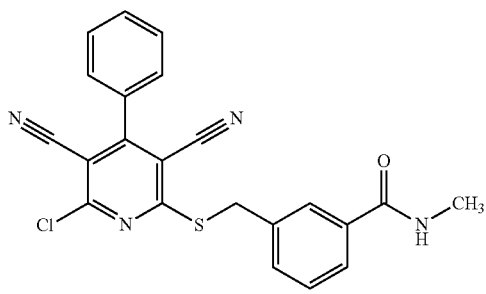 [SMILES: CNC(=O)c1cccc(CSc2nc(Cl)c(C#N)c(-c3ccccc3)c2C#N)c1]

1.72 g (4.3 mmol) of 3-{[(6-amino-3,5-dicyano-4-phenylpyridin-2-yl)sulfanyl]methyl}-N-methylbenzenecarboxamide Example 9 were dissolved in ice-cooled conc. hydrochloric acid. 0.89 g (12.89 mmol) of sodium nitrite was added, and the mixture was then stirred at 0° C. for 1 h and at RT overnight. After 1 h, a precipitate had already formed. With cooling, 100 ml of water were added to the reaction mixture, and the pH was adjusted carefully to pH 7 using conc. aqueous sodium hydroxide solution. The precipitate was filtered off.

Yield: 398 mg (22% of theory)

LC-MS (Method 6): $R_t$=1.24 min; MS (ESIpos): m/z=419 [M+H]$^+$.

Example 86A

N-(3-Formylphenyl)methanesulfonamide

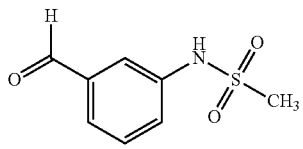

1.3 g (10.73 mmol) of 3-aminobenzenecarbaldehyde were initially charged in 30 ml of dichloromethane. 849 mg (10.73 mmol) of pyridine and 1.3 g (10.73 mmol) of methanesulfonyl chloride were added, and the mixture was then stirred at RT overnight. Ethyl acetate was added, and the reaction solution was washed in each case once with 1 N hydrochloric acid, water and saturated aqueous sodium bicarbonate solution. The organic phase was dried over sodium sulfate, filtered and evaporated. The residue was purified by column chromatography on silica gel 60 (mobile phase: dichloromethane/methanol 100/0→50/1).

Yield: 935 mg (42% of theory)

LC-MS (Method 8): $R_t$=1.20 min; MS (ESIpos): m/z=198 [M−H]$^-$.

Example 87A rac-N-[3-(1-Hydroxyethyl)phenyl]methanesulfonamide

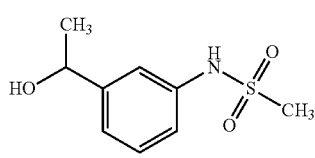

Under argon and at 0° C., 83 mg (0.417 mmol) of N-(3-formylphenyl)methanesulfonamide (Example 86A) were initially charged in 1 ml of abs. tetrahydrofuran. At 0° C., 99 mg (0.833 mmol) of methylmagnesium bromide (3 M in diethyl ether) were added dropwise (resulting in the formulation of a precipitate), and the reaction solution was stirred at this temperature for 2 h. The reaction solution was quenched with water and extracted three times with ethyl acetate. The combined organic phases were dried over sodium sulfate, filtered and evaporated.

Yield: 80 mg (89% of theory)

LC-MS (Method 8): $R_t$=1.15 min; MS (ESIpos): m/z=214 [M−H]$^-$.

Example 88A rac-N-[3-(1-Chloroethyl)phenyl]methanesulfonamide

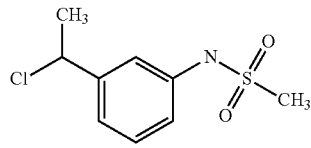

650 mg (3.02 mmol) of rac-N-[3-(1-hydroxyethyl)phenyl]methanesulfonamide (Example 87A) were initially charged in 9 ml of dichloromethane. At 0° C., 1.08 g (9.07 mmol) of thionyl chloride were added dropwise, and the reaction solution was stirred at RT for 3 h. The reaction solution was evaporated.

Yield: 706 mg (49% of theory, 49% pure)
DCI-MS (Method 12): MS (ESIpos): m/z=251 [M+NH4]$^+$.

Example 89A 3-(Chloromethyl)aniline hydrochloride

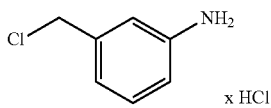

At 0° C., 2.0 g (16.24 mmol) of 3-aminobenzyl alcohol were initially charged in 60 ml of dichloromethane. 5.8 g (48.72 mmol) of thionyl chloride were added dropwise, and the reaction solution was stirred at RT overnight. The reaction solution was evaporated.

Yield: 2.92 g (87% of theory, 86% pure).
LC-MS (Method 6): $R_t$=0.55 min; MS (ESIpos): m/z=142 [M+H]$^+$.

Example 90A

N-[3-(Chloromethyl)phenyl]methanesulfonamide

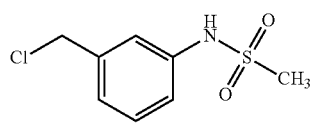

873 mg (4.903 mmol) of 3-(chloromethyl)aniline hydrochloride (Example 89A) were initially charged in 4 ml of tetrahydrofuran, and 2.48 g (24.514 mmol) of triethylamine were added. A solution of 421 mg (3.677 mmol) of methanesulfonyl chloride in 3 ml of tetrahydrofuran was slowly added dropwise, and the reaction solution was stirred at RT for 2 h. The reaction solution was concentrated using a rotary evaporator and the residue was purified by preparative HPLC (Chromasil, water/acetonitrile).

Yield: 377 mg (35% of theory)
LC-MS (Method 8): $R_t$=1.87 min; MS (ESIpos): m/z=218 [M-H]$^-$.

Example 91A

N-[3-(Chloromethyl)phenyl]benzenesulfonamide

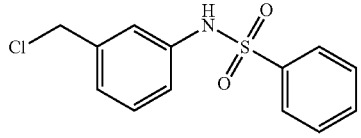 [SMILES: O=S(=O)(Nc1cccc(CCl)c1)c1ccccc1]

The preparation was carried out as described in Example 90A, using the appropriate starting materials.

Yield: 203 mg (25% of theory)
LC-MS (Method 4): $R_t$=1.85 min; MS (ESIpos): m/z=282 [M+H]$^+$.

Example 92A 3-(Hydroxymethyl)benzenesulfonamide

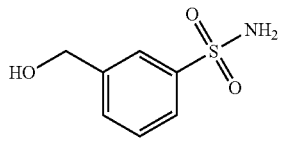 [SMILES: NS(=O)(=O)c1cccc(CO)c1]

The preparation was carried out as described in the patent WO2003/991204 A1 (Glaxo Group).

Example 93A 3-(Chloromethyl)benzenesulfonamide

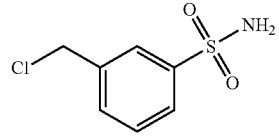 [SMILES: NS(=O)(=O)c1cccc(CCl)c1]

The preparation was carried out as described for Example 41A.

LC-MS (MHZ-SQ1-HSST3): $R_t$=0.60 min; MS (ESIneg): m/z=204 [M-H]$^+$.

WORKING EXAMPLES

Example 1

4-{[(6-Amino-3,5-dicyano-4-phenylpyridin-2-yl)sulfanyl]methyl}-N-methylpyridine-2-carboxamide

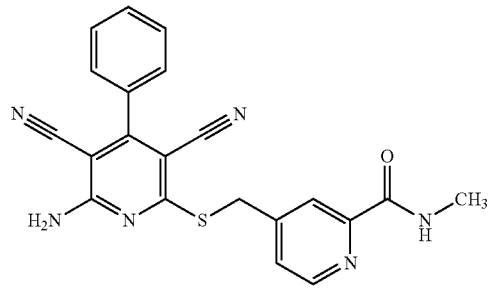 [SMILES: CNC(=O)c1cc(CSc2nc(N)c(C#N)c(-c3ccccc3)c2C#N)ccn1]

1.00 g (3.96 mmol) of 2-amino-4-phenyl-6-sulfanylpyridine-3,5-dicarbonitrile (Example 30A), 0.96 g (4.36 mmol) of 4-(chloromethyl)-N-methylpyridine-2-carboxamide hydrochloride (Example 41A) and 1.33 g (15.84 mmol) of sodium bicarbonate were dissolved in 20 ml of DMF and the mixture was stirred at RT for 2 h. 500 ml of water were added to the reaction mixture. The precipitate was filtered off and washed with water.

Yield: 1.42 g (90% of theory)

LC-MS (Method 4): $R_t$=1.74 min; MS (ESIpos): m/z=401 [M+H]$^+$.

$^1$H NMR (400 MHz, DMSO-d$_6$): δ=8.74 (q, 1H), 8.55 (d, 1H), 8.30-7.96 (br s, 2H), 8.15 (s, 1H), 7.80-7.75 (m, 1H), 7.58-7.50 (m, 5H), 4.60 (s, 2H), 2.81 (d, 3H).

The examples listed in Table 6 were prepared analogously to Example 1 from the appropriate starting materials.

TABLE 6

| Example No. | Structure (yield) | LC-MS: $R_t$ [min] (Method); MS (ESI): m/z [M + H]$^+$ | $^1$H NMR (DMSO-d$_6$): |
|---|---|---|---|
| 2 *4 | 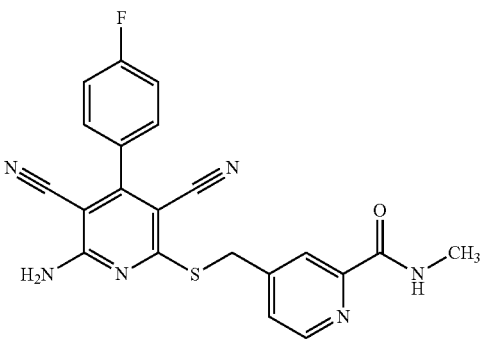 | 2.22 min (Method 3); m/z = 419 | δ = 8.74 (q, 1H), 8.55 (d, 1H), 8.15 (s, 1H), 7.80-7.76 (m, 1H), 7.61 (dd, 2H), 7.40 (t, 2H), 4.60 (s, 2H), 2.81 (d, 3H). |
| 3 | 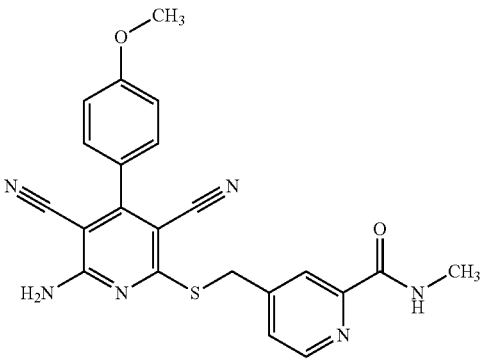 (72% d.Th.) | 1.10 min (Method 6); m/z = 431 | δ = 8.75 (q, 1H), 8.55 (d, 1H), 8.14 (s, 1H), 7.80-7.75 (m, 1H), 7.49 (d, 2H), 7.10 (d, 2H), 4.59 (s, 2H), 3.83 (s, 3H), 2.81 (d, 3H). |
| 4 | 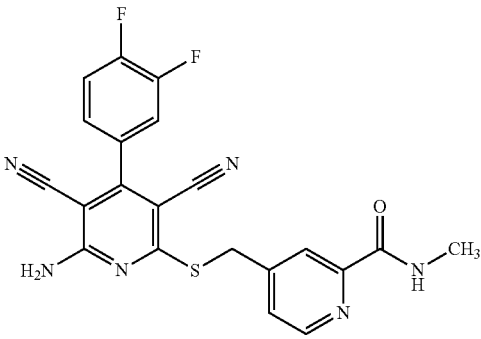 [SMILES: CNC(=O)c1cc(CSc2nc(N)c(C#N)c(-c3ccc(F)c(F)c3)c2C#N)ccn1] (50% of theory) | 1.15 min (Method 6); m/z = 437 | δ = 8.74 (q, 1H), 8.55 (d, 1H), 8.15 (s, 1H), 7.84-7.74 (m, 2H), 7.66 (q, 1H), 7.48-7.41 (m, 1H), 4.60 (s, 2H), 2.81 (d, 3H). |

TABLE 6-continued
| Example No. | Structure (yield) | LC-MS: R$_t$ [min] (Method); MS (ESI): m/z [M + H]$^+$ | $^1$H NMR (DMSO-d$_6$): |
|---|---|---|---|
| 5 | 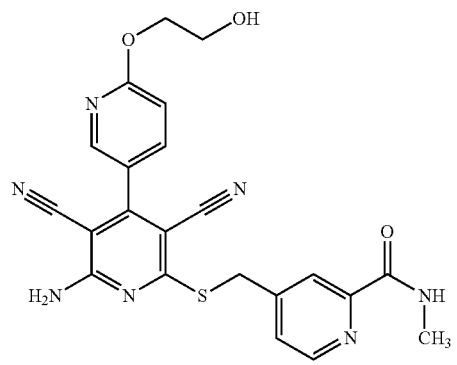<br>(86% of theory)<br>*4 | 0.90 min (Method 6); m/z = 462 | δ = 8.75 (q, 1H), 8.55 (d, 1H), 8.34 (s, 1H), 8.15 (s, 1H), 7.92 (dd, 1H), 7.78 (d, 1H), 6.99 (d, 1H), 4.88 (t, 1H), 4.60 (s, 2H), 4.35 (t, 2H), 3.73 (q, 2H), 2.81 (d, 3H). |
| 6 | 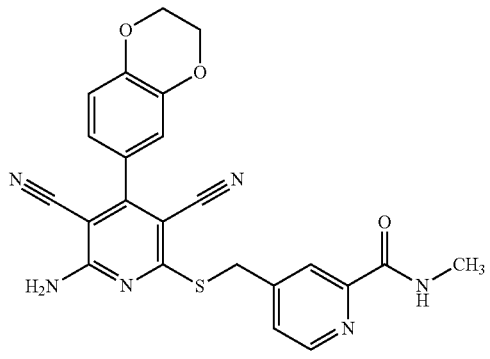 [SMILES: CNC(=O)c1cc(CSc2nc(N)c(C#N)c(-c3ccc4c(c3)OCCO4)c2C#N)ccn1]<br>(62% of theory) | 1.07 min (Method 6); m/z = 459 | δ = 8.80-8.70 (m, 1H), 8.59-8.51 (m, 1H), 8.18-8.12 (m, 1H), 7.83-7.74 (m, 1H), 7.12-7.05 (m, 1H), 7.04-6.95 (m, 2H), 4.58 (s, 2H), 4.38-4.26 (m, 4H), 2.81 (d, 3H). |
| 7 | 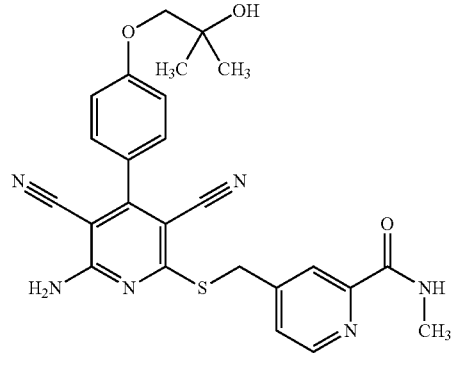<br>(55% of theory)<br>*4 | 2.11 min (Method 3); m/z = 489 | δ = 8.74 (q, 1H), 8.55 (d, 1H), 8.14 (s, 1H), 7.80-7.74 (m, 1H), 7.47 (d, 2H), 7.09 (d, 2H), 4.67 (s, 1H), 4.59 (s, 2H), 3.79 (s, 2H), 2.81 (d, 3H), 1.22 (s, 6H). |

TABLE 6-continued
| Example No. | Structure (yield) | LC-MS: R$_t$ [min] (Method); MS (ESI): m/z [M + H]$^+$ | $^1$H NMR (DMSO-d$_6$): |
|---|---|---|---|
| 8 | 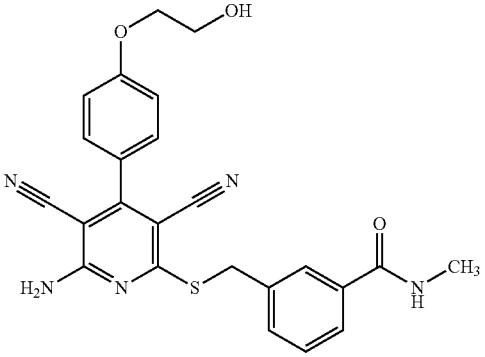<br>(95% of theory) | 1.94 min (Method 3); m/z = 460 | δ = 8.42 (q, 1H), 7.95 (s, 1H), 7.70 (t, 2H), 7.47 (d, 2H), 7.40 (t, 1H), 7.09 (d, 2H), 4.91 (t, 1H), 4.54 (s, 2H), 4.07 (t, 2H), 3.74 (q, 2H), 2.78 (d, 3H). |
| 9 | 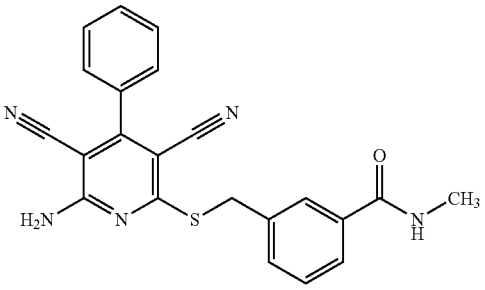<br>(98% of theory) | 1.10 min (Method 6); m/z = 400 | δ = 8.43 (q, 1H), 7.96 (s, 1H), 7.70 (t, 2H), 7.59-7.49 (m, 5H), 7.40 (t, 1H), 4.55 (s, 2H), 2.79 (d, 3H). |
| 10 | 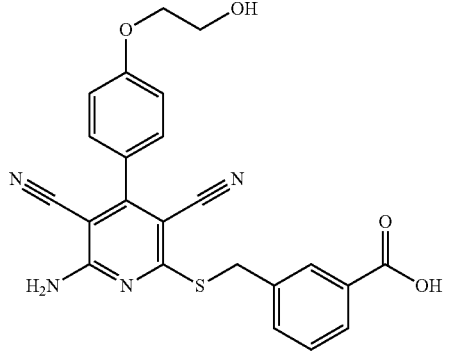<br>(97% of theory)<br>*6 | 2.84 min (Method 9); m/z = 447 | δ = 13.00 (br s, 1H), 8.05 (s, 1H), 7.82 (t, 2H), 7.47 (d, 2H), 7.43 (d, 1H), 7.09 (d, 2H), 4.91 (t, 1H), 4.58 (s, 2H), 4.07 (t, 2H), 3.74 (q, 2H). |
| 11 | 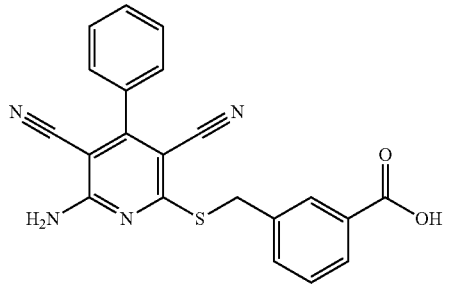 [SMILES: N#Cc1c(N)nc(SCc2cccc(C(=O)O)c2)c(C#N)c1-c1ccccc1]<br>(79% of theory)<br>*6 | 1.13 min (Method 6); m/z = 387 | δ = 13.01 (br s, 1H), 8.06 (s, 1H), 7.82 (t, 2H), 7.59-7.49 (m, 5H), 7.45 (t, 1H), 4.59 (s, 2H). |

TABLE 6-continued
| Example No. | Structure (yield) | LC-MS: R_t [min] (Method); MS (ESI): m/z [M + H]+ | $^1$H NMR (DMSO-d$_6$): |
|---|---|---|---|
| 12 |  (42% of theory) *8 | 1.93 min (Method 3); m/z = 402 | no NMR data |
| 13 | 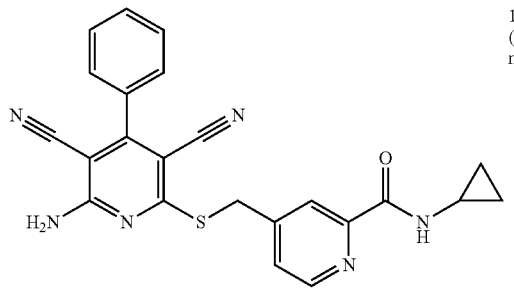 (98% of theory) | 1.16 min (Method 6); m/z = 427 | δ = 8.70 (d, 1H), 8.53 (d, 1H), 8.14 (s, 1H), 7.81-7.75 (m, 1H), 7.60-47 (m, 5H), 4.60 (s, 2H), 2.94-2.85 (m, 1H), 0.75-0.61 (m, 4H). |
| 14 | 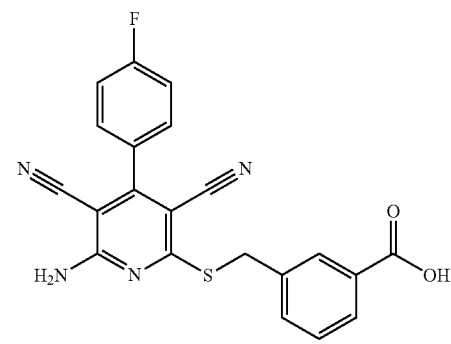 [SMILES: N#Cc1c(N)nc(SCc2cccc(C(=O)O)c2)c(C#N)c1-c1ccc(F)cc1] (60% of theory) *9 | 1.88 min (Method 4); m/z = 405 | δ = 13.01 (br s, 1H), 8.06 (s, 1H), 7.82 (t, 2H), 7.66-7.57 (m, 2H), 7.49-7.35 (m, 3H), 4.59 (s, 2H). |

TABLE 6-continued

| Example No. | Structure (yield) | LC-MS: $R_t$ [min] (Method); MS (ESI): m/z [M + H]$^+$ | $^1$H NMR (DMSO-$d_6$): |
|---|---|---|---|
| 15 | (91% of theory) *23 | 1.22 min (Method 6); m/z = 372 | δ = 13.04 (br s, 1H), 9.23 (s, 1H), 8.07 (s, 1H), 7.85 (d, 1H), 7.74 (d, 1H), 7.69-7.57 (m, 5H), 7.48 (t, 1H), 4.73 (s, 2H). |

*4 Different procedure; reaction time overnight. After a reaction time of 18 h, another 0.25 eq. of 4-(chloromethyl)-N-methylpyridine-2-carboxamide hydrochloride (Example 41A) was added, and the reaction mixture was stirred at room temperature for a further 2 h. The precipitate was filtered off.
*6 Different work-up; water was added, and the pH of the reaction mixture was adjusted to pH 1 using 1N hydrochloric acid. The precipitate was filtered off.
*8 Different procedure; reaction time overnight. Different work-up; the precipitate was filtered off and the filtrate was evaporated. The residue obtained after evaporation was purified by column chromatography on silica gel 60 (mobile phase: dichloromethane/ethanol 20/1 → 7/1).
*9 Different work-up; water was added, and the pH of the reaction mixture was adjusted to pH 1 using 1N hydrochloric acid. A viscous precipitae was formed, the mixture was extracted three times with ethyl acetate, the combined organic phases were washed with saturated aqueous sodium chloride solution, dried over sodium sulfate, filtered and evaporated. The residue was purified by preparative HPLC (Chromasil, water/acetonitrile + 0.1% trifluoroacetic acid).
*23 Different procedure; reaction time overnight. Different work-up; water and tetrahydrofuran were added to the reaction mixture until a clear solution had formed. The solution was purified by preparative HPLC (Chromasil, water/acetonitrile + 0.1% trifluoroacetic acid).

Example 16 rac-3-[(1S)-1-({6-Amino-3,5-dicyano-4-[4-(2-hydroxyethoxy)phenyl]pyridin-2-yl}sulfanyl)-ethyl]benzenecarboxylic acid

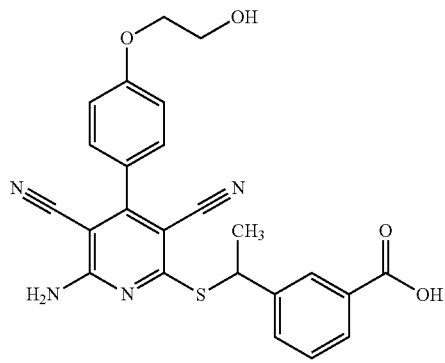 [SMILES: CC(Sc1nc(N)c(C#N)c(-c2ccc(OCCO)cc2)c1C#N)c1cccc(C(=O)O)c1]

85 mg (0.179 mmol) of rac-methyl 3-[(1S)-1-({6-amino-3,5-dicyano-4-[4-(2-hydroxyethoxy)phenyl]pyridin-2-yl}sulfanyl)ethyl]benzenecarboxylate (Example 62A) were dissolved in 4 ml of tetrahydrofuran. 8.58 mg (0.358 mmol) of lithium hydroxide were added, and the mixture was then stirred at RT overnight. The reaction solution was adjusted to pH 4 using 1N hydrochloric acid and extracted three times with ethyl acetate. The combined organic phases were dried over magnesium sulfate, filtered and evaporated.

Yield: 69 mg (84% of theory)

LC-MS (Method 3): $R_t$=2.13 min; MS (ESIpos): m/z=461 [M+H]$^+$.

Example 17

3-[(1S)-1-({6-Amino-3,5-dicyano-4-[4-(2-hydroxyethoxy)phenyl]pyridin-2-yl}sulfanyl)ethyl]-benzenecarboxylic acid (Enantiomer A)

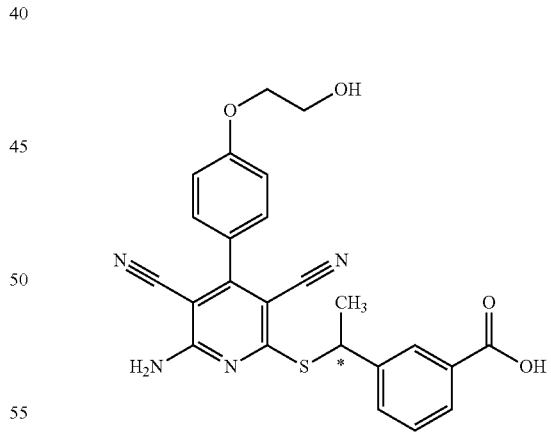

The preparation was carried out as described in Example 16 using the starting material methyl 3-[(1-({6-amino-3,5-dicyano-4-[4-(2-hydroxyethoxy)phenyl]pyridin-2-yl}sulfanyl)ethyl]benzenecarboxylate (Example 63A).

LC-MS (Method 6): $R_t$=1.06 min; MS (ESIpos): m/z=461 [M+H]$^+$.

Example 18

3-[({6-Amino-3,5-dicyano-4-[4-(2-hydroxyethoxy)phenyl]pyridin-2-yl}oxy)methyl]benzenecarboxylic acid

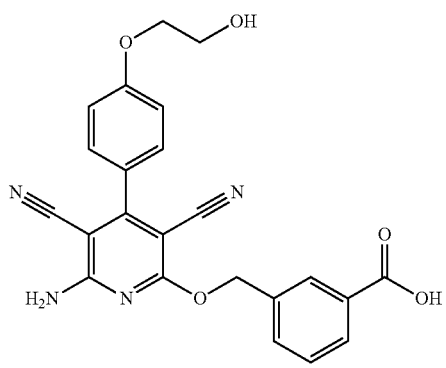 [SMILES: N#Cc1c(N)nc(OCc2cccc(C(=O)O)c2)c(C#N)c1-c1ccc(OCCO)cc1]

1.65 g (14.68 mmol) of potassium tert-butoxide were suspended in 15 ml of 1,2-dimethoxyethane. After addition of 0.97 g (5.87 mmol) of 3-(hydroxymethyl)benzenecarboxylic acid (Example 66A) and 1.14 g (2.94 mmol) of 2-amino-4-[4-(2-hydroxyethoxy)phenyl]-6-(phenylsulfanyl)pyridine-3,5-dicarbonitrile (Example 35A), the mixture was stirred at 60° C. overnight. After cooling of the reaction mixture, 50 ml of water were added. With ice-cooling, the clear solution was acidified to pH 1 using conc. hydrochloric acid. The aqueous phase was decanted from the viscous precipitate formed. The residue was purified by preparative HPLC (Chromasil, water/acetonitrile+0.1% trifluoroacetic acid). The aqueous phase was evaporated and the residue was purified by preparative HPLC (Chromasil, water/acetonitrile+0.1% trifluoroacetic acid).

Yield: 535 mg (42% of theory)

LC-MS (Method 4): $R_t$=1.46 min; MS (ESIpos): m/z=431 [M+H]$^+$.

Example 19

3-[1-({6-Amino-3,5-dicyano-4-[4-(2-methoxyethoxy)phenyl]pyridin-2-yl}sulfanyl)ethyl]-benzenecarboxylic acid (Enantiomer A)

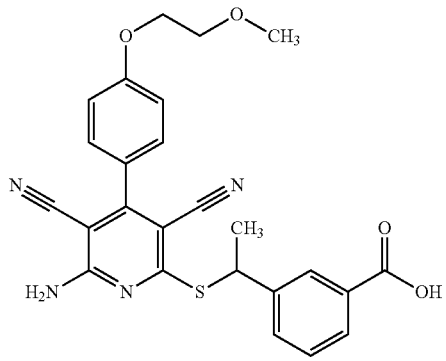 [SMILES: COCCOc1ccc(-c2c(C#N)c(N)nc(SC(C)c3cccc(C(=O)O)c3)c2C#N)cc1]

150 mg (0.307 mmol) of methyl 3-[1-({6-amino-3,5-dicyano-4-[4-(2-methoxyethoxy)phenyl]-pyridin-2-yl}sulfanyl)ethyl]benzenecarboxylate (Example 65A) were dissolved in 7 ml of tetrahydrofuran. After addition of 14.7 mg (0.61 mmol) of lithium hydroxide, the mixture was stirred at RT overnight. The mixture was then stirred at 40° C. for 4 h. Using 1N hydrochloric acid, the pH of the reaction solution was adjusted to pH 4, and the clear solution was purified by preparative HPLC (Chromasil, water/acetonitrile+0.1% trifluoroacetic acid).

Yield: 130 mg (89% of theory)

LC-MS (Method 4): $R_t$=1.91 min; MS (ESIpos): m/z=475 [M+H]$^+$.

$^1$H NMR (400 MHz, DMSO-d$_6$): δ=13.25-12-80 (br s, 1H), 8.20-7.95 (br s, 2H), 8.10 (s, 1H), 7.88-7.82 (m, 2H), 7.51-7.42 (m, 3H), 7.09 (d, 2H), 5.28 (q, 1H), 4.21-4.13 (m, 2H), 3.72-3.64 (m, 2H), 3.32 (s, 3H), 1.75 (d, 3H).

Example 20

3-[({6-Amino-3,5-dicyano-4-[4-(2-hydroxyethoxy)phenyl]pyridin-2-yl}oxy)methyl]benzenecarboxylic acid

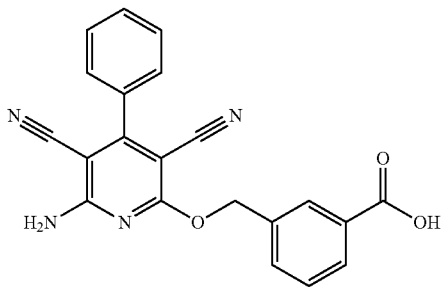 [SMILES: N#Cc1c(N)nc(OCc2cccc(C(=O)O)c2)c(C#N)c1-c1ccccc1]

4.72 g (42.06 mmol) of potassium tert-butoxide were suspended in 25 ml of 1,2-dimethoxyethane. After addition of 1.73 g (10.51 mmol) of 3-(hydroxymethyl)benzenecarboxylic acid (Example 66A) and 1.72 g (5.26 mmol) of 2-amino-4-phenyl-6-(phenylsulfanyl)pyridine-3,5-dicarbonitrile (Example 36A), the mixture was stirred at 60° C. overnight. After cooling of the reaction mixture, 50 ml of water were added. With ice-cooling, the clear solution was acidified to pH 6-7 using conc. hydrochloric acid. The solution was evaporated. Purification was by column chromatography on silica gel 60 (mobile phase: cyclohexane/ethyl acetate 1/1, finally acetonitrile/water 10/1).

Yield: 1.52 g (50% of theory)

LC-MS (Method 3): $R_t$=2.19 min; MS (ESIpos): m/z=371 [M+H]$^+$.

Example 21

4-({[6-Amino-3,5-dicyano-4-(4-fluorophenyl)pyridin-2-yl]oxy}methyl)-N-methylpyridine-2-carboxamide

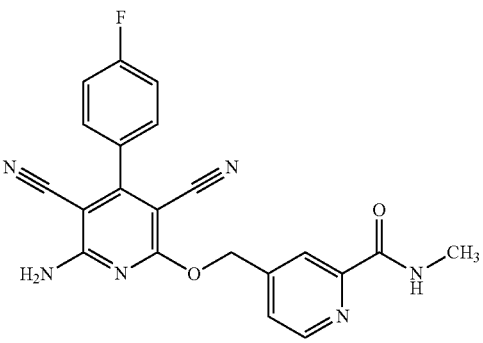 [SMILES: CNC(=O)c1cc(COc2nc(N)c(C#N)c(-c3ccc(F)cc3)c2C#N)ccn1]

1.62 g (14.44 mmol) of potassium tert-butoxide were suspended in 10 ml of 1,2-dimethoxyethane. After addition of 1.44 g (8.66 mmol) of 4-(hydroxymethyl)-N-methylpyridine-2-carboxamide hydrochloride monohydrate (Example 40A) and 1.00 g (2.89 mmol) of 2-amino-4-[4-fluorophenyl]-6-(phenylsulfanyl)pyridine-3,5-dicarbonitrile (Example 38A), the mixture was stirred at 60° C. for 2 h and at RT overnight. 30 ml of water were added to the reaction mixture. The precipitate was filtered off and washed with water.

Yield: 1.16 g (91% of theory)

LC-MS (Method 3): $R_t$=2.12 min; MS (ESIpos): m/z=403 [M+H]$^+$.

$^1$H NMR (400 MHz, DMSO-d$_6$): δ=8.80 (q, 1H), 8.66 (d, 1H), 8.30-8.00 (br s, 2H), 8.08 (s, 1H), 7.66-7.61 (m, 3H), 7.43 (t, 2H), 5.62 (s, 2H), 2.82 (d, 3H).

Example 22

4-{[(6-Amino-3,5-dicyano-4-phenylpyridin-2-yl)oxy]methyl}-N-methylpyridine-2-carboxamide

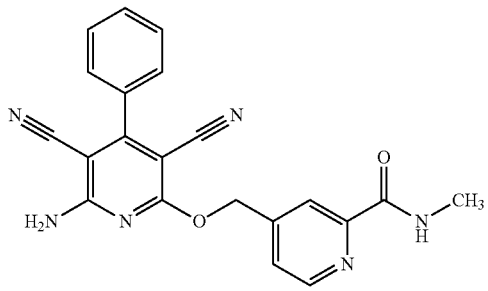 [SMILES: CNC(=O)c1cc(COc2nc(N)c(C#N)c(-c3ccccc3)c2C#N)ccn1]

The preparation was carried out analogously to Example 21 using Example 36A.

Yield: (59% of theory, 94% pure)

LC-MS (Method 3): $R_t$=2.08 min; MS (ESIpos): m/z=385 [M+H]$^+$.

Example 23

3-{[(3,5-Dicyano-6-{[(2R)-2,3-dihydroxypropyl]amino}-4-phenylpyridin-2-yl)sulfanyl]methyl}-benzenecarboxylic acid

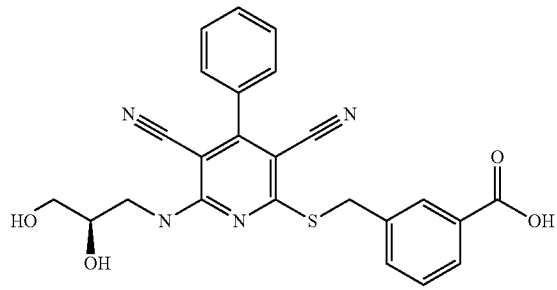 [SMILES: N#Cc1c(NC[C@@H](O)CO)nc(SCc2cccc(C(=O)O)c2)c(C#N)c1-c1ccccc1]

61.5 mg (0.15 mmol) of 3-{[(6-chloro-3,5-dicyano-4-phenylpyridin-2-yl)sulfanyl]methyl}benzenecarboxylic acid (Example 72A) were initially charged in 1.6 ml of THF. After addition of 27.6 mg (0.30 mmol) of (2R)-3-aminopropane-1,2-diol, the mixture was stirred at RT overnight. 2 ml of water were added, and the reaction mixture was purified by preparative HPLC (Chromasil, water/acetonitrile+0.1% trifluoroacetic acid).

Yield: 52 mg (75% of theory)

LC-MS (Method 3): $R_t$=2.21 min; MS (ESIpos): m/z=461 [M+H]$^+$.

$^1$H NMR (400 MHz, DMSO-d$_6$): δ=13.07-12.98 (br s, 1H), 8.05 (s, 1H), 7.91 (t, 1H), 7.85 (d, 1H), 7.72 (d, 1H), 7.60-7.51 (m, 5H), 7.47 (t, 1H), 4.96-4.92 (br s, 1H), 4.75-4.69 (br s, 1H), 4.65 (d, 2H), 3.81-3.70 (m, 2H), 3.52-3.44 (m, 1H), 3.43-3.35 (m, 2H).

Example 24

3-[({3,5-Dicyano-4-[4-(2-hydroxyethoxy)phenyl]-6-pyrrolidin-1-ylpyridin-2-yl}sulfanyl)methyl]-benzenecarboxylic acid

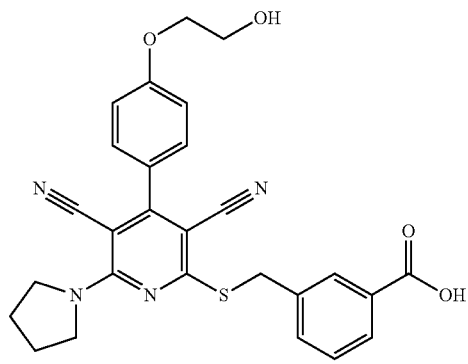 [SMILES: N#Cc1c(SCc2cccc(C(=O)O)c2)nc(N2CCCC2)c(C#N)c1-c1ccc(OCCO)cc1]

The preparation was carried out as described for Example 23 using the appropriate starting material (Example 74A).

Yield: (83% of theory)

LC-MS (Method 6): $R_t$=1.18 min; MS (ESIpos): m/z=501 [M+H]$^+$.

$^1$H NMR (400 MHz, DMSO-d$_6$): δ=13.03 (s, 1H), 8.06 (s, 1H), 7.84 (d, 1H), 7.70 (d, 1H), 7.51-7.44 (m, 3H), 7.09 (d, 2H), 4.94-4.88 (br s, 1H), 4.62 (s, 2H), 4.07 (t, 2H), 3.86-3.78 (m, 4H), 3.77-3.72 (m, 2H), 1.98-1.92 (m, 4H).

Example 25

4-[({6-Amino-3,5-dicyano-4-[4-(2-hydroxyethoxy)phenyl]pyridin-2-yl}sulfanyl)methyl]-N-methylpyridine-2-carboxamide

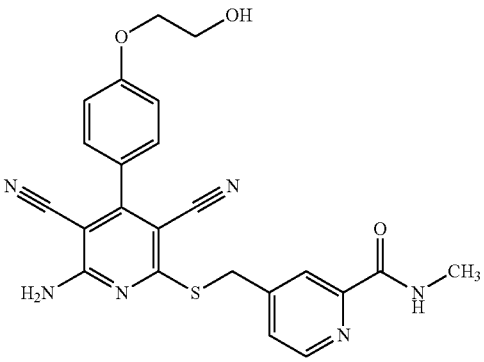 [SMILES: CNC(=O)c1cc(CSc2nc(N)c(C#N)c(-c3ccc(OCCO)cc3)c2C#N)ccn1]

50 mg (0.16 mmol) of 2-amino-4-[4-(2-hydroxyethoxy)phenyl]-6-sulfanylpyridine-3,5-dicarbonitrile (Example 10A), 38.9 mg (0.18 mmol) of 4-(chloromethyl)-N-methylpyridine-2-carboxamide hydrochloride (Example 41A) and 53.8 mg (0.64 mmol) of sodium bicarbonate were dissolved in 1 ml of DMF and the mixture was stirred at RT overnight. 30 ml of water were added to the reaction mixture, and the precipitate was filtered off. The precipitate was purified by preparative HPLC (Chromasil, water/acetonitrile+ 0.1% trifluoroacetic acid).

Yield: 57 mg (77% of theory)

LC-MS (Method 10): $R_t$=1.62 min; MS (ESIpos): m/z=461 [M+H]$^+$.

$^1$H NMR (400 MHz, DMSO-d$_6$): δ=8.75 (q, 1H), 8.54 (d, 1H), 8.30-7.85 (br s, 2H), 8.14 (s, 1H), 7.80-7.76 (m, 1H), 7.47 (d, 2H), 7.09 (d, 2H), 4.59 (s, 2H), 4.07 (t, 2H), 3.74 (t, 2H), 2.81 (d, 3H).

The examples listed in Table 7 are prepared from the appropriate starting materials analogously to Example 25.

TABLE 7

| Example No. | Structure (yield) | LC-MS: $R_t$ [min] (Method); MS (ESI): m/z [M + H]$^+$ | $^1$H NMR (DMSO-d$_6$): |
|---|---|---|---|
| 26 | (96% of theory) | 2.33 min (Method 3); m/z = 445 | δ = 8.75 (q, 1H), 8.55 (d, 1H), 8.25-7.90 (br s, 2H), 8.14, (s, 1H), 7.80-7.76 (m, 1H), 7.47 (d, 2H), 7.07 (d, 2H), 4.59 (s, 2H), 4.10 (q, 2H), 2.81 (d, 3H), 1.35 (t, 3H). |
| 27 | (82% of theory) | 2.23 min (Method 3); m/z = 449 | δ = 8.74 (q, 1H), 8.55 (d, 1H), 8.35-8.00 (br s, 2H), 8.15 (s, 1H), 7.80-7.76 (m, 1H), 7.45-7.37 (m, 2H), 7.14-7.09 (m, 1H), 4.60 (s, 2H), 3.85 (s, 3H), 2.81 (d, 3H). |
| 28 | (48% of theory) | 1.68 min (Method 4); m/z = 430 | δ = 8.75 (q, 1H), 8.54 (d, 1H), 8.13 (s, 1H), 8.10-7.85 (br s, 2H), 7.79-7.75 (m, 1H), 7.30 (d, 2H), 6.63 (d, 2H), 4.58 (s, 2H), 2.82 (d, 3H), 2.74 (s, 3H). |

TABLE 7-continued
| Example No. | Structure (yield) | LC-MS: $R_t$ [min] (Method); MS (ESI): m/z [M + H]+ | 1H NMR (DMSO-d6): |
|---|---|---|---|
| 29 | 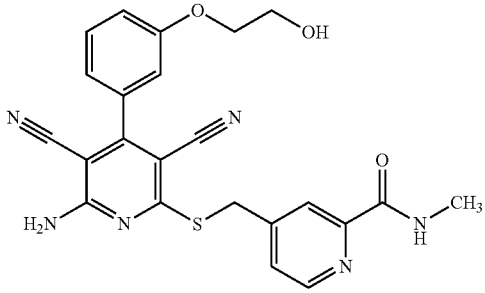 [SMILES: CNC(=O)c1cc(CSc2nc(N)c(C#N)c(-c3cccc(OCCO)c3)c2C#N)ccn1]<br>(70% of theory) | 0.96 min (Method 6); m/z = 461 | δ = 8.75 (q, 1H), 8.55 (d, 1H), 8.35-7.90 (br s, 2H), 8.15 (s, 1H), 7.80-7.76 (m, 1H), 7.44 (t, 1H), 7.14-7.06 (m, 3H), 4.95-4.85 (br s, 1H), 4.60 (s, 2H), 4.02 (t, 2H), 3.76-3.70 (m, 2H), 2.82 (d, 3H). |
| 30 | 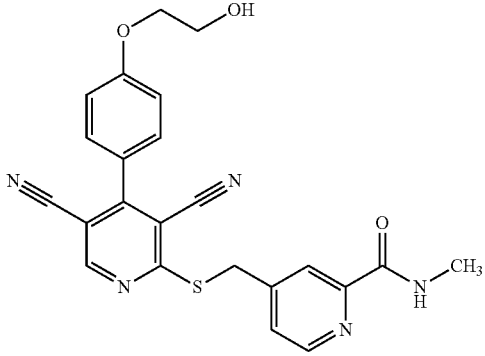 [SMILES: CNC(=O)c1cc(CSc2ncc(C#N)c(-c3ccc(OCCO)cc3)c2C#N)ccn1]<br>(97% of theory) | 2.16 min (Method 3); m/z = 446 | δ = 9.14 (s, 1H), 8.81-8.73 (m, 1H), 8.57 (d, 1H), 8.14 (s, 1H), 7.70-7.66 (m, 1H), 7.61 (d, 2H), 7.17 (d, 2H), 4.74 (s, 2H), 4.10 (t, 2H), 3.75 (t, 2H), 2.81 (d, 3H). |
| 31 | 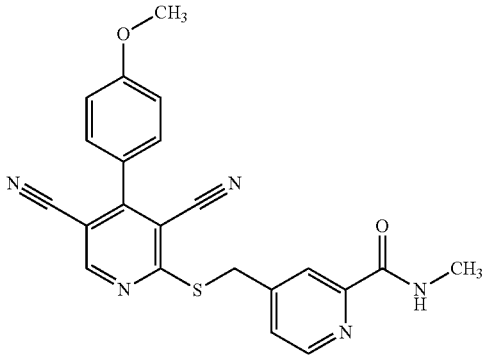 [SMILES: CNC(=O)c1cc(CSc2ncc(C#N)c(-c3ccc(OC)cc3)c2C#N)ccn1]<br>(90% of theory) | 1.16 min (Method 6); m/z = 416 | δ = 9.14 (s, 1H), 8.81-8.71 (m, 1H), 8.56 (d, 1H), 8.14 (s, 1H), 7.70-7.66 (m, 1H), 7.63 (d, 2H), 7.17 (d, 2H), 4.74 (s, 2H), 3.86 (s, 3H), 2.81 (d, 3H). |
| 32 | 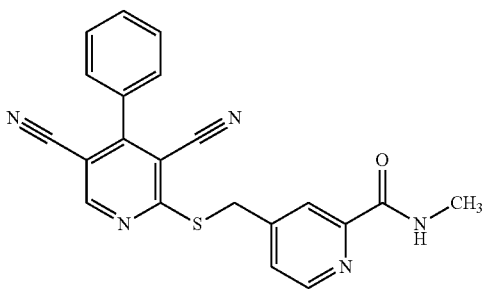 [SMILES: CNC(=O)c1cc(CSc2ncc(C#N)c(-c3ccccc3)c2C#N)ccn1]<br>(98% of theory) | 1.14 min (Method 6); m/z = 386 | δ = 9.19 (s, 1H), 8.84-8.72 (m, 1H), 8.58 (d, 1H), 8.15 (s, 1H), 7.76-7.55 (m, 6H), 4.75 (s, 2H), 2.81 (d, 3H). |

TABLE 7-continued
| Example No. | Structure (yield) | LC-MS: R_t [min] (Method); MS (ESI): m/z [M + H]+ | 1H NMR (DMSO-d_6): |
|---|---|---|---|
| 33 | 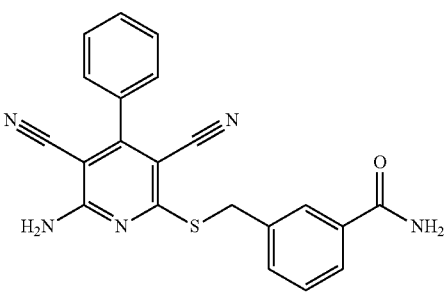 [SMILES: N#Cc1c(N)nc(SCc2cccc(C(N)=O)c2)c(C#N)c1-c1ccccc1]<br>(72% of theory) | 3.19 min (Method 5); m/z = 386 | δ = 8.42-7.94 (br s, 2H), 8.00 (s, 1H), 7.96 (s, 1H), 7.77 (d, 1H), 7.69 (d, 1H), 7.57-7.49 (m, 5H), 7.43-7.38 (m, 2H), 4.55 (s, 2H). |
| 34 | 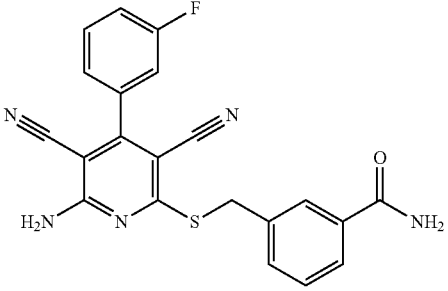 [SMILES: N#Cc1c(N)nc(SCc2cccc(C(N)=O)c2)c(C#N)c1-c1cccc(F)c1]<br>(54% of theory) | 3.24 min (Method 5); m/z = 404 | δ = 8.45-7.96 (br s, 2H), 8.00 (s, 1H), 7.95 (s, 1H), 7.76 (d, 1H), 7.69 (d, 1H), 7.64-7.57 (m, 1H), 7.50-7.34 (m, 5H), 4.55 (s, 2H). |
| 35 | 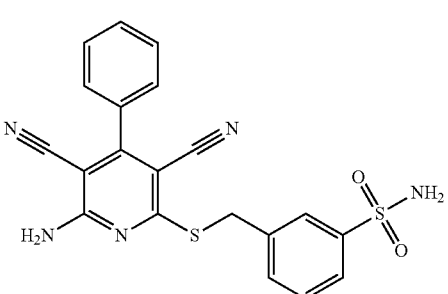<br>(75% of theory) | 1.76 min (Method 4); m/z = 422 | δ = 8.26-8.02 (br s, 2H), 7.96 (s, 1H), 7.81 (d, 1H), 7.71 (d, 1H), 7.59-7.47 (m, 6H), 7.37 (s, 2H), 4.59 (s, 2H). |
| 36 | 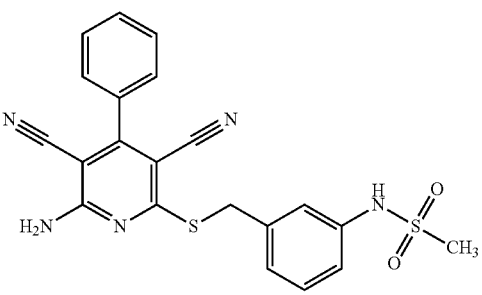 [SMILES: CS(=O)(=O)Nc1cccc(CSc2nc(N)c(C#N)c(-c3ccccc3)c2C#N)c1]<br>(75% of theory)<br>*20 | 2.31 min (Method 3); m/z = 436 | δ = 9.75 (s, 1H), 8.20-7.95 (br s, 2H), 7.60-7.48 (m, 5H), 7.34-7.21 (m, 3H), 7.12 (d, 1H), 4.49 (s, 2H), 3.00 (s, 3H). |

TABLE 7-continued
| Example No. | Structure (yield) | LC-MS: R*t* [min] (Method); MS (ESI): m/z [M + H]+ | 1H NMR (DMSO-d6): |
|---|---|---|---|
| 37 | 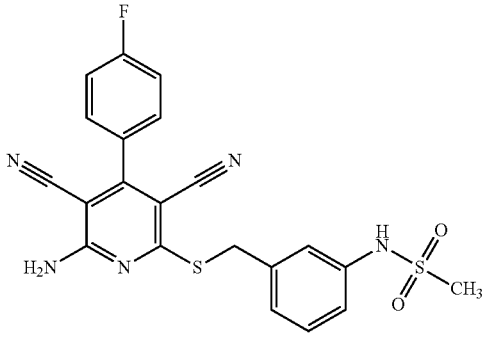 [SMILES: CS(=O)(=O)Nc1cccc(CSc2nc(N)c(C#N)c(-c3ccc(F)cc3)c2C#N)c1]<br>(30% of theory)<br>*20 | 2.37 min (Method 3); m/z = 454 | δ = 9.74 (s, 1 H), 8.17-7.96 (br s, 2H), 7.66-7.56 (m, 2H), 7.46-7.36 (m, 2H), 7.33-7.23 (m, 3H), 7.11 (d, 1H), 4.48 (s, 2H), 3.00 (s, 3H). |
| 38 | 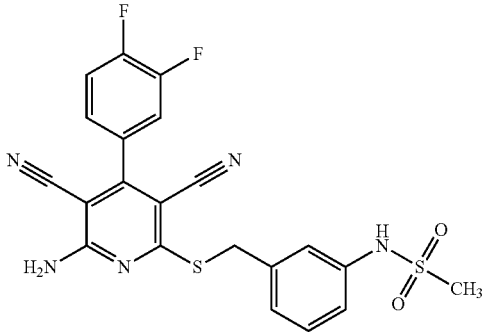 [SMILES: CS(=O)(=O)Nc1cccc(CSc2nc(N)c(C#N)c(-c3ccc(F)c(F)c3)c2C#N)c1]<br>(54% of theory)<br>*20 | 2.42 min (Method 3); m/z = 472 | δ = 9.74 (s, 1 H), 8.20-8.00 (br s, 2H), 7.82-7.75 (m, 1H), 7.71-7.62 (m, 1H), 7.47-7.41 (m, 1H), 7.32-7.24 (m, 3H), 7.13-7.09 (m, 1H), 4.48 (s, 2H), 3.00 (s, 3H). |
| 39 | 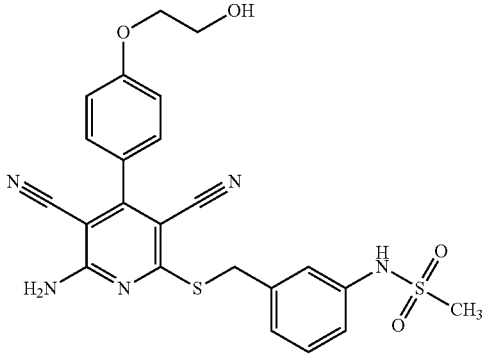 [SMILES: CS(=O)(=O)Nc1cccc(CSc2nc(N)c(C#N)c(-c3ccc(OCCO)cc3)c2C#N)c1]<br>(74% of theory)<br>*20 | 1.60 min (Method 4); m/z = 496 | δ = 9.74 (s, 1H), 8.07-7.94 (br s, 2H), 7.46 (d, 2H), 7.33-7.22 (m, 3H), 7.15-7.07 (m, 3H), 4.46 (s, 2H), 4.07 (t, 2H), 3.74 (t, 2H), 3.00 (s, 3H). |

TABLE 7-continued

| Example No. | Structure (yield) | LC-MS: $R_t$ [min] (Method); MS (ESI): m/z [M + H]$^+$ | $^1$H NMR (DMSO-$d_6$): |
|---|---|---|---|
| 40 | 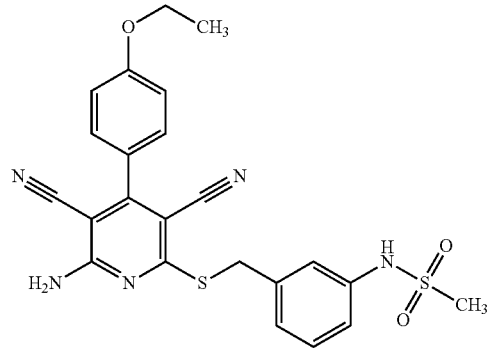 [SMILES: CCOc1ccc(-c2c(C#N)c(N)nc(SCc3cccc(NS(C)(=O)=O)c3)c2C#N)cc1]<br>(67% of theory)<br>*20 | 1.24 min (Method 6); m/z = 480 | δ = 9.74 (s, 1H), 8.08-7.93 (br s, 2H), 7.47 (d, 2H), 7.32-7.22 (m, 3H), 7.15-7.04 (m, 3H), 4.47 (s, 2H), 4.11 (q, 2H), 3.00 (s, 3H), 1.36 (t, 3H). |
| 41 | 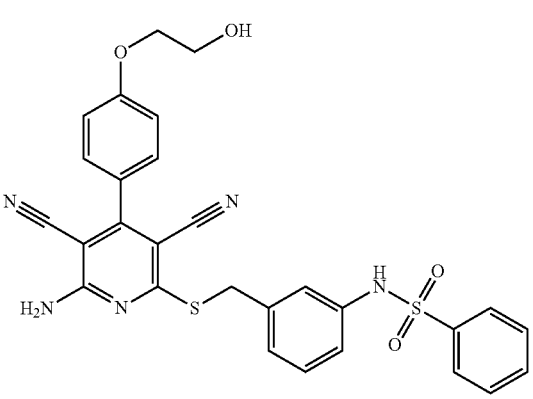 [SMILES: N#Cc1c(N)nc(SCc2cccc(NS(=O)(=O)c3ccccc3)c2)c(C#N)c1-c1ccc(OCCO)cc1]<br>(78% of theory)<br>*20 | 1.13 min (Method 6); m/z = 558 | δ = 10.29 (s, 1H), 8.06-7.94 (br s, 2H), 7.73 (d, 2H), 7.62-7.55 (m, 1H), 7.54-7.44 (m, 4H), 7.24-7.07 (m, 5H), 7.01-6.93 (m, 1H), 4.96-4.86 (m, 1H), 4.40 (s, 2H), 4.08 (t, 2H), 3.78-3.69 (m, 2H). |

*20 Different reaction time: 2 h, RT.

Example 42

4-[({6-Amino-4-[4-(2-amino-2-oxoethoxy)phenyl]-3,5-dicyanopyridin-2-yl}sulfanyl)methyl]-N-methylpyridine-2-carboxamide

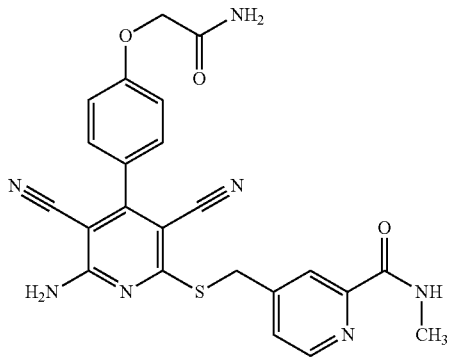 [SMILES: CNC(=O)c1cc(CSc2nc(N)c(C#N)c(-c3ccc(OCC(N)=O)cc3)c2C#N)ccn1]

20 mg (0.2 mmol) of cyanothioacetamide were dissolved in 600 μl of ethanol and added to 17.9 mg (0.1 mmol) of 2-(4-formylphenoxy)acetamide, and 20.2 mg (0.2 mmol) of 4-methylmorpholine were added. The reaction solution was shaken at 70° C. overnight, the solvent was evaporated and 24.3 mg (0.11 mmol) of 4-(chloromethyl)-N-methylpyridine-2-carboxamide hydrochloride (Example 41A) and 33.6 mg (0.4 mmol) of sodium bicarbonate were added to the residue. The reaction solution was shaken at RT overnight and then filtered, and the filtrate was purified by preparative HPLC (Phenomenex Luna C18(2), water/acetonitrile+0.1% formic acid).

Yield: 5.1 mg (11% of theory)

LC-MS (Method 11): $R_t$=1.83 min; MS (ESIpos): m/z=474 [M+H]$^+$.

The examples listed in Table 8 are prepared from the appropriate starting materials analogously to Example 42.

TABLE 8
| Example No. | Structure (yield) | LC-MS: $R_t$ [min] (Method); MS (ESI): m/z [M + H]+ |
|---|---|---|
| 43 | 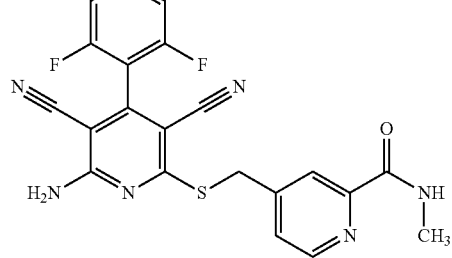 (26% of theory) | 2.02 min (Method 11); m/z = 437 |
| 44 | 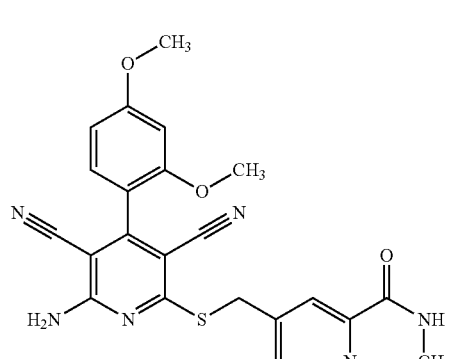 (26% of theory) | 2.03 min (Method 11); m/z = 461 |
| 45 | 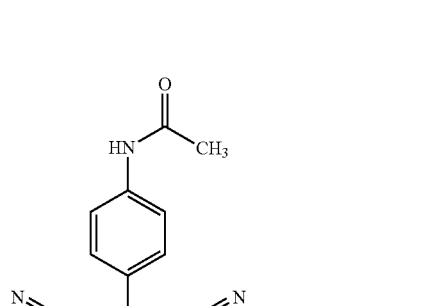 (5.7% of theory) | 1.86 min (Method 11); m/z = 458 |

TABLE 8-continued

| Example No. | Structure (yield) | LC-MS: R$_t$ [min] (Method); MS (ESI): m/z [M + H]$^+$ |
|---|---|---|
| 46 | (21% of theory) | 2.06 min (Method 11); m/z = 524 |
| 47 | (9% of theory) | 1.94 min (Method 11); m/z = 484 |
| 48 | (6.6% of theory) | 2.11 min (Method 11); m/z = 502 |

TABLE 8-continued

| Example No. | Structure (yield) | LC-MS: R_t [min] (Method); MS (ESI): m/z [M + H]+ |
|---|---|---|
| 49 | (9.6% of theory) | 2.17 min (Method 11); m/z = 459 |
| 50 | (10% of theory) | 2.15 min (Method 11); m/z = 487 |
| 51 | (9.6% of theory) | 2.06 min (Method 11); m/z = 437 |
| 52 | (7.3% of theory) | 2.08 min (Method 11); m/z = 455 |

TABLE 8-continued

| Example No. | Structure (yield) | LC-MS: $R_t$ [min] (Method); MS (ESI): m/z [M + H]$^+$ |
|---|---|---|
| 53 | 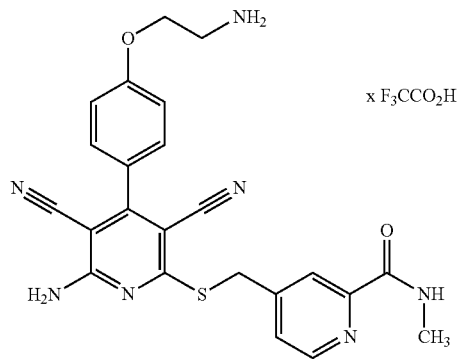<br>(21% of theory) | 2.07 min (Method 11); m/z = 437 |

Example 54

4-[({6-Amino-4-[4-(2-aminoethoxy)phenyl]-3,5-dicyanopyridin-2-yl}sulfanyl)methyl]-N-methylpyridine-2-carboxamide trifluoroacetate 413 mg (0.74 mmol) of tert-butyl (2-{4-[2-amino-3,5-dicyano-6-({[2-(methylcarbamoyl)pyridin-4-yl]methyl}sulfanyl)pyridin-4-yl]phenoxy}ethyl)carbamate (Example 45A) were dissolved in 4.3 ml of dichloromethane. After addition of 4.2 g (6.88 mmol) of trifluoroacetic acid, the mixture was stirred at RT for 2.5 h. The reaction mixture was evaporated. The residue was purified by preparative HPLC (Chromasil, water/acetonitrile+0.1% trifluoroacetic acid).

Yield: 497 mg (100% of theory)

LC-MS (Method 6): $R_t$=0.77 min; MS (ESIpos): m/z=460 [M+H]$^+$.

$^1$H NMR (400 MHz, DMSO-d$_6$): δ=8.75 (q, 1H), 8.55 (d, 1H), 8.40-7.85 (br s, 2H), 8.14 (s, 1H), 8.00-7.92 (m, 2H), 7.80-7.76 (m, 1H), 7.52 (d, 2H), 7.14 (d, 2H), 4.59 (s, 2H), 4.25 (t, 2H), 3.31-3.23 (m, 2H), 2.81 (d, 3H).

Example 55

4-{[(4-{4-[2-(L-Alanylamino)ethoxy]phenyl}-6-amino-3,5-dicyanopyridin-2-yl)sulfanyl]methyl}-N-methylpyridine-2-carboxamide trifluoroacetate The preparation was carried out as described in Example 54 using the starting material Example 58A.

Yield: (80% of theory)

LC-MS (Method 3): $R_t$=1.38 min; MS (ESIpos): m/z=531 [M+H]$^+$.

$^1$H NMR (400 MHz, DMSO-d$_6$): δ=8.75 (q, 1H), 8.65 (t, 1H), 8.55 (d, 1H), 8.17-8.00 (br s, 2H), 8.14 (s, 1H), 8.06-8.02 (m, 2H), 7.79-7.76 (m, 1H), 7.49 (d, 2H), 7.10 (d, 2H), 4.59 (s, 2H), 4.16-4.10 (m, 2H), 3.86-3.77 (m, 2H), 3.59-3.51 (m, 1H), 2.81 (d, 3H), 1.33 (d, 3H).

Example 56 rac-4-[1-({6-Amino-3,5-dicyano-4-[4-(2,2,2-trifluoroethoxy)phenyl]pyridin-2-yl}sulfanyl)ethyl]-N-methylpyridine-2-carboxamide

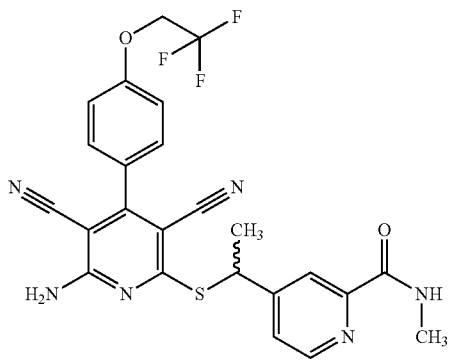 [SMILES: CNC(=O)c1cc(C(C)Sc2nc(N)c(C#N)c(-c3ccc(OCC(F)(F)F)cc3)c2C#N)ccn1]

41.5 mg (0.118 mmol) of 2-amino-6-sulfanyl-4-[4-(2,2,2-trifluoroethoxy)phenyl]pyridine-3,5-dicarbonitrile (Example 16), 37 mg (0.118 mmol) of 4-(1-chloroethyl)-N-methylpyridine-2-carboxamide Example 44A and 39.8 mg (0.473 mmol) of sodium bicarbonate were dissolved in 0.4 ml of DMF and the mixture was stirred at RT overnight. Water/tetrahydrofuran was added to the reaction solution in such an amount that a clear solution was formed. The solution was purified by preparative HPLC (Chromasil, water/acetonitrile+0.1% trifluoroacetic acid).

Yield: 37 mg (61% of theory)

LC-MS (Method 4): $R_t$=2.10 min; MS (ESIpos): m/z=513 [M+H]+.

$^1$H NMR (400 MHz, DMSO-$d_6$): δ=8.80-8.70 (m, 1H), 8.57 (d, 1H), 8.20-8.00 (br s, 2H), 8.18-8.15 (m, 1H), 7.86-7.83 (m, 1H), 7.50 (d, 2H), 7.22 (d, 2H), 5.30-5.19 (m, 1H), 4.92-4.81 (m, 2H), 2.82 (d, 3H), 1.74 (d, 3H).

Example 57

4-[1-({6-Amino-3,5-dicyano-4-[4-(2,2,2-trifluoroethoxy)phenyl]pyridin-2-yl}sulfanyl)ethyl]-N-methylpyridine-2-carboxamide (Enantiomer B)

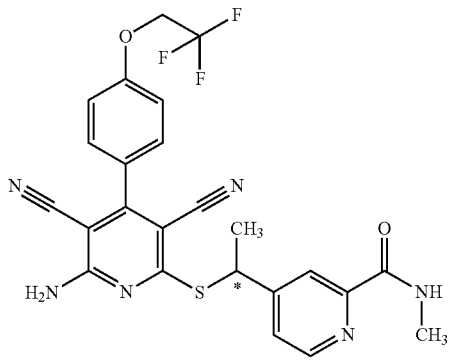 [SMILES: CNC(=O)c1cc(C(C)Sc2nc(N)c(C#N)c(-c3ccc(OCC(F)(F)F)cc3)c2C#N)ccn1]

By preparative separation on a chiral phase, the compound Example 56 rac-4-[1-({6-amino-3,5-dicyano-4-[4-(2,2,2-trifluoroethoxy)phenyl]pyridin-2-yl}sulfanyl)ethyl]-N-methylpyridine-2-carboxamide (37 mg) was separated into the enantiomers [column: Daicel Chiralcel OD-H, 5 μm, 250×20 mm, mobile phase: 50% isohexane, 50% ethanol, flow rate 15 ml/min; 40° C., detection: 220 nm]

Yield: 14.8 mg (>99% pure, >99% ee)

Enantiomer B: $R_t$=6.205 min [Chiralcel OD-H, 5 μm, 250×4.6 nm; mobile phase: 60% ethanol, 40% isohexane; flow rate 1.0 ml/min; 40° C.; detection: 220 nm].

Example 58 rac-N-{3-[1-({6-Amino-3,5-dicyano-4-[4-(2,2,2-trifluoroethoxy)phenyl]pyridin-2-yl}sulfanyl)-ethyl]phenyl}methanesulfonamide

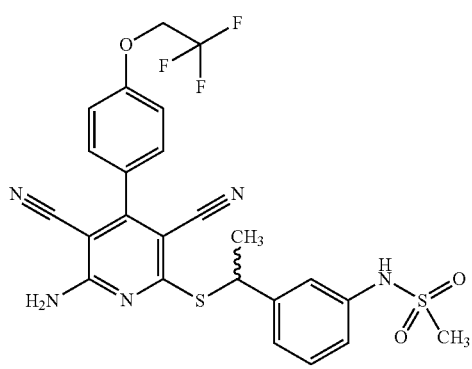 [SMILES: CC(Sc1nc(N)c(C#N)c(-c2ccc(OCC(F)(F)F)cc2)c1C#N)c1cccc(NS(C)(=O)=O)c1]

The preparation was carried out as described in Example 56 using the appropriate starting materials in Example 16A and Example 88A.

Yield: (38% of theory)

LC-MS (Method 3): $R_t$=2.58 min; MS (ESIpos): m/z=548 [M+H]+.

$^1$H NMR (400 MHz, DMSO-$d_6$): δ=9.76 (s, 1H), 8.06-7.93 (br s, 2H), 7.52 (d, 2H), 7.35-7.26 (m, 3H), 7.22 (d, 2H), 7.14 (d, 1H), 5.17-5.09 (m, 1H), 4.92-4.82 (, 2H), 3.00 (s, 3H), 1.71 (d, 3H).

Example 59

N-{3-[1-({6-Amino-3,5-dicyano-4-[4-(2,2,2-trifluoroethoxy)phenyl]pyridin-2-yl}sulfanyl)ethyl]-phenyl}methanesulfonamide (Enantiomer B)

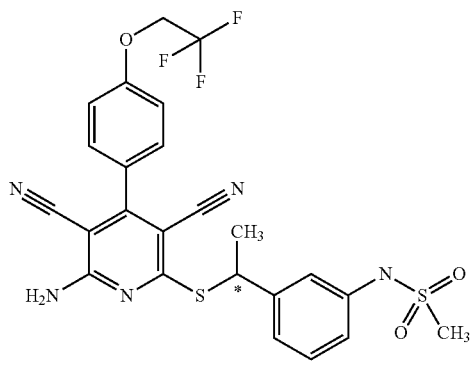 [SMILES: CC(Sc1nc(N)c(C#N)c(-c2ccc(OCC(F)(F)F)cc2)c1C#N)c1cccc(NS(C)(=O)=O)c1]

By preparative separation on a chiral phase, the compound rac-N-{3-[1-({6-amino-3,5-dicyano-4-[4-(2,2,2-trifluoroethoxy)phenyl]pyridin-2-yl}sulfanyl)ethyl]phenyl}methanesulfonamide (Example 58) (190 mg) was separated into the enantiomers [column: Daicel Chiralcel AD-H, 5 µm, 250×20 mm, mobile phase: 50% isohexane, 50% ethanol, flow rate 15 ml/min; 40° C., detection: 220 nm].

Yield: 65 mg (>99% pure, >99% ee)

Enantiomer B: $R_t$=7.645 min [Chiralcel AD-H, 5 µm, 250×4.6 nm; mobile phase: 50% ethanol, 50% isohexane; flow rate 1.0 ml/min; 40° C.; detection: 220 nm].

Example 60 rac-3-[1-({6-Amino-3,5-dicyano-4-[4-(2-hydroxyethoxy)phenyl]pyridin-2-yl}sulfanyl)ethyl]-benzenecarboxamide

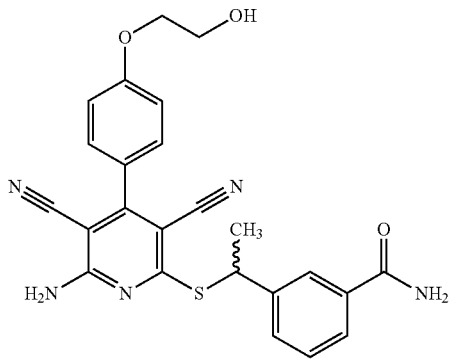 [SMILES: CC(Sc1nc(N)c(C#N)c(-c2ccc(OCCO)cc2)c1C#N)c1cccc(C(N)=O)c1]

33 mg (0.072 mmol) of rac-3-[(1S)-1-({6-amino-3,5-dicyano-4-[4-(2-hydroxyethoxy)phenyl]-pyridin-2yl}sulfanyl)ethyl]benzenecarboxylic acid Example 16 were initially charged in 1.6 ml of DMF. After addition of 20.6 mg (0.107 mmol) of EDC and 14.5 mg (0.107 mmol) of HOBT, the mixture was stirred at RT for 10 min. 19.2 mg (0.358 mmol) of ammonium chloride and 64.8 mg (0.502 mmol) of N,N-diisopropylethylamine were then added, and the reaction solution was stirred at RT overnight. The reaction solution was purified by preparative HPLC (Chromasil, water/acetonitrile).

Yield: 24.3 mg (74% of theory)

LC-MS (Method 6): $R_t$=0.98 min; MS (ESIpos): m/z=460 [M+H]$^+$.

$^1$H NMR (400 MHz, DMSO-d$_6$): δ=8.25-7.85 (br s, 2H), 8.07-7.97 (m, 2H), 7.76 (dd, 2H), 7.49-7.38 (m, 4H), 7.08 (d, 2H), 5.23 (q, 1H), 4.90 (t, 1H), 4.06 (t, 2H), 3.73 (q, 2H), 1.75 (d, 3H).

Example 61

3-[1-({6-Amino-3,5-dicyano-4-[4-(2-hydroxyethoxy)phenyl]pyridin-2-yl}sulfanyl)ethyl]benzenecarboxamide (Enantiomer A)

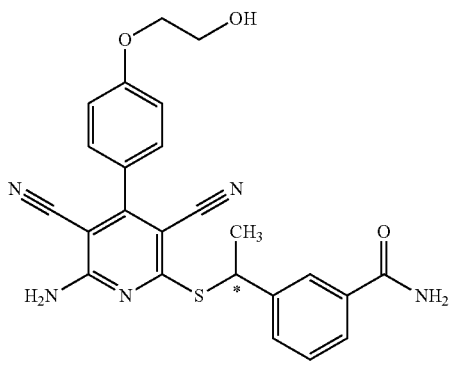 [SMILES: CC(Sc1nc(N)c(C#N)c(-c2ccc(OCCO)cc2)c1C#N)c1cccc(C(N)=O)c1]

The preparation was carried out as described in Example 60 using the appropriate starting material (Example 17).

Yield: (82% of theory)

LC-MS (Method 4): $R_t$=1.49 min; MS (ESIpos): m/z=460 [M+H]$^+$.

$^1$H NMR (400 MHz, DMSO-d$_6$): δ=8.25-7.90 (br s, 2H), 8.09-7.96 (m, 2H), 7.76 (dd, 2H), 7.49-7.35 (m, 4H), 7.08 (d, 2H), 5.25 (q, 1H), 4.91 (br s, 1H), 4.06 (t, 3H), 3.73 (br s, 3H), 1.75 (d, 3H).

Example 62 rac-3-[1-({6-Amino-3,5-dicyano-4-[4-(2-hydroxyethoxy)phenyl]pyridin-2-yl}sulfanyl)ethyl]-N-methylbenzenecarboxamide

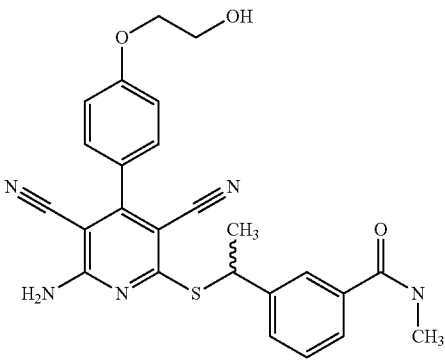 [SMILES: CNC(=O)c1cccc(C(C)Sc2nc(N)c(C#N)c(-c3ccc(OCCO)cc3)c2C#N)c1]

33 mg (0.072 mmol) of rac-3-[(1S)-1-({6-amino-3,5-dicyano-4-[4-(2-hydroxyethoxy)phenyl]-pyridin-2yl}sulfanyl) ethyl]benzenecarboxylic acid (Example 16) were initially charged in 0.66 ml of DMF. At 0° C., 54.5 mg (0.143 mmol) of HATU were added, and the reaction solution was stirred at 0° C. for 20 min. After addition of 6.7 mg (0.215 mmol) of methylamine (2N in tetrahydrofuran) and 18.5 mg (0.143 mmol) of N,N-diisopropylethylamine, the mixture was stirred at RT overnight. The reaction solution was purified by preparative HPLC (Chromasil, water/acetonitrile).

Yield: 27.3 mg (80% of theory)

LC-MS (Method 6): $R_t$=1.02 min; MS (ESIpos): m/z=474 [M+H]$^+$.

1H NMR (400 MHz, DMSO-d6): δ=8.52-8.38 (m, 1H), 8.30-7.80 (br s, 2H), 7.99 (s, 1H), 7.74 (d, 2H), 7.52-7.31 (m, 3H), 7.09 (d, 2H), 5.22 (q, 1H), 4.91 (t, 1H), 4.06 (t, 2H), 3.73 (q, 2H), 2.79 (d, 3H), 1.76 (d, 3H).

Example 63

3-[1-({6-Amino-3,5-dicyano-4-[4-(2-hydroxyethoxy)phenyl]pyridin-2-yl}sulfanyl)ethyl]-N-methylbenzenecarboxamide (Enantiomer A)

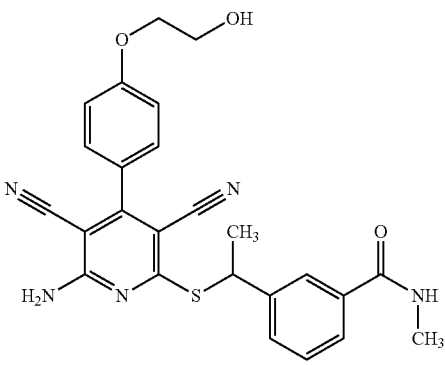 [SMILES: CNC(=O)c1cccc(C(C)Sc2nc(N)c(C#N)c(-c3ccc(OCCO)cc3)c2C#N)c1]

The preparation was carried out as described in Example 62 using the appropriate starting material (Example 17).

Yield: (34% of theory)

LC-MS (Method 4): $R_t$=1.57 min; MS (ESIpos): m/z=474 [M+H]$^+$.

$^1$H NMR (400 MHz, DMSO-d$_6$): δ=8.51-8.41 (m, 1H), 8.30-7.80 (br s, 2H), 7.98 (s, 1H), 7.73 (d, 2H), 7.50-7.36 (m, 3H), 7.08 (d, 2H), 5.22 (q, 1H), 4.89 (t, 1H), 4.06 (t, 2H), 3.73 (q, 2H), 2.79 (d, 3H), 1.75 (d, 3H).

Example 64

3-[1-({6-Amino-3,5-dicyano-4-[4-(2-methoxyethoxy)phenyl]pyridin-2-yl}sulfanyl)ethyl]benzenecarboxamide (Enantiomer A)

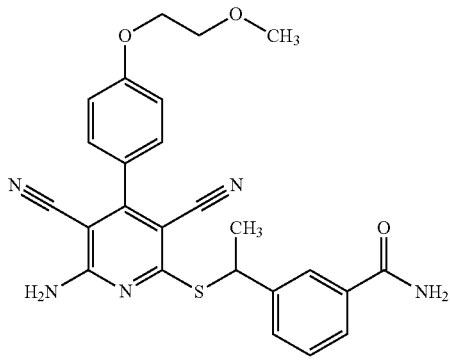 [SMILES: COCCOc1ccc(-c2c(C#N)c(N)nc(SC(C)c3cccc(C(N)=O)c3)c2C#N)cc1]

The preparation was carried out as described in Example 60 using the appropriate starting material (Example 19).

Yield: (82% of theory)

LC-MS (Method 6): $R_t$=1.12 min; MS (ESIpos): m/z=474 [M+H]$^+$.

$^1$H NMR (400 MHz, DMSO-d$_6$): δ=8.17-7.90 (br s, 2H), 8.04 (d, 2H), 7.82-7.68 (m, 2H), 7.50-7.36 (m, 4H), 7.09 (d, 2H), 5.21 (q, 1H), 4.17 (t, 2H), 3.68 (t, 2H), 3.32 (s, 3H), 1.75 (d, 3H).

Example 65

3-{[(3,5-Dicyano-4-phenylpyridin-2-yl)sulfanyl]methyl}benzenecarboxamide

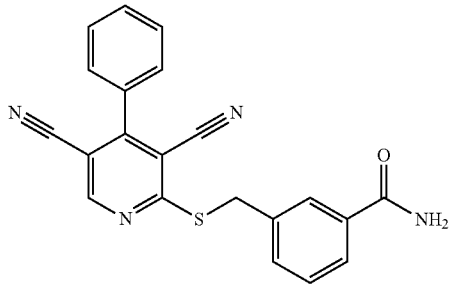 [SMILES: N#Cc1cnc(SCc2cccc(C(N)=O)c2)c(C#N)c1-c1ccccc1]

The preparation was carried out as described in Example 60 using the appropriate starting material (Example 15).

Yield: (83% of theory)

LC-MS (Method 4): $R_t$=1.79 min; MS (ESIpos): m/z=371 [M+H]$^+$.

$^1$H NMR (400 MHz, DMSO-d$_6$): δ=9.23 (s, 1H), 7.98 (s, 2H), 7.78 (d, 1H), 7.68-7.59 (m, 6H), 7.46-7.38 (m, 2H), 4.70 (s, 2H).

Example 66

3-{[(3,5-Dicyano-4-phenylpyridin-2-yl)sulfanyl]methyl}-N-(2-hydroxyethyl)benzenecarboxamide

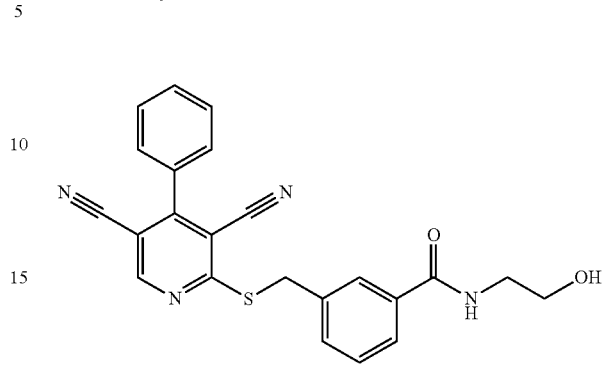

The preparation was carried out as described in Example 57A using the appropriate starting material (Example 15).

LC-MS (Method 6): $R_t$=1.09 min; MS (ESIpos): m/z=415 [M+H]$^+$.

$^1$H NMR (400 MHz, DMSO-d$_6$): δ=9.23 (s, 1H), 8.48-8.41 (m, 1H), 7.96 (s, 1H), 7.75 (d, 1H), 7.69-7.58 (m, 6H), 7.43 (t, 1H), 4.70 (s, 2H), 3.51 (t, 2H), 3.33 (q, 2H).

Example 67

4-[({6-Amino-3,5-dicyano-4-[4-(2-hydroxyethoxy)phenyl]pyridin-2-yl}oxy)methyl]-N-methylpyridine-2-carboxamide

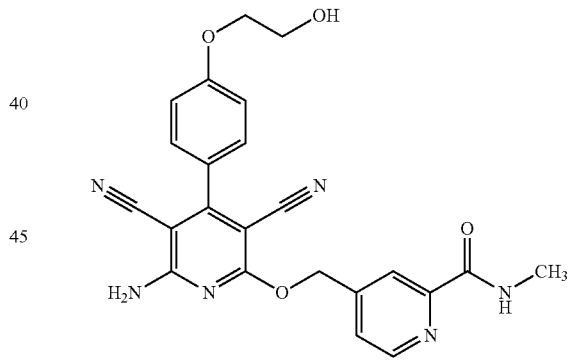

2.17 g (19.31 mmol) of potassium tert-butoxide were suspended in 20 ml of 1,2-dimethoxyethane. After addition of 1.7 g (7.72 mmol) of 4-(hydroxymethyl)-N-methylpyridine-2-carboxamide hydrochloride monohydrate (Example 41A) and 1.5 g (3.86 mmol) of Example 35A, the mixture was stirred at 60° C. overnight. Water was added to the reaction mixture until a precipitate was formed. The precipitate was filtered off and purified by preparative HPLC (Chromasil, water/acetonitrile+0.1% trifluoroacetic acid).

Yield: 638 mg (37% of theory)

LC-MS (Method 6): $R_t$=0.89 min; MS (ESIpos): m/z=445 [M+H]$^+$.

$^1$H NMR (400 MHz, DMSO-d$_6$): δ=8.80 (q, 1H), 8.66 (d, 1H), 8.15-7.80 (br s, 2H), 8.07 (s, 1H), 7.66-7.63 (m, 1H), 7.50 (d, 2H), 7.12 (d, 2H), 5.61 (s, 2H), 4.96-4.84 (m, 1H), 4.08 (t, 2H), 3.75 (t, 2H), 2.82 (d, 3H).

The examples listed in Table 9 were prepared from the appropriate starting materials analogously to Example 67.

TABLE 9

| Example No. | Structure (yield) | LC-MS: $R_t$ [min] (Method); MS (ESI): m/z [M + H]$^+$ | $^1$H NMR (DMSO-$d_6$): |
|---|---|---|---|
| 68 | 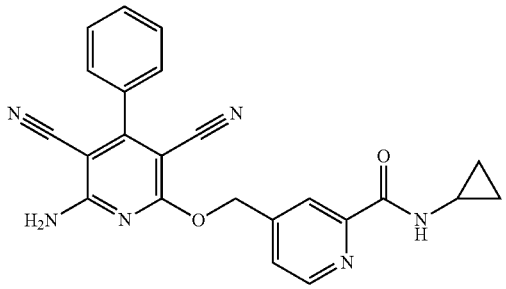 (81% of theory) | 2.20 min (Method 3); m/z = 411 | δ = 8.76 (d, 1H), 8.64 (d, 1H), 8.20-7.85 (br s, 2H), 8.07 (s, 1H), 7.67-7.63 (m, 1H), 7.60-7.53 (m, 5H), 5.62 (s, 2H), 2.95-2.87 (m, 1H), 0.72-0.65 (m, 4H). |
| 69 | 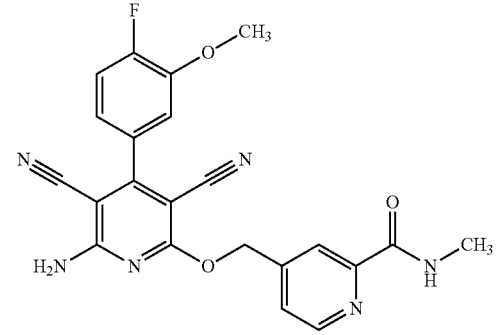 [SMILES: CNC(=O)c1cc(COc2nc(N)c(C#N)c(-c3ccc(F)c(OC)c3)c2C#N)ccn1] (18% of theory) | 1.07 min (Method 6); m/z = 433 | δ = 8.80 (q, 1H), 8.67 (d, 1H), 8.19-7.75 (br s, 2H), 8.08 (s, 1H), 7.67-7.63 (m, 1H), 7.47-7.40 (m, 2H), 7.17-7.12 (m, 1H), 5.62 (s, 2H), 3.88 (s, 3H), 2.81 (d, 3H). |

Example 70

4-({[3,5-Dicyano-6-(3-hydroxyazetidin-1-yl)-4-phenylpyridin-2-yl]sulfanyl}methyl)-N-methylpyridine-2-carboxamide

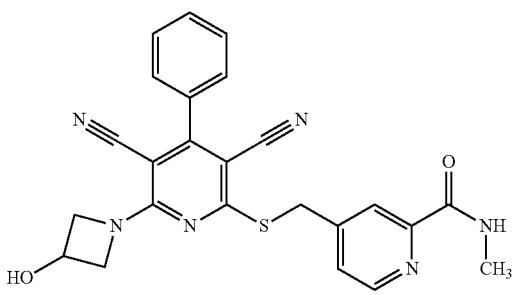

50 mg (0.12 mmol) of 4-{[(6-chloro-3,5-dicyano-4-phenylpyridin-2-yl)sulfanyl]methyl}-N-methylpyridine-2-carboxamide Example 75A, 19.6 mg (0.18 mmol) of azetidin-3-ol hydrochloride and 36.2 mg (0.36 mmol) of triethylamine were dissolved in 1 ml of tetrahydrofuran, and the mixture was stirred at RT for 1 h. Water and tetrahydrofuran were added to the reaction mixture until a solution had formed. The solution was purified by preparative HPLC (Chromasil, water/acetonitrile+0.1% trifluoroacetic acid).

Yield: 49.3 mg (91% of theory)

LC-MS (Method 6): $R_t$=1.08 min; MS (ESIpos): m/z=457 [M+H]$^+$.

$^1$H NMR (400 MHz, DMSO-$d_6$): δ=8.78 (q, 1H), 8.58 (d, 1H), 8.15-8.13 (m, 1H), 7.67-7.64 (m, 1H), 7.58-7.53 (m, 3H), 7.53-7.48 (m, 2H), 4.65-4.53 (m, 5H), 4.17-4.04 (m, 2H), 2.82 (d, 3H).

The examples listed in Table 10 were prepared from the appropriate starting materials analogously to Example 70.

TABLE 10

| Example No. | Structure (yield) | LC-MS: R_t [min] (Method); MS (ESI): m/z [M + H]+ | 1H NMR (DMSO-d6): |
|---|---|---|---|
| 71 | (72% of theory) *22 | 2.20 min (Method 3); m/z = 475 | δ = 8.79 (q, 1H), 8.58 (d, 1H), 8.14 (s, 1H), 7.67-7.64 (m, 1H), 7.63-7.57 (m, 2H), 7.41 (t, 2H), 5.94-5.88 (br s, 1H), 4.64-4.54 (m, 5H), 4.16-4.04 (m, 2H), 2.82 (d, 3H). |
| 72 | (61% of theory) *22 | 1.74 min (Method 4); m/z = 487 | δ = 8.78 (q, 1H), 8.58 (d, 1H), 8.13 (s, 1H), 7.66-7.63 (m, 1H), 7.47 (d, 2H), 7.09 (d, 2H), 5.94-5.83 (br s, 1H), 4.65-4.52 (m, 5H), 4.15-4.04 (m, 2H), 3.83 (s, 3H), 2.82 (d, 3H). |
| 73 | (99% of theory) | 1.03 min (Method 6); m/z = 487 | δ = 8.77 (q, 1H), 8.58 (d, 1H), 8.13 (s, 1H), 7.68-7.64 (m, 1H), 7.58-7.52 (m, 5H), 5.36-5.26 (m, 2H), 4.68 (s, 2H), 4.10-3.97 (m, 2H), 3.81-3.60 (m, 2H), 2.82 (d, 3H). |

TABLE 10-continued

| Example No. | Structure (yield) | LC-MS: $R_t$ [min] (Method); MS (ESI): m/z [M + H]+ | 1H NMR (DMSO-$d_6$): |
|---|---|---|---|
| 74 | 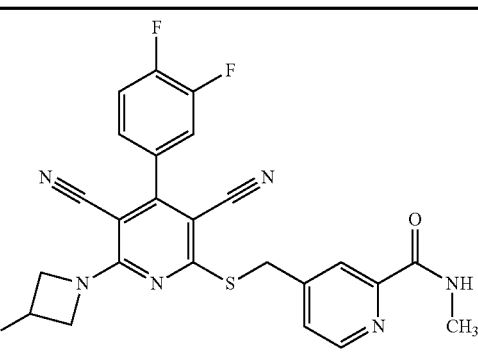<br>(75% of theory) | 1.14 min (Method 6); m/z = 493 | δ (500 MHz) = 8.76 (q, 1H), 8.58 (d, 1H), 8.14 (s, 1H), 7.79-7.73 (m, 1H), 7.70-7.63 (m, 2H), 7.45-7.40 (m, 1H), 5.94-5.86 (br s, 1H), 4.68-4.54 (m, 5H), 4.15-4.05 (m, 2H), 2.81 (d, 3H). |

*22 Different procedure; reaction time overnight at RT.

Example 75

4-[({3,5-Dicyano-6-[(2-hydroxyethyl)(methyl)amino]-4-phenylpyridin-2-yl}sulfanyl)methyl]-N-methylpyridine-2-carboxamide

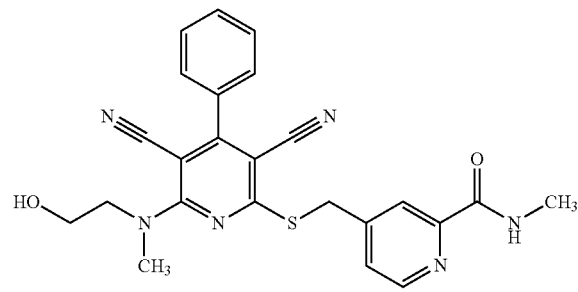 [SMILES: CNC(=O)c1cc(CSc2nc(N(C)CCO)c(C#N)c(-c3ccccc3)c2C#N)ccn1]

63 mg (0.15 mmol) of 4-{[(6-chloro-3,5-dicyano-4-phenylpyridin-2-yl)sulfanyl]methyl}-N-methylpyridine-2-carboxamide Example 75A were initially charged in 1.26 ml of DMF. After addition of 33.8 mg (0.45 mmol) of 2-(methylamino)ethanol, the mixture was stirred at RT for 1 h.

Water and tetrahydrofuran were added to the reaction mixture until a clear solution had formed. The solution was purified by preparative HPLC (Chromasil, water/acetonitrile+ 0.1% trifluoroacetic acid).

Yield: 58.3 mg (85% of theory)

LC-MS (Method 6): $R_t$=1.07 min; MS (ESIpos): m/z=459 [M+H]+.

1H NMR (400 MHz, DMSO-$d_6$): δ=8.79 (q, 1H), 8.58 (d, 1H), 8.12 (s, 1H), 7.67-7.63 (m, 1H), 7.60-7.52 (m, 5H), 4.66 (s, 2H), 3.78 (t, 2H), 3.56 (t, 2H), 3.35 (s, 3H), 2.82 (d, 3H).

The examples listed in Table 11 were prepared from the appropriate starting materials analogously to Example 75.

TABLE 11

| Example No. | Structure (yield) | LC-MS: $R_t$ [min] (Method); MS (ESI): m/z [M + H]+ | 1H NMR (DMSO-$d_6$): |
|---|---|---|---|
| 76 | 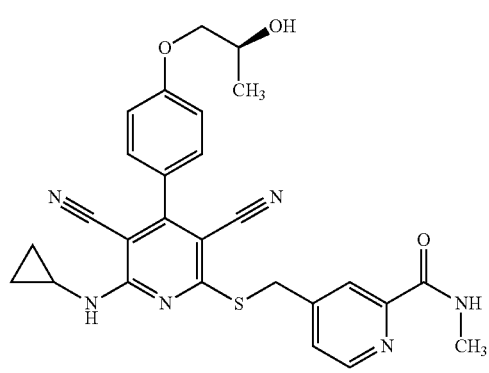 [SMILES: CNC(=O)c1cc(CSc2nc(NC3CC3)c(C#N)c(-c3ccc(OC[C@H](C)O)cc3)c2C#N)ccn1]<br>(60% of theory) | 1.13 min (Method 6); m/z = 515 | δ = 8.81-8.74 (m, 1H), 8.60-8.54 (m, 1H), 8.31-8.26 (m, 1H), 8.15 (s, 1H), 7.70-7.65 (m, 1H), 7.47 (d, 2H), 7.09 (d, 2H), 4.92 (d, 1H), 4.71 (s, 2H), 4.02-3.85 (m, 3H), 2.94-2.85 (m, 1H), 2.81 (d, 3H), 1.17 (d, 3H), 0.75-0.63 (m, 4H). |

TABLE 11-continued
| Example No. | Structure (yield) | LC-MS: R$_t$ [min] (Method); MS (ESI): m/z [M + H]$^+$ | $^1$H NMR (DMSO-d$_6$): |
|---|---|---|---|
| 77 | 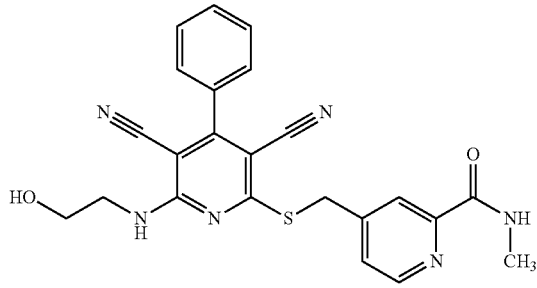 [SMILES: CNC(=O)c1cc(CSc2nc(NCCO)c(C#N)c(-c3ccccc3)c2C#N)ccn1]<br>(80% of theory)<br>*23 | 1.04 min (Method 6); m/z = 445 | δ = 8.79 (q, 1H), 8.58 (d, 1H), 8.13 (s, 1H), 8.02 (t, 1H), 7.67-7.64 (m, 1H), 7.60-7.50 (m, 5H), 4.66 (s, 2H), 3.55-3.35 (m, 4H), 2.81 (d, 3H). |
| 78 | 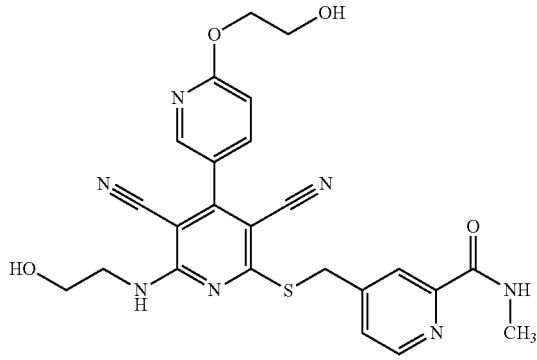 [SMILES: CNC(=O)c1cc(CSc2nc(NCCO)c(C#N)c(-c3ccc(OCCO)nc3)c2C#N)ccn1]<br>(59% of theory)<br>*23 | 1.76 min (Method 3); m/z = 506 | δ = 8.79 (q, 1H), 8.58 (d, 1H), 8.36 (d, 1H), 8.13 (s, 1H), 8.08 (t, 1H), 7.95-7.91 (m, 1H), 7.67-7.64 (m, 1H), 7.01 (d, 1H), 4.88 (t, 1H), 4.77 (t, 1H), 4.66 (s, 2H), 4.36 (t, 2H), 3.73 (q, 2H), 3.53-3.42 (m, 4H), 2.81 (d, 3H). |
| 79 | 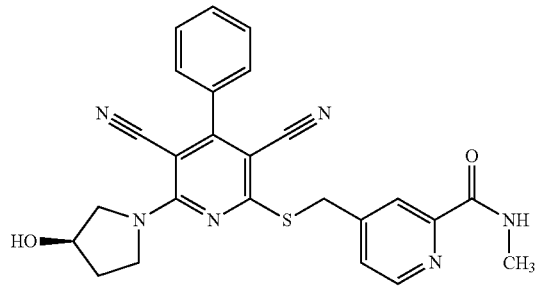 [SMILES: CNC(=O)c1cc(CSc2nc(N3CC[C@@H](O)C3)c(C#N)c(-c3ccccc3)c2C#N)ccn1]<br>(73% of theory)<br>*23 | 1.71 min (Method 4); m/z = 471 | δ = 8.77 (q, 1H), 8.58 (d, 1H), 8.14 (s, 1H), 7.67-7.64 (m, 1H), 7.59-7.50 (m, 5H), 5.20-5.05 (br s, 1H), 4.67 (s, 2H), 4.40-4.35 (m, 1H), 3.90-3.72 (m, 3H), 3.71-3.63 (m, 1H), 2.82 (d, 3H), 2.01-1.85 (m, 2H). |

TABLE 11-continued
| Example No. | Structure (yield) | LC-MS: R_t [min] (Method); MS (ESI): m/z [M + H]+ | $^1$H NMR (DMSO-d$_6$): |
|---|---|---|---|
| 80 | 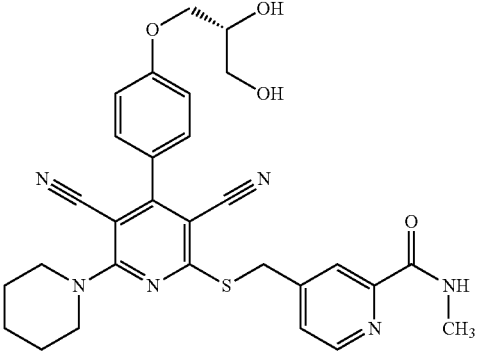 [SMILES: CNC(=O)c1cc(CSc2nc(N3CCCCC3)c(C#N)c(-c3ccc(OC[C@H](O)CO)cc3)c2C#N)ccn1]<br>(79% of theory)<br>*23 | 1.11 min (Method 6); m/z = 559 | δ = 8.77 (q, 1H), 8.58 (d, 1H), 8.13 (s, 1H), 7.66-7.63 (m, 1H), 7.53 (d, 2H), 7.10 (d, 2H), 4.63 (s, 2H), 4.12-4.07 (m, 1H), 4.00-3.93 (m, 1H), 3.85-3.79 (m, 1H), 3.78-3.73 (m, 4H), 3.46 (d, 2H), 2.81 (d, 3H), 1.67-1.59 (m, 2H), 1.58-1.50 (m, 4H). |
| 81 | 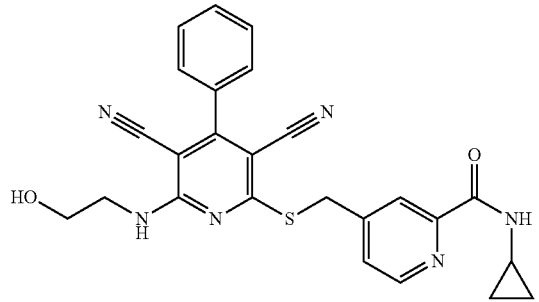 [SMILES: N#Cc1c(NCCO)nc(SCc2ccnc(C(=O)NC3CC3)c2)c(C#N)c1-c1ccccc1]<br>(75% of theory)<br>*23 | 1.79 min (Method 4); m/z = 471 | δ = 8.82-8.72 (m, 1H), 8.63-8.51 (m, 1H), 8.19-8.09 (m, 1H), 8.03 (t, 1H), 7.72-7.63 (m, 1H), 7.60-7.50 (m, 5H), 4.65 (s, 2H), 3.53-3.43 (m, 4H), 2.94-2.86 (m, 1H), 0.72-0.64 (m, 4H). |
| 82 | 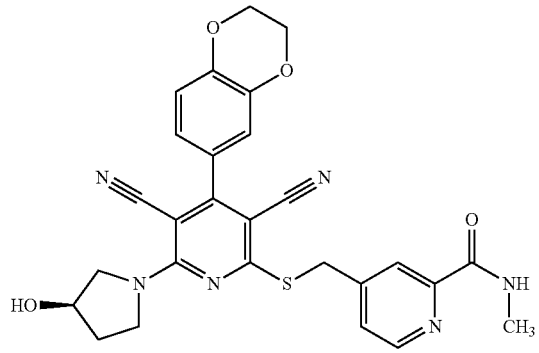 [SMILES: CNC(=O)c1cc(CSc2nc(N3CC[C@@H](O)C3)c(C#N)c(-c3ccc4c(c3)OCCO4)c2C#N)ccn1]<br>(81% of theory)<br>*23 | 2.15 min (Method 3); m/z = 529 | δ = 8.77 (q, 1H), 8.57 (d, 1H), 8.13 (s, 1H), 7.66-7.62 (m, 1H), 7.10-7.08 (m, 1H), 7.04-6.98 (m, 2H), 5.30-4.95 (br s, 1H), 4.65 (s, 2H), 4.40-4.28 (m, 5H), 3.89-3.71 (m, 3H), 3.69-3.61 (m, 1H), 2.81 (d, 3H), 2.01-1.82 (m, 2H). |

TABLE 11-continued
| Example No. | Structure (yield) | LC-MS: R_t [min] (Method); MS (ESI): m/z [M + H]+ | ¹H NMR (DMSO-d₆): |
|---|---|---|---|
| 83 | 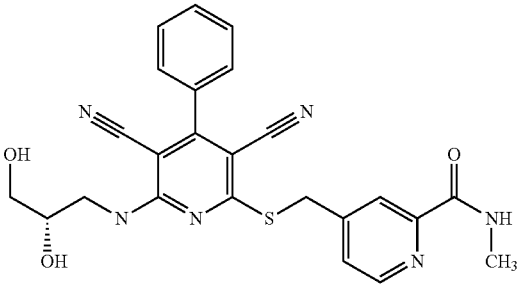 [SMILES: CNC(=O)c1cc(CSc2nc(NC[C@H](O)CO)c(C#N)c(-c3ccccc3)c2C#N)ccn1]<br>(97% of theory) | 2.11 min (Method 3); m/z = 475 | δ = 8.79 (q, 1H), 8.57 (d, 1H), 8.13 (s, 1H), 7.90 (t, 1H), 7.69-7.66 (m, 1H), 7.60-7.51 (m, 5H), 4.74-4.64 (m, 2H), 3.75-3.60 (m, 2H), 3.44-3.31 (m, 3H), 2.82 (d, 3H). |
| 84 | 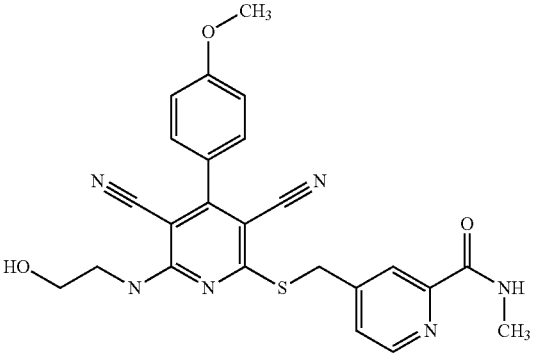 [SMILES: CNC(=O)c1cc(CSc2nc(NCCO)c(C#N)c(-c3ccc(OC)cc3)c2C#N)ccn1]<br>(72% of theory)<br>*23 | 1.69 min (Method 4); m/z = 475 | δ = 8.78 (q, 1H), 8.57 (d, 1H), 8.12 (s, 1H), 7.95 (t, 1H), 7.67-7.63 (m, 1H), 7.50 (d, 2H), 7.11 (d, 2H), 4.76 (t, 1H), 4.65 (s, 2H), 3.84 (s, 3H), 3.52-3.41 (m, 4H), 2.82 (d, 3H). |
| 85 | 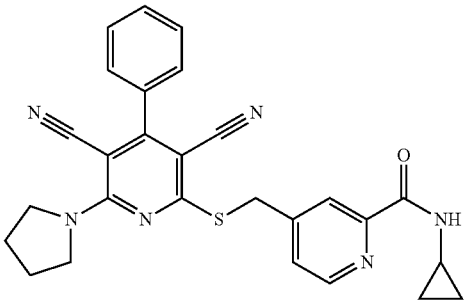 [SMILES: N#Cc1c(SCc2ccnc(C(=O)NC3CC3)c2)nc(N2CCCC2)c(C#N)c1-c1ccccc1]<br>(27% of theory)<br>*23 | 2.19 min (Method 4); m/z = 481 | δ = 8.75-8.70 (m, 1H), 8.56 (d, 1H), 8.14 (s, 1H), 7.67-7.64 (m, 1H), 7.59-7.49 (m, 5H), 4.66 (s, 2H), 3.80-3.69 (m, 4H), 2.91-2.87 (br s, 1H), 1.95-1.89 (m, 4H), 0.71-0.64 (m, 4H). |
| 86 | 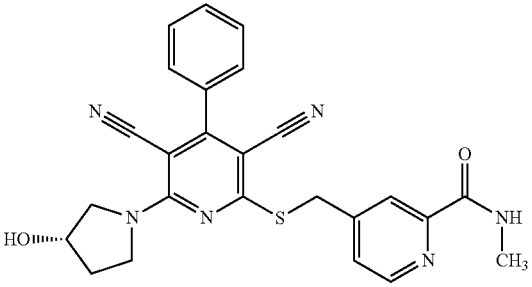 [SMILES: CNC(=O)c1cc(CSc2nc(N3CC[C@H](O)C3)c(C#N)c(-c3ccccc3)c2C#N)ccn1]<br>(70% of theory)<br>*23 | 2.22 min (Method 3); m/z = 471 | δ = 8.77 (q, 1H), 8.58 (d, 1H), 8.14 (s, 1H), 7.67-7.64 (m, 1H), 7.58-7.51 (m, 5H), 4.67 (s, 2H), 4.40-4.35 (m, 1H), 3.90-3.63 (m, 4H), 2.82 (d, 3H), 2.01-1.85 (m, 2H). |

TABLE 11-continued
| Example No. | Structure (yield) | LC-MS: R$_t$ [min] (Method); MS (ESI): m/z [M + H]$^+$ | $^1$H NMR (DMSO-d$_6$): |
|---|---|---|---|
| 87 | 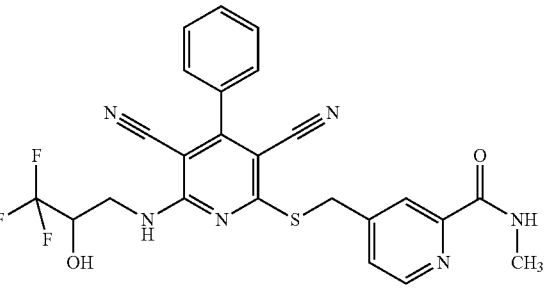<br>(82% of theory)<br>*23 | 1.17 min (Method 6); m/z = 513 | δ = 8.77 (q, 1H), 8.57 (d, 1H), 8.24 (t, 1H), 8.09 (s, 1H), 7.63-7.53 (m, 6H), 6.56-6.48 (br s, 1H), 4.75-4.63 (m, 2H), 4.30-4.20 (m, 1H), 3.78-3.70 (m, 1H), 3.63-3.54 (m, 1H), 2.82 (d, 3H). |
| 88 | 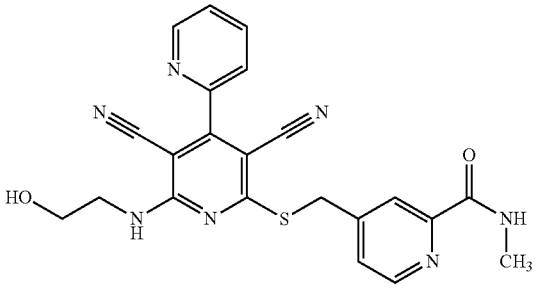 [SMILES: CNC(=O)c1cc(CSc2nc(NCCO)c(C#N)c(-c3ccccn3)c2C#N)ccn1]<br>(24% of theory) | 1.85 min (Method 3); m/z = 446 | δ = 8.82-8.76 (m, 2H), 8.58 (d, 1H), 8.14-8.03 (m, 3H), 7.78 (d, 1H), 7.67-7.64 (m, 1H), 7.63-7.59 (m, 1H), 4.77 (t, 1H), 4.68 (s, 2H), 3.53-3.42 (m, 4H), 2.82 (d, 3H). |
| 89 | 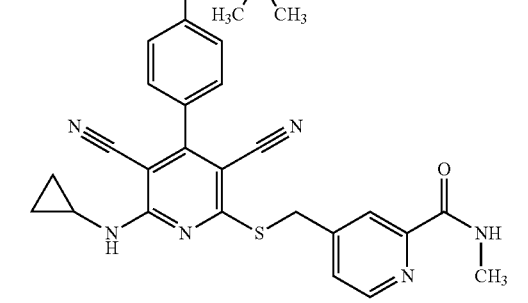<br>(40% of theory) | 2.34 min (Method 3); m/z = 529 | δ = 8.77 (q, 1H), 8.57 (d, 1H), 8.31-8.27 (m, 1H), 8.15 (s, 1H), 7.68-7.65 (m, 1H), 7.46 (d, 2H), 7.09 (d, 2H), 4.71 (s, 2H), 3.79 (s, 2H), 2.93-2.85 (m, 1H), 2.81 (d, 3H), 1.22 (s, 6H), 0.75-0.64 (m, 4H). |

TABLE 11-continued

| Example No. | Structure (yield) | LC-MS: $R_t$ [min] (Method); MS (ESI): m/z [M + H]+ | 1H NMR (DMSO-$d_6$): |
|---|---|---|---|
| 90 | (65% of theory) | 1.22 min (Method 6); m/z = 531 | δ = 8.77 (q, 1H), 8.58 (d, 1H), 8.17 (t, 1H), 8.09 (s, 1H), 7.64-7.60 (m, 1H), 7.50 (d, 2H), 7.10 (d, 2H), 4.92 (d, 1H), 4.66 (s, 2H), 4.03-3.94 (m, 1H), 3.93-3.86 (m, 2H), 3.12 (t, 2H), 2.81 (d, 3H), 1.85-1.73 (m, 1H), 1.17 (d, 3H), 0.72 (d, 6H). |
| 91 | (96% of theory) *23 | 1.22 min (Method 6); m/z = 531 | δ = 8.77 (q, 1H), 8.58 (d, 1H), 8.11 (s, 1H), 7.82 (t, 1H), 7.66-7.63 (m, 1H), 7.51 (d, 2H), 7.11 (d, 2H), 5.03-4.85 (br s, 1H), 4.66 (s, 2H), 4.08 (t, 2H), 3.74 (t, 2H), 3.18 (d, 2H), 2.81 (d, 3H), 0.77 (s, 9H). |

*23 Different solvent: tetrahydrofuran

Example 92
4-({[3,5-Dicyano-4-(4-fluorophenyl)-6-(3-hydroxyazetidin-1-yl)pyridin-2-yl]oxy}methyl)-N-methylpyridine-2-carboxamide

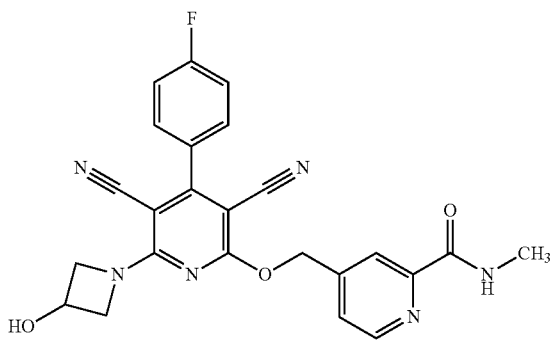 [SMILES: CNC(=O)c1cc(COc2nc(N3CC(O)C3)c(C#N)c(-c3ccc(F)cc3)c2C#N)ccn1]

50 mg (0.12 mmol) of 4-({[6-chloro-3,5-dicyano-4-(4-fluorophenyl)pyridin-2-yl]oxy}methyl)-N-methylpyridine-2-carboxamide Example 81A were initially charged in 1.5 ml of DMF. After addition of 26 mg (0.24 mmol) of azetidin-3-ol hydrochloride and 24 mg (0.24 mmol) of triethylamine, the mixture was stirred at RT overnight. The reaction mixture was purified by preparative HPLC (Chromasil, water/acetonitrile).

Yield: 33.9 mg (62% of theory)
LC-MS (Method 3): $R_t$=2.13 min; MS (ESIpos): m/z=459 [M+H]+.

1H NMR (400 MHz, DMSO-$d_6$): δ=8.81 (q, 1H), 8.66 (d, 1H), 8.10 (s, 1H), 7.65-7.58 (m, 3H), 7.46-7.39 (m, 2H), 5.88 (d, 1H), 5.63 (s, 2H), 4.60-4.52 (m, 3H), 4.15-3.95 (m, 2H), 2.82 (d, 3H).

Example 93
4-({[3,5-Dicyano-6-(3-hydroxyazetidin-1-yl)-4-phenylpyridin-2-yl]oxy}methyl)-N-methylpyridine-2-carboxamide

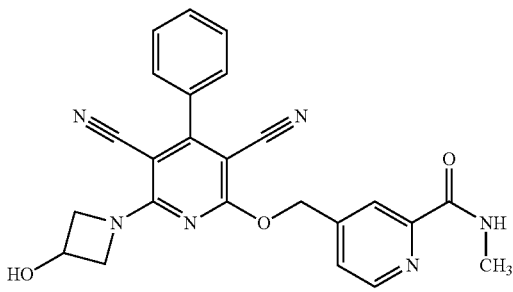

The preparation was carried out as described in Example 92 using the appropriate starting material (Example 83A).

Yield: (87% of theory)

LC-MS (Method 4): $R_t$=1.63 min; MS (ESIpos): m/z=441 [M+H]$^+$.

$^1$H NMR (400 MHz, DMSO-d$_6$): δ=8.81 (q, 1H), 8.66 (d, 1H), 8.10 (s, 1H), 7.66-7.62 (m, 1H), 7.60-7.50 (m, 5H), 5.88 (d, 1H), 5.64 (s, 2H), 4.63-4.47 (m, 3H), 4.15-3.94 (m, 2H), 2.83 (d, 3H).

Example 94

3-[({3,5-Dicyano-4-[4-(2-hydroxyethoxy)phenyl]-6-[(3R)-3-hydroxypyrrolidin-1-yl]pyridin-2-yl}-sulfanyl)methyl]-N-methylbenzenecarboxamide

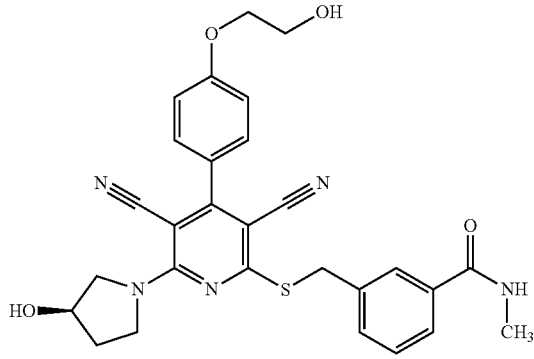 [SMILES: CNC(=O)c1cccc(CSc2nc(N3CC[C@@H](O)C3)c(C#N)c(-c3ccc(OCCO)cc3)c2C#N)c1]

73 mg (0.15 mmol) of 3-[({6-chloro-3,5-dicyano-4-[4-(2-hydroxyethoxy)phenyl]pyridin-2-yl}sulfanyl)methyl]-N-methylbenzenecarboxamide Example 84A were initially charged in 1.5 ml of tetrahydrofuran. After addition of 26.6 mg (0.31 mmol) of (R)-3-pyrrolidinol, the mixture was stirred at RT for 30 min. Water was added to the reaction mixture until a clear solution had formed. The solution was purified by preparative HPLC (Chromasil, water/acetonitrile+0.1% trifluoroacetic acid).

Yield: 46 mg (57% of theory)

LC-MS (Method 6): $R_t$=0.96 min; MS (ESIpos): m/z=530 [M+H]$^+$.

$^1$H NMR (400 MHz, DMSO-d$_6$): δ=8.49-8.41 (m, 1H), 7.92 (s, 1H), 7.72 (d, 1H), 7.58 (d, 1H), 7.50-7.40 (m, 3H), 7.10 (d, 2H), 5.16-5.11 (m, 1H), 4.91 (t, 1H), 4.60 (s, 2H), 4.44-4.38 (br s, 1H), 4.07 (t, 2H), 3.96-3.84 (m, 3H), 3.78-3.70 (m, 3H), 2.78 (d, 3H), 2.05-1.87 (m, 2H).

Example 95

3-({[3,5-Dicyano-6-(3-hydroxyazetidin-1-yl)-4-phenylpyridin-2-yl]sulfanyl}methyl)-N-methylbenzenecarboxamide

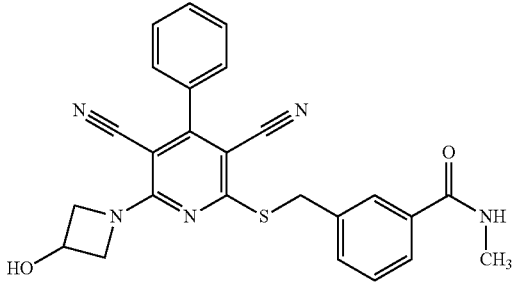 [SMILES: CNC(=O)c1cccc(CSc2nc(N3CC(O)C3)c(C#N)c(-c3ccccc3)c2C#N)c1]

50 mg (0.12 mmol) of 3-{[(6-chloro-3,5-dicyano-4-phenylpyridin-2-yl)sulfanyl]methyl}-N-methylbenzenecarboxamide Example 85A were initially charged in 1 ml of tetrahydrofuran. After addition of 19.6 mg (0.18 mmol) of azetidin-3-ol hydrochloride and 24.2 mg (0.24 mmol) of triethylamine, the mixture was stirred at RT for 30 min. Water was added to the reaction mixture until a clear solution had formed. The solution was purified by preparative HPLC (Chromasil, water/acetonitrile+0.1% trifluoroacetic acid).

Yield: 43 mg (79% of theory)

LC-MS (Method 4): $R_t$=1.72 min; MS (ESIpos): m/z=456 [M+H]$^+$.

$^1$H NMR (400 MHz, DMSO-d$_6$): δ=8.48-8.40 (m, 1H), 7.93 (s, 1H), 7.72 (d, 1H), 7.61-7.47 (m, 6H), 7.43 (t, 1H), 5.90 (d, 1H), 4.73-4.56 (m, 3H), 4.57 (s, 2H), 4.22-4.11 (m, 2H), 2.78 (d, 3H).

Example 96

3-({[6-Amino-3,5-dicyano-4-(4-fluorophenyl)pyridin-2-yl]sulfanyl}methyl)-N-[(2R)-2,3-dihydroxypropyl]benzenecarboxamide

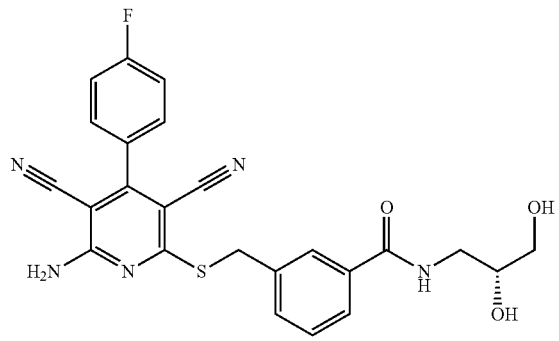 [SMILES: N#Cc1c(N)nc(SCc2cccc(C(=O)NC[C@@H](O)CO)c2)c(C#N)c1-c1ccc(F)cc1]

50 mg (0.12 mmol) of 3-({[6-amino-3,5-dicyano-4-(4-fluorophenyl)pyridin-2-yl]sulfanyl}methyl)-benzenecarboxylic acid Example 14 were initially charged in 1.2 ml of DMF. The reaction solution was cooled to 0° C. After addition of 94 mg (0.25 mmol) of HATU, the mixture was stirred at 0° C. for 20 min. 22.5 mg (0.25 mmol) of (R)-3-amino-1,2-propanediol and 32 mg (0.25 mmol) of N,N-diisopropylethylamine were added, and the reaction solution was stirred at RT overnight. Water and tetrahydrofuran were added to the reaction mixture until a clear solution had formed. The solution was purified by preparative HPLC (Chromasil, water/acetonitrile+0.1% trifluoroacetic acid).

Yield: 47 mg (80% of theory)

LC-MS (Method 10): $R_t$=1.78 min; MS (ESIpos): m/z=478 [M+H]$^+$.

$^1$H NMR (400 MHz, DMSO-d$_6$): δ=8.39 (t, 1H), 8.35-7.95 (br s, 2H), 7.99 (s, 1H), 7.77-7.68 (m, 2H), 7.65-7.58 (m, 2H), 7.45-7.37 (m, 3H), 4.81 (d, 1H), 4.61-4.53 (m, 3H), 3.69-3.60 (m, 1H), 3.44-3.31 (m, 3H), 3.24-3.15 (m, 1H).

Example 97

3-[({6-Amino-3,5-dicyano-4-[4-(2-hydroxyethoxy)phenyl]pyridin-2-yl}sulfanyl)methyl]-N-ethylbenzenecarboxamide

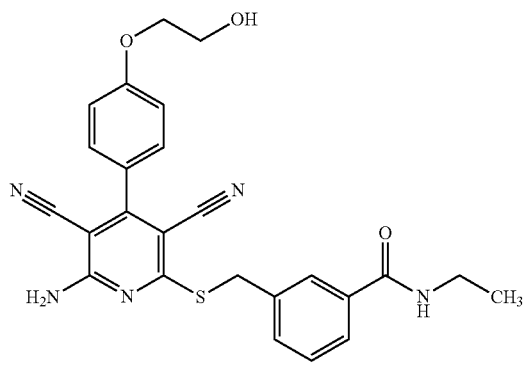 [SMILES: CCNC(=O)c1cccc(CSc2nc(N)c(C#N)c(-c3ccc(OCCO)cc3)c2C#N)c1]

The preparation was carried out as described in Example 96 using the appropriate starting material (Example 10).

Yield: 93 mg (88% of theory)

LC-MS (Method 4): $R_t$=1.57 min; MS (ESIpos): m/z=474 [M+H]$^+$.

$^1$H NMR (400 MHz, DMSO-d$_6$): δ=8.44 (t, 1H), 8.30-7.95 (br s, 2H), 7.97 (s, 1H), 7.75-7.66 (m, 2H), 7.47 (d, 2H), 7.40 (t, 1H), 7.09 (d, 2H), 4.91 (t, 1H), 4.54 (s, 2H), 4.07 (t, 2H), 3.74 (q, 2H), 3.33-3.24 (m, 2H), 1.12 (t, 3H).

Example 98

3-[({3,5-Dicyano-4-[4-(2-hydroxyethoxy)phenyl]-6-pyrrolidin-1-ylpyridin-2-yl}sulfanyl)methyl]-N-ethylbenzenecarboxamide

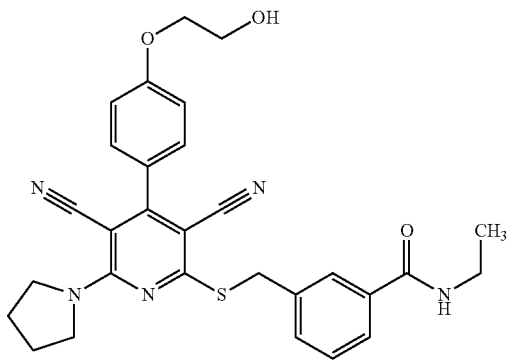 [SMILES: CCNC(=O)c1cccc(CSc2nc(N3CCCC3)c(C#N)c(-c3ccc(OCCO)cc3)c2C#N)c1]

The preparation was carried out as described in Example 96 using the appropriate starting material (Example 24).

Yield: 50 mg (95% of theory)

LC-MS (Method 3): $R_t$=2.35 min; MS (ESIpos): m/z=528 [M+H]$^+$.

$^1$H NMR (400 MHz, DMSO-d$_6$): δ=8.48 (t, 1H), 7.93 (s, 1H), 7.73 (d, 1H), 7.58 (d, 1H), 7.50.7.40 (m, 3H), 7.09 (d, 2H), 4.98-4.84 (br s, 1H), 4.60 (s, 2H), 4.07 (t, 2H), 3.86-3.77 (m, 4H), 3.74 (t, 2H), 3.32-3.24 (m, 2H), 1.99-1.91 (m, 4H), 1.12 (t, 3H).

Example 99

3-{[(3,5-Dicyano-6-{[(2R)-2,3-dihydroxypropyl]amino}-4-phenylpyridin-2-yl)sulfanyl]methyl}-benzenecarboxamide

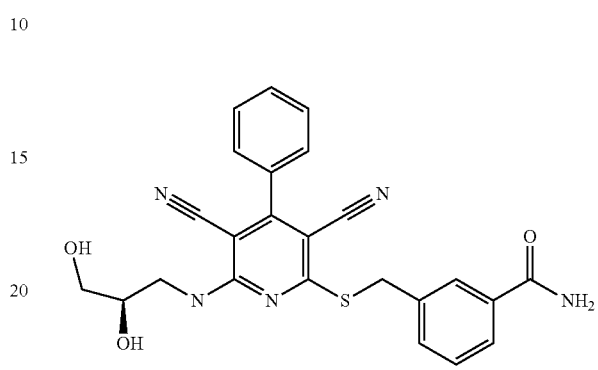

68 mg (0.15 mmol) of 3-{[(3,5-dicyano-6-{[(2R)-2,3-dihydroxypropyl]amino}-4-phenylpyridin-2-yl)sulfanyl]methyl}benzenecarboxylic acid Example 23 were dissolved in 3.4 ml of DMF. After addition of 42.5 mg (0.22 mmol) of EDC and 29.9 mg (0.22 mmol) of HOBT, the mixture was stirred at RT for 10 min. 39.5 mg (0.74 mmol) of ammonium chloride and 133.6 mg (1.03 mmol) of N,N-diisopropylethylamine were added, and the reaction mixture was stirred at RT overnight. Water and tetrahydrofuran were added to the reaction mixture until a clear solution had formed. The solution was purified by preparative HPLC (Chromasil, water/acetonitrile+0.1% trifluoroacetic acid).

Yield: 55.6 mg (82% of theory)

LC-MS (Method 3): $R_t$=2.08 min; MS (ESIpos): m/z=460 [M+H]$^+$.

$^1$H NMR (400 MHz, DMSO-d$_6$): δ=8.01-7.94 (m, 2H), 7.92 (t, 1H), 7.78 (d, 1H), 7.62 (d, 1H), 7.59-7.51 (m, 5H), 7.45-7.39 (m, 2H), 4.96 (d, 1H), 4.74 (t, 1H), 4.68-4.57 (m, 2H), 3.83-3.69 (m, 2H), 3.53-3.34 (m, 3H).

Example 100

3-({[3,5-Dicyano-4-(4-{[(2R)-2,3-dihydroxypropyl]oxy}phenyl)-6-pyrrolidin-1-ylpyridin-2-yl]sulfanyl}methyl)benzenecarboxamide

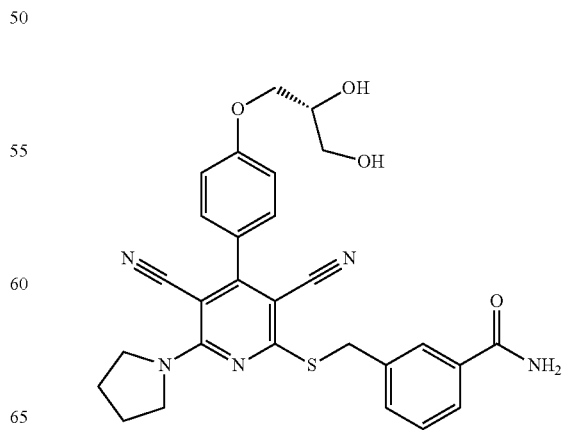

The preparation was carried out as described in Example 75 and Example 99 using the appropriate starting material (Example 79A).

Yield: 14 mg (32% of theory)

LC-MS (Method 10): $R_t$=1.73 min; MS (ESIpos): m/z=530 [M+H]$^+$.

$^1$H NMR (400 MHz, DMSO-d$_6$): δ=7.99-7.95 (m, 2H), 7.77 (d, 1H), 7.59 (d, 1H), 7.49-7.38 (m, 4H), 7.09 (d, 2H), 4.59 (s, 2H), 4.11-4.06 (m, 1H), 3.97-3.92 (m, 1H), 3.85-3.78 (m, 5H), 3.46 (d, 2H), 1.98-1.92 (m, 4H).

Example 101

3-{[(6-Amino-3,5-dicyano-4-phenylpyridin-2-yl)sulfanyl]methyl}-N-(2-aminoethyl)benzenecarboxamide hydrochloride

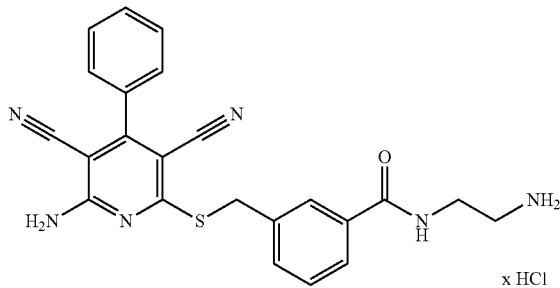 [SMILES: N#Cc1c(N)nc(SCc2cccc(C(=O)NCCN)c2)c(C#N)c1-c1ccccc1]

x HCl 79 mg (0.15 mmol) of tert-butyl (2-{[(3-{[(6-amino-3,5-dicyano-4-phenylpyridin-2-yl)sulfanyl]-methyl}phenyl)carbonyl]amino}ethyl)carbamate Example 57A were initially charged in 1 ml of dioxane. After addition of 21.6 mg (0.6 mmol) of 4 N hydrochloric acid in dioxane, the mixture was stirred at RT overnight. The reaction mixture was evaporated. The residue was purified by preparative HPLC (Chromasil, water/acetonitrile).

Yield: 67 mg (96% of theory)

LC-MS (Method 10): $R_t$=1.35 min; MS (ESIpos): m/z=429 [M+H]$^+$.

$^1$H NMR (400 MHz, DMSO-d$_6$): δ=8.60 (t, 1H), 8.40-7.95 (br s, 2H), 7.98 (s, 1H), 7.81-7.71 (m, 4H), 7.58-7.49 (m, 5H), 7.44 (t, 1H), 4.56 (s, 2H), 3.46-3.38 (m, 2H), 3.03-2.95 (m, 2H).

Example 102

3-[({6-Amino-3,5-dicyano-4-[4-(2-hydroxyethoxy)phenyl]pyridin-2-yl}oxy)methyl]-N-methylbenzenecarboxamide

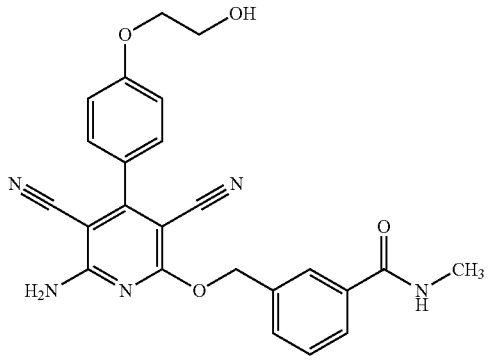

The preparation was carried out as described in Example 96 using the appropriate starting material (Example 18).

Yield: (75% of theory)

LC-MS (Method 4): $R_t$=1.36 min; MS (ESIpos): m/z=444 [M+H]$^+$.

$^1$H NMR (400 MHz, DMSO-d$_6$): δ=8.47 (q, 1H), 8.20-7.75 (br s, 2H), 7.94 (s, 1H), 7.81 (d, 1H), 7.67 (d, 1H), 7.53-7.45 (m, 3H), 7.10 (d, 2H), 5.50 (s, 2H), 5.05-4.70 (br s, 1H), 4.07 (t, 2H), 3.74 (t, 2H), 2.79 (d, 3H).

Example 103

3-{[(6-Amino-3,5-dicyano-4-phenylpyridin-2-yl)oxy]methyl}-N-methylbenzenecarboxamide

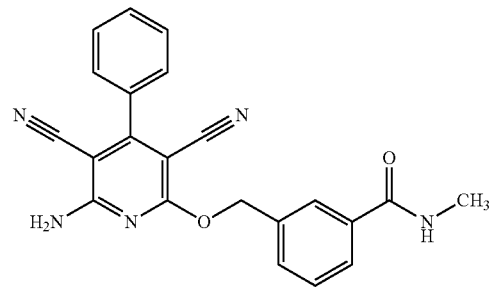

The preparation was carried out as described in Example 96 using the appropriate starting material (Example 20).

Yield: 31 mg (30% of theory)

LC-MS (Method 6): $R_t$=1.04 min; MS (ESIpos): m/z=384 [M+H]$^+$.

$^1$H NMR (400 MHz, DMSO-d$_6$): δ=8.47 (d, 1H), 8.40-7.70 (br s, 2H), 7.94 (s, 1H), 7.82 (d, 1H), 7.67 (d, 1H), 7.59-7.47 (m, 6H), 5.52 (s, 2H), 2.79 (d, 3H).

B. ASSESSING THE PHARMACOLOGICAL AND PHYSIOLOGICAL ACTIVITY

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (fetal calf serum) and in each case split 1:10 after 2-3 days. Test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5 \times 10^{-11}$ M to $3 \times 10^{-6}$ M (final concentration). 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiotreitol (DTT), pH 7.8) and 50% luciferase substrate solution (2.5 mM ATP, 0.5 mM luciferin, 0.1 mM coenzyme A, 10 mM tricine, 1.35 mM magnesium sulfate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase response is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", *Naunyn Schmiedebergs Arch. Pharmacol.*, 357, 1-9 (1998)].

Table A below lists the $EC_{50}$ values of representative working examples for the receptor stimulation on adenosine A1, A2a and A2b receptor subtypes:

TABLE A

| Example No. | $EC_{50}$ A1 [nM] (1 µM Forskolin) | $EC_{50}$ A2a [nM] | $EC_{50}$ A2b [nM] |
|---|---|---|---|
| 2 | 0.3 | 3000 | 3000 |
| 3 | 0.2 | 425 | 3000 |
| 4 | 0.3 | 3000 | 3000 |
| 6 | 0.06 | 3000 | 71 |
| 7 | 0.1 | 460 | 32 |
| 13 | 0.08 | 108 | 46 |
| 14 | 3.5 | 3000 | 3000 |
| 15 | 0.8 | 3000 | 106 |
| 21 | 0.9 | 3000 | 3000 |
| 26 | 0.2 | 65 | 243 |
| 27 | 0.3 | 3000 | 3000 |
| 28 | 0.4 | 1640 | 3000 |
| 29 | 0.5 | 3000 | 3000 |
| 30 | 0.4 | 1110 | 122 |
| 31 | 1.6 | 707 | 708 |
| 32 | 0.4 | 3000 | 2120 |
| 33 | 0.3 | 117 | 3.9 |
| 37 | 0.7 | 1780 | 3000 |
| 38 | 0.5 | 3000 | 3000 |
| 44 | 0.4 | 3000 | 3000 |
| 46 | 0.04 | 781 | 425 |
| 49 | 0.3 | 3000 | 3000 |
| 50 | 0.5 | 3000 | 3000 |
| 51 | 0.2 | 3000 | 3000 |
| 53 | 0.3 | 3000 | 3000 |
| 54 | 0.04 | 114 | 169 |
| 55 | 0.4 | 402 | 268 |
| 56 | 2.8 | 3000 | 3000 |
| 60 | 0.4 | 3000 | 1440 |
| 62 | 0.3 | 3000 | 262 |
| 65 | 3.3 | 3000 | 571 |
| 66 | 1.3 | 3000 | 3000 |
| 68 | 0.4 | 1740 | 440 |
| 70 | 0.2 | 272 | 1450 |
| 72 | 0.5 | 3000 | 3000 |
| 74 | 2.4 | 3000 | 3000 |
| 75 | 0.2 | 1010 | 175 |

TABLE A-continued

| Example No. | $EC_{50}$ A1 [nM] (1 µM Forskolin) | $EC_{50}$ A2a [nM] | $EC_{50}$ A2b [nM] |
|---|---|---|---|
| 78 | 0.1 | 355 | 393 |
| 82 | 0.2 | 1980 | 3000 |
| 83 | 0.2 | 2180 | 593 |
| 84 | 0.4 | 3000 | 3000 |
| 85 | 0.5 | 1020 | 3000 |
| 87 | 0.6 | 3000 | 3000 |
| 88 | 0.7 | 1980 | 3000 |
| 93 | 0.9 | 3000 | 3000 |
| 94 | 0.2 | 3000 | 3000 |
| 96 | 0.4 | 3000 | 204 |
| 98 | 0.3 | 1540 | 600 |
| 99 | 0.9 | 3000 | 3000 |
| 101 | 0.2 | 440 | 163 |

B-2. Studies on Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the decrease in the contraction of the vessels is measured. A decrease in contraction corresponds to dilation of the vessels. The concentration at which the contraction of the blood vessels is reduced by 50% is given as the $EC_{50}$ value of a test substance with respect to its relaxing properties.

B-3. Measurement of Blood Pressure and Heart Rate on Awake Marmosets

Various concentrations of test substances are administered orally to awake marmosets which carry an internal transmitter capable of measuring permanently both blood pressure and heart rate (telemetric monitoring of hemodynamic parameters). Blood pressure, heart rate and their changes are then recorded over a period of 6-24 hours.

B-4. Hemodynamic Measurements on Anesthetized Rats:

Wistar rats (body weight 250-300 g; from Harlan-Winkelmann) are anesthetized with 5% Isofluran®. Anesthesia is maintained with 2% Isofluran® and pressurized air in an anesthesia mask. The carotid artery is exposed, and a tip catheter (Millar Micro-Tip transducer, 2 French; from HSE) is inserted and advanced into the left ventricle. A second catheter is then inserted into the jugular vein. Through this catheder, placebo solution and test substance solutions in increasing concentration are infused into the animals. At the same time, the heart function (such as heart rate, left ventricular pressure, contractility (dp/dt), left-ventricular end-diastolic pressure) is measured via the left-ventricular catheter. By withdrawing the catheder from the left ventricle into the aorta, it is also possible to measure the systemic blood pressure.

B-5. Measurement of Blood Pressure and Heart Rate a) On Awake Rats:

Awake spontaneously hypertensive rats (SH rats) carrying an internal transmitter capable of measuring permanently both blood pressure and heart rate (telemetric monitoring of hemodynamic parameters) and sitting in a cage fitted with motion sensors are orally administered test substances in various dosages. Blood pressure and heart rate and changes thereof, and also the movements and the activity of the animals are then recorded and evaluated for 24 hours.

b) On Awake Dogs:

Awake male beagle dogs carrying an internal transmitter capable of measuring permanently both blood pressure and heart rate (telemetric monitoring of hemodynamic parameters) are administered test substances in various dosages orally or intraduodenally. Blood pressure and heart rate and changes thereof are then recorded and evaluated for 24 hours. At the same time, the behavior of the animals with respect to their activity (gait, side position, rest phases etc.) is observed to obtain indications of a possible CNS action of the substances.

B-6. GTP Shift Experiment

Preparation of the Brain Membrane

The brains of male Wistar rats are removed and immediately transferred into an ice-cooled 0.32 mol/l sucrose solution. The tissue is comminuted using a glass-Teflon homogenizer and then centrifuged (1000×g for 10 minutes). The supernatant is then ultracentrifuged at 30 000 g for 30 minutes. The pellet obtained in this manner is resuspended in 10 ml of water and allowed to stand on ice for 30 minutes. After a final centrifugation step at 48 000 g for 10 min, the membranes are resuspended in 50 mmol/l Tris-HCl buffer, pH 7.4, and incubated with 2 U/ml of adenosine deaminase at 37° C. for 30 min. This is followed by a protein determination according to Bradford. The membranes are frozen in small aliquots and stored at −80° C. until required for the binding assay.

Receptor Binding Study

The A1 receptor GTP shift binding assay is carried out using rat brain membranes and 0.4 nM [$^3$H] DPCPX ($K_d$=0.28 nM) as radioligand. 10 µg of membrane protein are incubated at 37° C. for 20 min with 0.4 nM [$^3$H]DPCPX and adenosine A1 agonists in various concentrations in buffer (50 mM tris-HCl, pH 7.4, 2 U/ml ADA) in the presence and absence of 1 mM guanosine triphosphate (GTP). The incubation is terminated by filtration through GF/B glass fiber filter plates. The filters are then washed three times with ice-cold tris-HCl buffer 50 mM, pH 7.4. The radioactivity on the filter is measured with addition of 100 µl of scintillation cocktail in a Microbeta TriLux beta counter (PerkinElmer, Massachusetts, USA).

Table B lists values for the GTP shifts of representative working examples.

TABLE B

| Example | GTP Shift |
|---------|-----------|
| 61 | 1.5 |
| 64 | 2.8 |

B-7. Test of Adenosine A1 Receptor Agonists on Locomotor Action in the Treadmill Experiment To determine the action of adenosine A1 receptor agonists on locomotor function, the running behavior of mice (strain: CD1) in treadmills (M. Weber et al., Psychopharmacology 2008, in print) is examined. To get the mice accustomed to voluntary use of the treadmill, 2-3 weeks prior to the start of the experiment the animals are isolated in cages with a treadmill and trained. 2 weeks prior to the start of the experiment, the movements of the mice in the treadmill are recorded by a photo cell using a computer, and various running parameters such as, for example, the distance run in a day, the individual distances covered, and also their distribution over the day are determined. According to their natural running behavior, the animals are randomized into groups (8-12 animals) (control group and 1—a plurality of substance groups). After the initial 2-week phase, the animals are treated orally with the substances to be tested. Here, single doses or else increasing dosages (for example 0.3-1-3-10-30 mg/kg) are administered. The substances are tested in two independent experiments. Between 2 experiments, there are at least 3 days where the animals are not administered any substances. The running behavior of the animals is observed and recorded for 24 hours after administration. Evaluation of the running intervals and the total distance covered takes place over a period of several hours during the main activity period of the mice. Effects are stated in percent of the control.

B-8. Determination of the Solubility

Reagents Required:

PBS buffer pH 6.5: 90.00 g of NaCl p.a. (for example from Merck, Art. No. 1.06404.1000), 13.61 g of KH$_2$PO$_4$ p.a. (for example from Merck, Art. No. 1.04873.1000) and 83.35 g of 1 N aqueous sodium hydroxide solution (for example from Bernd Kraft GmbH, Art. No. 01030.4000) are weighed into a 1 liter measuring flask, the flask is filled with distilled water to 1 liter and the mixture is stirred for 1 hour. Using 1 N hydrochloric acid (for example from Merck, Art. No. 1.09057.1000) the pH is then adjusted to 6.5.

PEG/water solution (30:70 v/v): 30 ml of polyethylene glycol 400 (for example from Merck, Art. No. 8.17003.1000) and 70 ml of distilled water are homogenized in a 100 ml measuring flask.

PEG/PBS buffer pH 6.5 (80:20 v/v): 80 ml of polyethylene glycol 400 (for example from Merck, Art. No. 8.17003.1000) and 20 ml of PBS buffer pH 6.5 are homogenized in a 100 ml measuring flask.

Dimethyl sulfoxide (for example from Baker, Art. No. 7157.2500)

Distilled water.

Preparation of the Starting Solution (Original Solution):

At least 4 mg of the test substance are weighed accurately into a wide-necked 10 mm screw V vial (from Glastechnik Gräfenroda GmbH, Art. No. 8004-WM-H/V15µ) with fitting screw cap and septum, in a pipetting robot DMSO is added to a concentration of 50 mg/ml and the mixture is shaken for 10 minutes.

Preparation of the Calibration Solutions:

Preparation of the Starting Solution for Calibration Solutions (Stock Solution):

With the aid of a pipetting robot, 10 µl of the original solution are transferred into a microtiter plate and made up with DMSO to a concentration of 600 µg/ml. The sample is shaken until everything has gone into solution.

Calibration Solution 1 (20 µg/ml):

1000 µl of DMSO are added to 34.4 µl of the stock solution, and the mixture is homogenized.

Calibration Solution 2 (2.5 µg/ml):

700 µl of DMSO are added to 100 µl of calibration solution 1, and the mixture is homogenized.

Preparation of the Sample Solutions:

Sample Solution for Solubilities of Up to 5 g/liter in PBS Buffer pH 6.5:

10 µl of the original solution are transferred into a microtiter plate, and 1000 µl of PBS buffer pH 6.5 are added.

Sample Solution for Solubilities of Up to 5 g/liter in PEG/Water (30:70):

10 µl of the original solution are transferred into a microtiter plate, and 1000 µl of PEG/water (30:70) are added.

Sample Solution for Solubilities of Up to 5 g/liter in PEG/PBS Buffer pH 6.5 (80:20):

10 µl of the original solution are transferred into a microtiter plate, and 1000 µl of PEG/PBS buffer pH 6.5 (80:20) are added.

Practice:

The sample solutions prepared in this manner are shaken at 1400 rpm in a temperature-adjustable shaker (for example Eppendorf Thermomixer comfort Art. No. 5355 000.011 with interchangeable block Art. No. 5362.000.019) at 20° C. for 24 hours. In each case 180 µl are taken from these solutions and transferred into Beckman Polyallomer Centrifuge Tubes (Art. No. 343621). These solutions are centrifuged at about 223 000×g for one hour (for example Beckman Optima L-90K Ultracentrifuge with Type 42.2 Ti Rotor at 42 000 rpm). From each of the sample solutions, 100 µl of the supernatant are removed and diluted 1:5 and 1:100 with DMSO. From each dilution, a sample is transferred into a vessel suitable for HPLC analysis.

Analysis:

The samples are analyzed by RP-HPLC. Quantification is carried out using a two-point calibration curve of the test compound in DMSO. The solubility is expressed in mg/liter. Analysis sequence: 1) calibration solution 2.5 mg/ml; 2) calibration solution 20 mg/ml; 3) sample solution 1:5; 4) sample solution 1:100.

HPLC Method for Acids:

Agilent 1100 with DAD (G1315A), quat. pump (G1311A), autosampler CTC HTS PAL, degasser (G1322A) and column thermostat (G1316A); column: Phenomenex Gemini C18, 50 mm×2 mm, 5µ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5µ; temperature: 30° C.; mobile phase A: water+5 ml of perchloric acid/liter; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

Table C lists the solubilities of representative working examples.

TABLE C

| Example | Solubility [mg/liter] PBS buffer | Solubility [mg/liter] PEG/water solution (30:70 v/v) |
|---|---|---|
| 13 |  | 210 |
| 33 | 5 | 53 |
| 61 |  | 90 |
| 64 |  | 260 |
| 99 | 9.0 | 440 |

B-9. Determination of the Metabolic Stability

To determine the metabolic stability of test compounds, the latter are incubated in vitro with liver microsomes or, preferably, with primary fresh hepatocytes of various animal species (for example from rat and dog) and also of human origin to obtain and to compare metabolite profiles of a hepatic phase I and phase II metabolism which is as complete as possible.

The test compounds are incubated at a concentration of 10-20 µM. To this end, stock solutions of the substances at a concentration of 1-2 mM in acetonitrile are prepared and then pipetted at a dilution of 1:100 into the incubation mixture. The liver microsomes are incubated at 37° C. in 50 mM potassium phosphate buffer (pH 7.4) with and without NADPH-generating system consisting of 1 mM NADP$^+$, 10 mM glucose 6-phosphate and 1 unit of glucose 6-phosphate dehydrogenase. Primary hepatocytes are also incubated at 37° C. in suspension in Williams E medium. After an incubation time of 0-4 hours, the incubation mixtures are quenched with acetonitrile (final concentration about 30%) and the protein is centrifuged off at about 15 000×g. The samples quenched in this manner are either analyzed directly or stored at −20° C. until analysis.

Analysis is carried out using high-performance liquid chromatography with ultraviolet and mass-spectrometric detection (HPLC-UV-MS/MS). To this end, the supernatants of the incubation samples are chromatographed using suitable C18 reversed-phase columns and variable mobile phase mixtures of acetonitrile and 10 mM aqueous ammonium formate solution. The UV chromatograms in combination with mass-spectrometric MS/MS data serve to identify the metabolites and to elucidate their structures.

B-10. CYP Inhibition Assay

The ability of substances to inhibit CYP1A2, CYP 2C8, CYP2C9, CYP2D6 and CYP3A4 in humans is investigated with pooled human liver microsomes as enzyme source in the presence of standard substrates (see below) which form CYP-isoform-specific metabolites. The inhibitory effects are investigated with six different concentrations of the test compounds (0.6, 1.3, 2.5, 5, 10 and 20 µM or 1.5, 3.1, 6.3, 12.5, 25 and 50 µM), compared with the extent of the CYP-isoform-specific metabolite formation of the standard substrates in the absence of the test compounds, and the corresponding IC$_{50}$ values are calculated. A standard inhibitor which specifically inhibits a single CYP isoform serves as control of the results obtained.

Procedure:

Incubation of phenacetin, amodiaquin, diclofenac, dextromethorphan or midazolam with human liver microsomes in the presence of in each case six different concentrations of a test compound (as potential inhibitor) is carried out on a work station (Tecan, Genesis, Crailsheim, Germany). Standard incubation mixtures comprise 1.0 mM NADP, 1.0 mM EDTA, 5.0 mM glucose 6-phosphate, glucose 6-phosphate dehydrogenase (1.5 U/ml) and 50 mM phosphate buffer (pH 7.4) in a total volume of 200 µl. Test compounds are preferably dissolved in acetonitrile. 96-well plates are incubated with pooled human liver microsomes at 37° C. for a defined time. The reactions are stopped by adding 100 µl of acetonitrile in which a suitable internal standard is always present. Precipitated proteins are removed by centrifugation, and the supernatants are combined and analyzed by LC-MS/MS.

B-11. Determination of Pharmacokinetic Parameters after Intravenous and Oral Administration The substance to be tested is administered intravenously as a solution to animals (for example mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS-MS. The plasma concentration/time courses found in this way are used to calculate the pharmacokinetic parameters such as AUC (area under the concentration, C$_{max}$ time curve), T$_{1/2}$ (half-life) and CL (clearance) by means of a validated pharmacokinetic computer program.

C. WORKING EXAMPLES OF PHARMACEUTICAL COMPOSITIONS

The compounds of the invention can be converted into pharmaceutical preparations in the following ways:

Tablet:
Composition:
  100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.
  Tablet weight 212 mg, diameter 8 mm, radius of curvature 12 mm.
Production:
  The mixture of compound of the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.
Suspension which can be Administered Orally:
Composition:
  1000 mg of the compound of the invention, 1000 mg of ethanol (96%), 400 mg of Rhodigel® (xanthan gum from FMC, Pennsylvania, USA) and 99 g of water.
  10 ml of oral suspension correspond to a single dose of 100 mg of the compound of the invention.
Production:
  The Rhodigel is suspended in ethanol, and the compound of the invention is added to the suspension. The water is added while stirring. The mixture is stirred for about 6 h until the swelling of the Rhodigel is complete.
Solution which can be Administered Orally:
Composition:
  500 mg of the compound of the invention, 2.5 g of polysorbate and 97 g of polyethylene glycol 400.20 g of oral solution correspond to a single dose of 100 mg of the compound of the invention.
Production:
  The compound of the invention is suspended in the mixture of polyethylene glycol and polysorbate with stirring. The stirring process is continued until the compound of the invention has completely dissolved.
i.v. Solution:
  The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

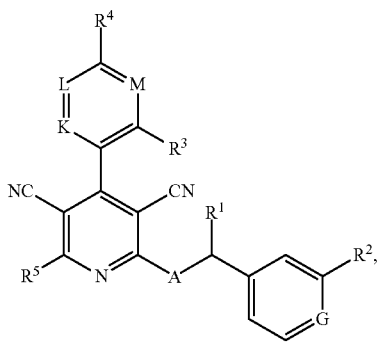

in which
A represents oxygen or sulfur,
G represents N,
K represents CH or CF
L represents N,
M represents $CR^7$,
  where
  $R^7$ represents hydrogen, fluorine, chlorine, difluoromethyl, trifluoromethyl or $(C_1-C_4)$-alkoxy,
    where $(C_1-C_4)$-alkoxy may be substituted by 1 or 2 hydroxyl substituents,
$R^1$ represents hydrogen or $(C_1-C_4)$-alkyl,
$R^2$ represents hydroxycarbonyl, aminocarbonyl, mono-$(C_1-C_4)$-alkylaminocarbonyl, di-$(C_1-C_4)$-alkylaminocarbonyl, $(C_3-C_7)$-cycloalkylaminocarbonyl, aminosulfonyl, $(C_1-C_4)$-alkylsulfonylamino or phenylsulfonylamino,
  where mono-$(C_1-C_4)$-alkylaminocarbonyl, di-$(C_1-C_4)$-alkylaminocarbonyl and $(C_3-C_7)$-cycloalkylaminocarbonyl may be substituted by 1 to 3 substituents independently of one another selected from the group consisting of fluorine, hydroxy and amino,
$R^3$ represents hydrogen, fluorine or methoxy,
$R^4$ represents hydrogen, fluorine, $(C_1-C_6)$-alkoxy, mono-$(C_1-C_4)$-alkylamino, di-$(C_1-C_4)$-alkylamino, $(C_1-C_4)$-alkylcarbonylamino, mono-$(C_1-C_4)$-alkylaminosulfonyloxy, di-$(C_1-C_4)$-alkylaminosulfonyloxy or 2-oxopyrrolidin-1-yl,
  where $(C_1-C_6)$-alkoxy may be substituted by 1 to 3 substituents independently of one another selected from the group consisting of trifluoromethyl, hydroxy, $(C_1-C_4)$-alkoxy, amino, mono-$(C_1-C_4)$-alkylamino, di-$(C_1-C_4)$-alkylamino, aminocarbonyl, mono-$(C_1-C_4)$-alkylaminocarbonyl, di-$(C_1-C_4)$-alkylaminocarbonyl and a group of the formula

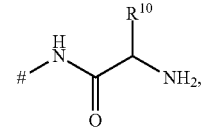

in which
  # represents the point of attachment to the alkoxy group,
  $R^{10}$ represents hydrogen, methyl, propan-2-yl, propan-1-yl, 2-methylpropan-1-yl, 1-methylpropan-1-yl, butan-1-yl, tert-butyl, phenyl, benzyl, p-hydroxybenzyl, indol-3-ylmethyl, imidazol-4-ylmethyl, hydroxymethyl, 2-hydroxyethyl, 1-hydroxyethyl, mercaptomethyl, methylthiomethyl, 2-mercaptoethyl, 2-methylthioethyl, carbamoylmethyl, 2-carbamoylethyl, carboxymethyl, 2-carboxyethyl, 4-aminobutan-1-yl, 4-amino-3-hydroxybutan-1-yl, 3-aminopropan-1-yl, 2-aminoethyl, aminomethyl, 3-guanidinopropan-1-yl, or 3-ureidopropan-1-yl,
$R^5$ represents hydrogen or $-NR^8R^9$,
  where
  $R^8$ represents hydrogen or $(C_1-C_4)$-alkyl,
  $R^9$ represents hydrogen, $(C_1-C_6)$-alkyl or $(C_3-C_7)$-cycloalkyl,
    where $(C_1-C_6)$-alkoxy may be substituted by 1 or 2 substituents independently of one another selected from the group consisting of fluorine, difluoromethyl, trifluoromethyl, hydroxy and $(C_1-C_4)$-alkoxy, or an N-oxide, salt of the N-oxide, or a salt thereof.

2. The compound of claim 1 in which

A represents oxygen or sulfur,

G represents N,

K represents CH, or CF

L represents N,

M represents $CR^7$, where $R^7$ represents hydrogen, fluorine, chlorine, difluoromethyl, trifluoromethyl, methoxy or ethoxy, where ethoxy may be substituted by 1 or 2 hydroxy substituents, $R^1$ represents hydrogen or methyl, $R^2$ represents hydroxycarbonyl, aminocarbonyl, methylaminocarbonyl, ethylaminocarbonyl, cyclopropylaminocarbonyl, cyclobutylaminocarbonyl, aminosulfonyl, methylsulfonylamino, ethylsulfonylamino or phenylsulfonylamino, where ethylaminocarbonyl, cyclopropylaminocarbonyl and cyclobutylaminocarbonyl may be substituted by 1 or 2 substituents independently of one another selected from the group consisting of fluorine, hydroxy and amino, $R^3$ represents hydrogen or fluorine, $R^4$ represents hydrogen, fluorine, $(C_1-C_4)$-alkoxy, methylamino, ethylamino, dimethylamino, diethylamino, methylcarbonylamino, ethylcarbonylamino, dimethylaminosulfonyloxy, dimethylaminosulfonyloxy or 2-oxopyrrolidin-1-yl, where $(C_1-C_4)$-alkoxy may be substituted by 1 to 3 substituents independently of one another selected from the group consisting of trifluoromethyl, hydroxy, methoxy, ethoxy, amino, methylamino, ethylamino, dimethylamino, diethylamino, aminocarbonyl, methylcarbonylamino, ethylcarbonylamino and a group of the formula

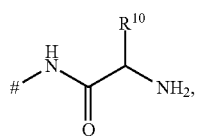

where $R^{10}$ represents hydrogen, methyl, 2-methylpropan-1-yl, hydroxymethyl, 1-hydroxyethyl, 4-aminobutan-1-yl or 3-aminopropan-1-yl, $R^5$ represents hydrogen or $-NR^8R^9$, where $R^8$ represents hydrogen, methyl or ethyl, $R^9$ represents hydrogen, $(C_1-C_6)$-alkyl or $(C_3-C_6)$-cycloalkyl, where $(C_1-C_6)$-alkyl may be substituted by 1 or 2 substituents independently of one another selected from the group consisting of fluorine, difluoromethyl, trifluoromethyl and hydroxy, or a salt thereof.

3. The compound of claim 1 in which

A represents sulfur,

G represents N,

K represents CH or CF,

L represents N,

M represents $CR^7$, where $R^7$ represents hydrogen, fluorine, trifluoromethyl, methoxy or 2-hydroxyethoxy, $R^1$ represents hydrogen, $R^2$ represents hydroxycarbonyl, aminocarbonyl, methylaminocarbonyl, ethylaminocarbonyl or cyclopropylaminocarbonyl, $R^3$ represents hydrogen, $R^4$ represents hydrogen, fluorine or $(C_1-C_4)$-alkoxy, where $(C_1-C_4)$-alkoxy may be substituted by 1 or 2 substituents independently of one another selected from the group consisting of trifluoromethyl, hydroxy, amino and a group of the formula

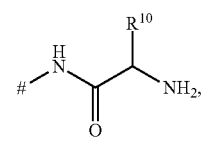

where $R^{10}$ represents hydrogen or methyl, $R^5$ represents hydrogen or $-NR^8R^9$, where $R^8$ represents hydrogen, $R^9$ represents hydrogen, $(C_1-C_6)$-alkyl or cyclopropyl, or a salt thereof.

4. A process for preparing a compound of the formula (I) as defined in claim 1 comprising:

[A] reacting a compound of the formula (II)

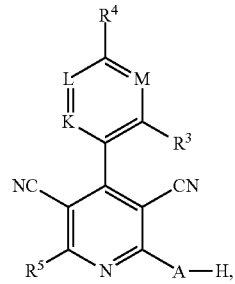

in which A, K, L, M, $R^3$, $R^4$ and $R^5$ each have the meanings given in claim 1, in an inert solvent in the presence of a base with a compound of the formula (III)

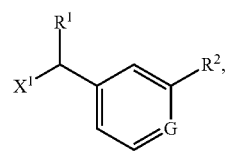

in which G, $R^1$ and $R^2$ each have the meanings given in claim 1 and $X^1$ represents a leaving group selected from the group consisting of halogen, in particular chlorine, bromine or iodine, or represents mesylate, tosylate or triflate, or

[B] in the case that A represents O, reacting a compound of the formula (IV)

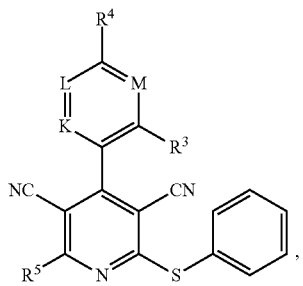
(IV)

in which K, L, M, $R^3$, $R^4$ and $R^5$ each have the meanings given in claim 1, in an inert solvent in the presence of a base with a compound of the formula (V)

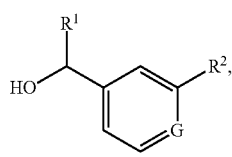
(V)

in which G, $R^1$ and $R^2$ each have the meanings given in claim 1, or

[C] reacting a compound of the formula (I-A)

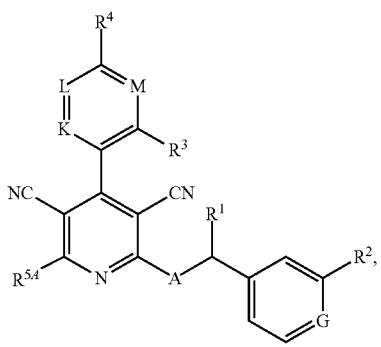
(I-A)

in which A, G, K, L, M, $R^1$, $R^2$, $R^3$ and $R^4$ each have the meanings given in claim 1 and $R^{5A}$ represents amino, in a suitable solvent with copper(II) chloride and isopentyl nitrite into a compound of the formula (VI)

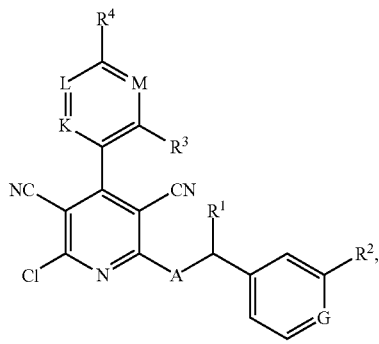
(VI)

in which A, G, K, L, M, $R^1$, $R^2$, $R^3$ and $R^4$ each have the meanings given in claim 1, and reacting the compound of formula (VI) in an inert solvent, optionally, in the presence of a base, with a compound of the formula (VII)

(VII)

in which $R^8$ and $R^9$ each have the meanings given in claim 1 and where at least one of the two radicals $R^8$ and $R^9$ is different from hydrogen, to give a compound of the formula (I-B)

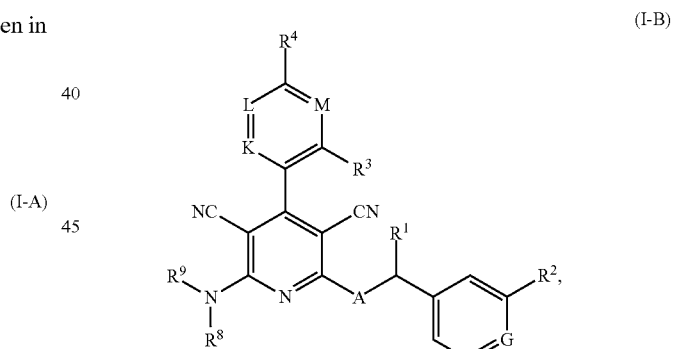
(I-B)

in which A, G, K, L, M, $R^1$, $R^2$, $R^3$, $R^4$, $R^8$ and $R^9$ each have the meanings given in claim 1, and where at least one of the two radicals $R^8$ and $R^9$ is different from hydrogen, any protective groups present are then removed and the resulting compound of the formulae (I), (I-A) and (I-B) is, optionally, reacted with a base or acid into a salt thereof.

5. A pharmaceutical composition, comprising a compound of claim 1 and an inert nontoxic pharmaceutically suitable auxiliary.

* * * * *